United States Patent [19]
Ikeda et al.

[11] Patent Number: 5,911,694
[45] Date of Patent: Jun. 15, 1999

[54] ENDOCELIAC PHYSICAL QUANTITY MEASURING APPARATUS HAVING EXCELLENT MEASURING RESOLUTION

[75] Inventors: Yuichi Ikeda, Tama; Akio Uchiyama, Urawa, both of Japan

[73] Assignee: Olympus Optical Co., Ltd., Tokyo, Japan

[21] Appl. No.: 08/902,498

[22] Filed: Jul. 29, 1997

[30] Foreign Application Priority Data

| Aug. 22, 1996 | [JP] | Japan | 8-221371 |
| Aug. 27, 1996 | [JP] | Japan | 8-224268 |
| Sep. 18, 1996 | [JP] | Japan | 8-246723 |
| Sep. 27, 1996 | [JP] | Japan | 8-256515 |
| Sep. 30, 1996 | [JP] | Japan | 8-279031 |

[51] Int. Cl.$^6$ .................................................. A61B 5/103
[52] U.S. Cl. ........................... 600/587; 600/552; 600/595; 73/579
[58] Field of Search .................................. 600/552, 587, 600/595; 73/573, 579

[56] References Cited

U.S. PATENT DOCUMENTS

| 3,572,097 | 3/1971 | Kleesattel | 73/67.2 |
| 4,297,884 | 11/1981 | Leveque et al. | 600/587 |
| 4,947,851 | 8/1990 | Sarvazyan et al. | 600/587 |
| 5,003,982 | 4/1991 | Halperin | 600/552 |
| 5,006,984 | 4/1991 | Steele | 600/587 |
| 5,115,808 | 5/1992 | Popovic et al. | 600/587 |
| 5,680,874 | 10/1997 | Takuno | 600/587 |
| 5,706,815 | 1/1998 | Sarvazyan et al. | 600/587 |
| 5,799,137 | 6/1998 | Omata | 600/587 |

FOREIGN PATENT DOCUMENTS

| 40-27236 | 11/1930 | Japan . |
| 40-27236 | 11/1940 | Japan . |
| 1-189583 | 7/1989 | Japan . |
| 2-290529 | 11/1990 | Japan . |
| 9-145691 | 6/1997 | Japan . |

OTHER PUBLICATIONS

Article entitled "Measurement of the Hardness of a Soft Material with a Piezoelectric Vibrometer and their Analysis" By Sadao Omata, Published in Medical Electronics & Bio–Engineering, vol. 28, No. 1 (1990), pp. 1–8.

Article entitled "New Type Tactile Sensor for Sensing Hardness like the Human Hand and its Applications for Living Tissue" By Sadao Omata, Published in Technical Digest of the 9th Sensor Symposium, 1990, pp. 257–260.

Article entitled "A Method for Clinically Measuring the the Hardness of a Living Body" By Osamu Takaya and Takao Akatsuka, Published in Measurement & Control, vol. 14, No. 3 (1975), pp. 281 to 292.

Article entitled "A Flexible High Resolution Tactile Imager with Video Signal Output" By Makoto Shimojo, et al, Published in Japan Mechanical Society Paper Collection, vol. 57, No. 537, pp. 1568–1573 (1991–5).

Article entitled "Improvement of a Flexible Sensor with Pressure–Sensitive Rubber" By Naoki Shinozaki, et al, Published in J. Jpn. Soc, Stomatognathic Function vol. 2, pp. 57–63, 1995.

Article entitled "Medical Application of Micromachine Technology" By Yasuhiro Ueda, Published in Precision Engineering Society Journal, vol. 62, No. 3, 1996, pp. 368–372.

*Primary Examiner*—Cary O'Connor
*Assistant Examiner*—Charles Marmor, II
*Attorney, Agent, or Firm*—Frishauf, Holtz, Goodman, Langer & Chick

[57] ABSTRACT

An endoceliac physical quantity measuring apparatus comprises a contact adapted to touch an organic tissue, a vibrator connected mechanically to the contact, a frequency characteristic detecting circuit for detecting parameters associated with the frequency characteristics of the vibrator, load detecting means for detecting a load acting between the organic tissue and the contact, arithmetic means for computing physical quantities of the organic tissue on the basis of the parameters associated with the frequency characteristics detected by the frequency characteristic detecting circuit and the load detected by the load detecting means, and presentation means for presenting the physical quantities computed by the arithmetic means.

27 Claims, 29 Drawing Sheets

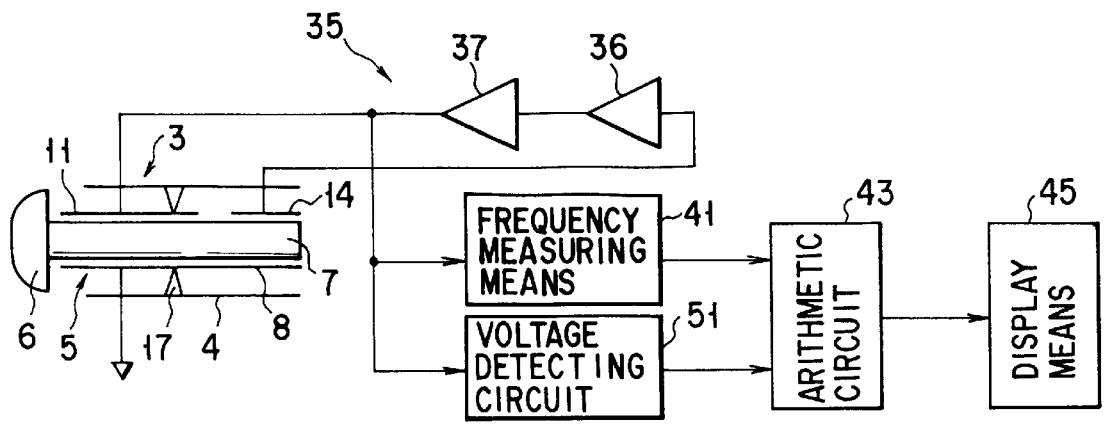
F I G. 5
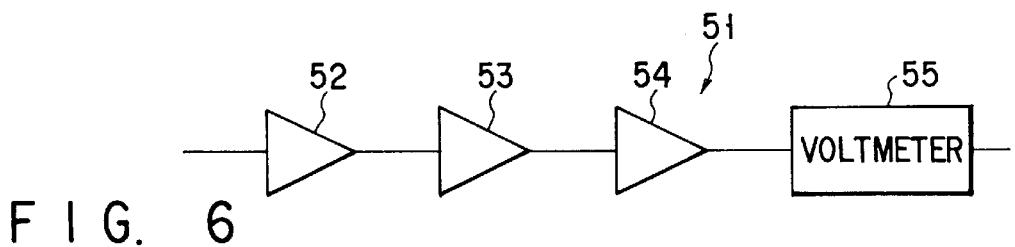
F I G. 6
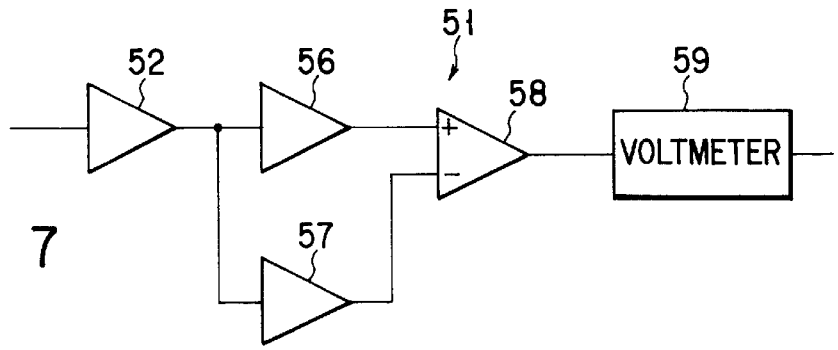
F I G. 7
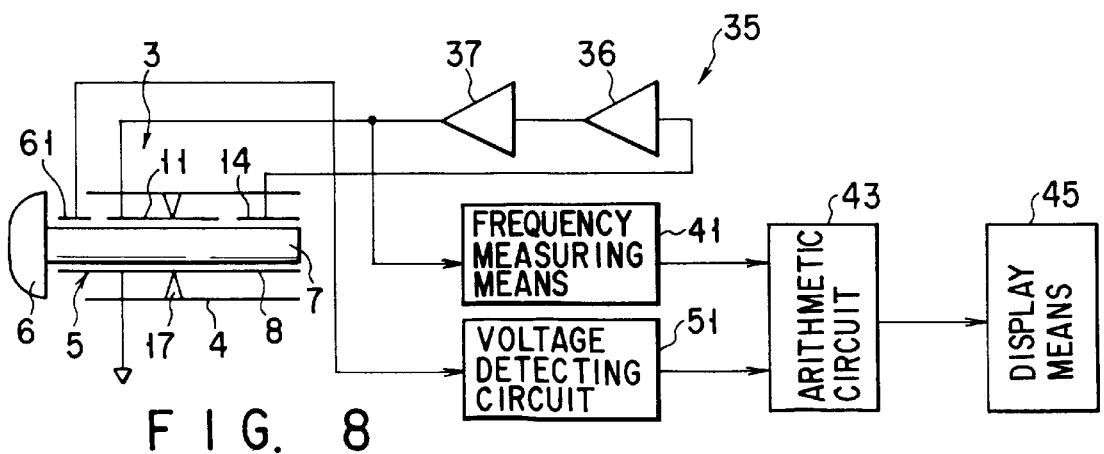
F I G. 8

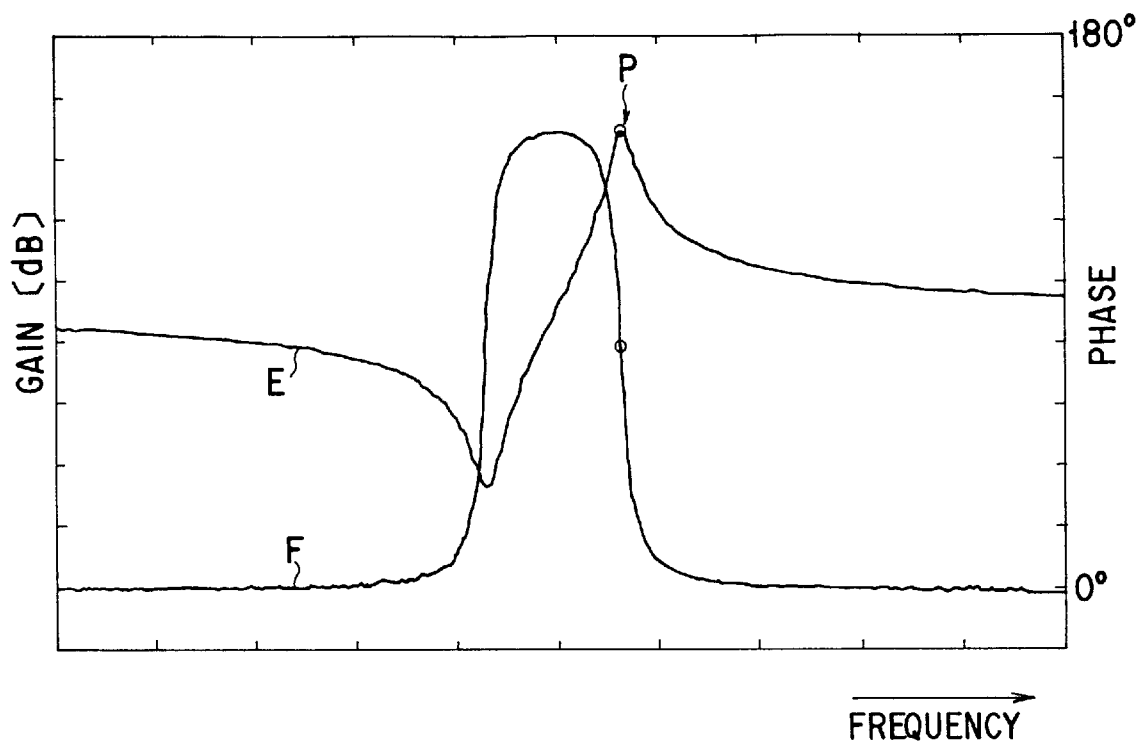
F I G. 13
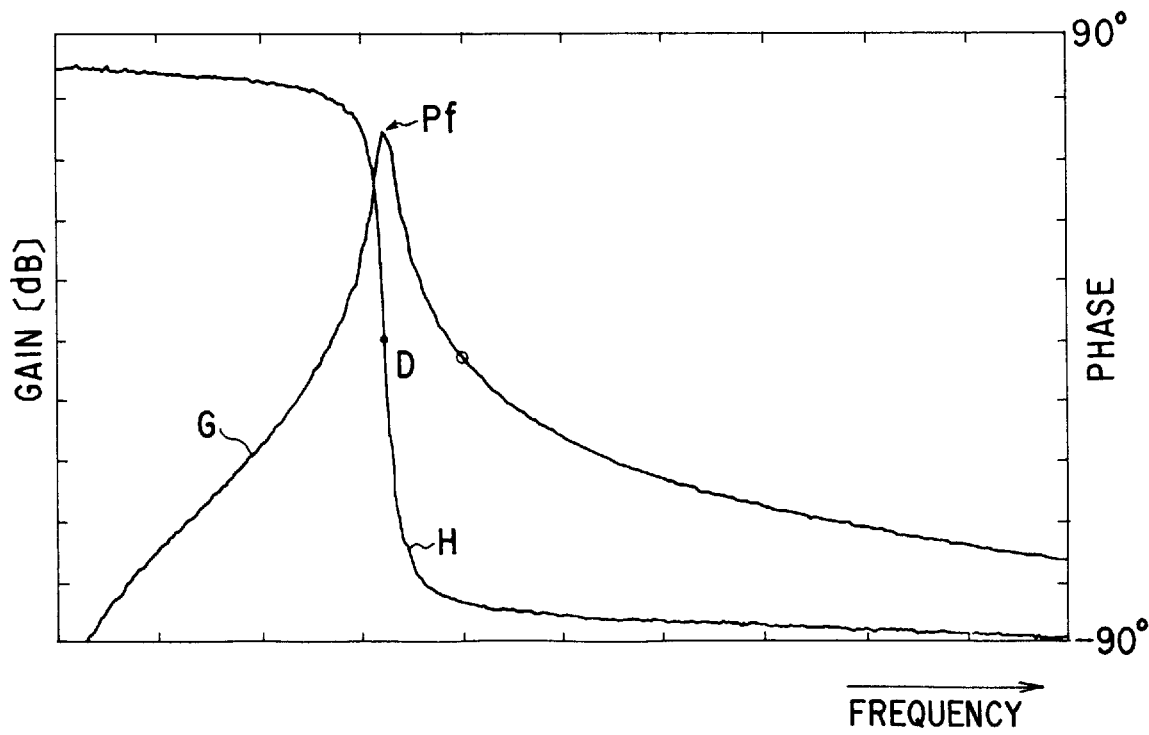
F I G. 14

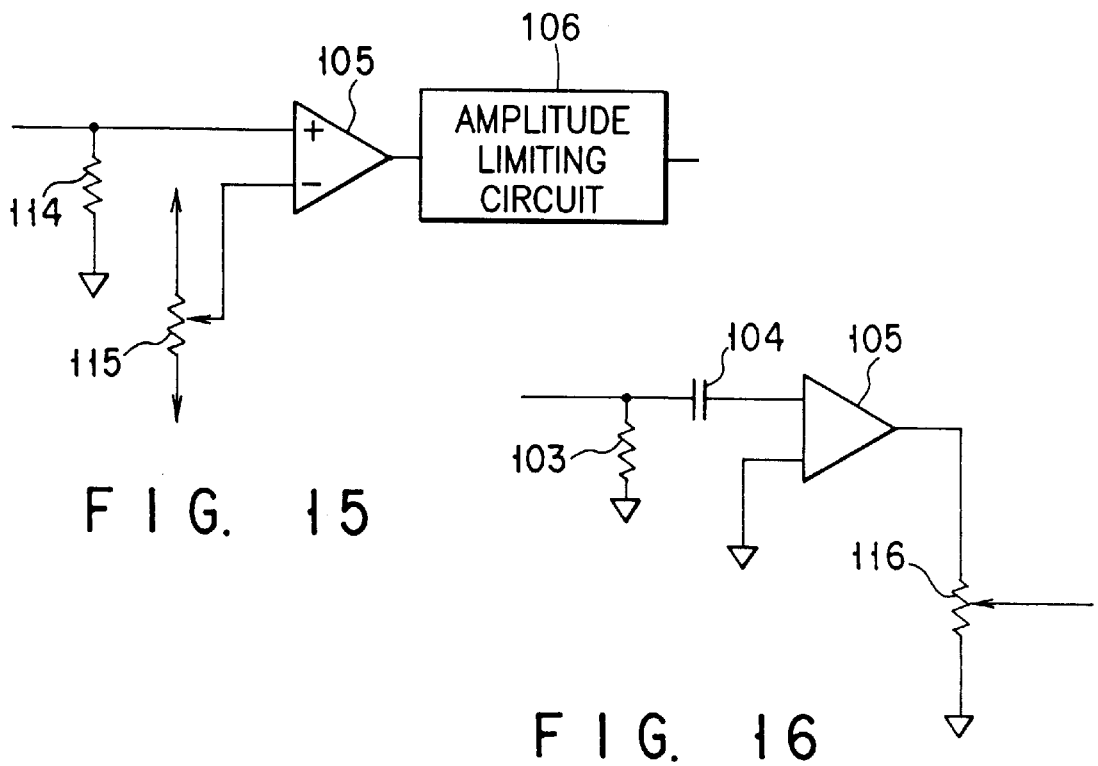
FIG. 15
FIG. 16
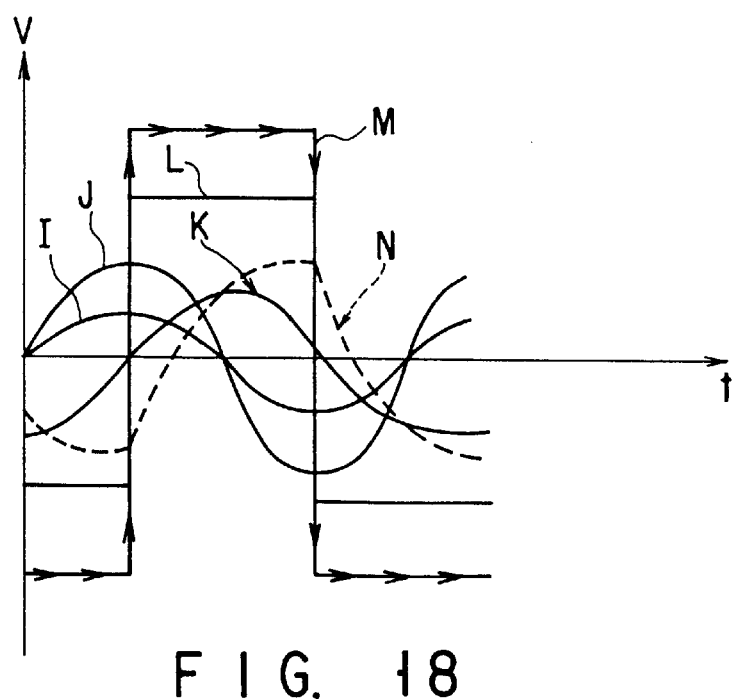
FIG. 18

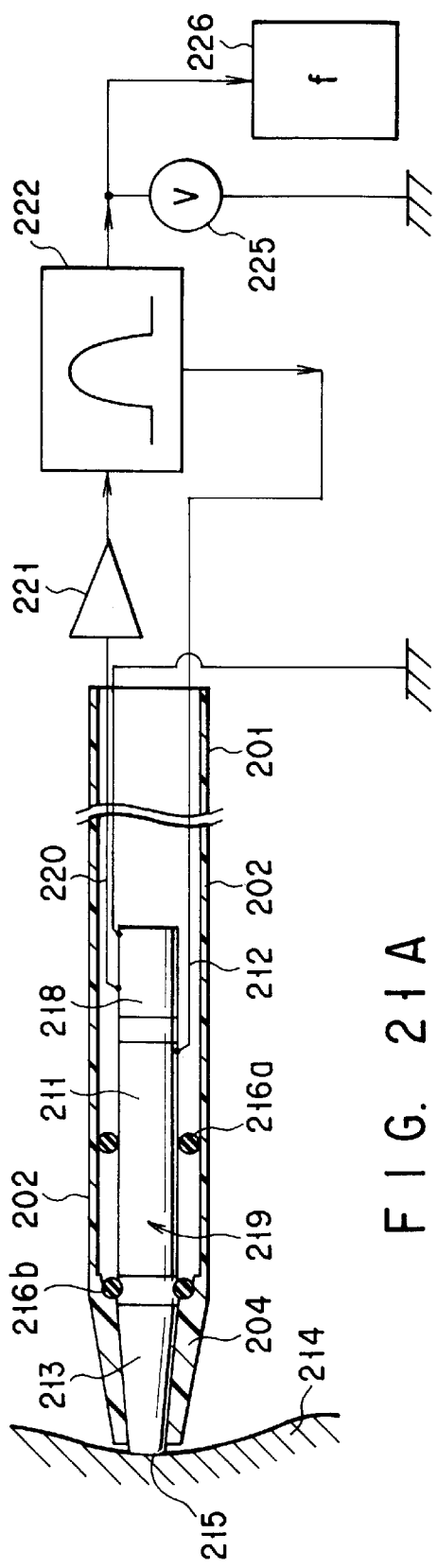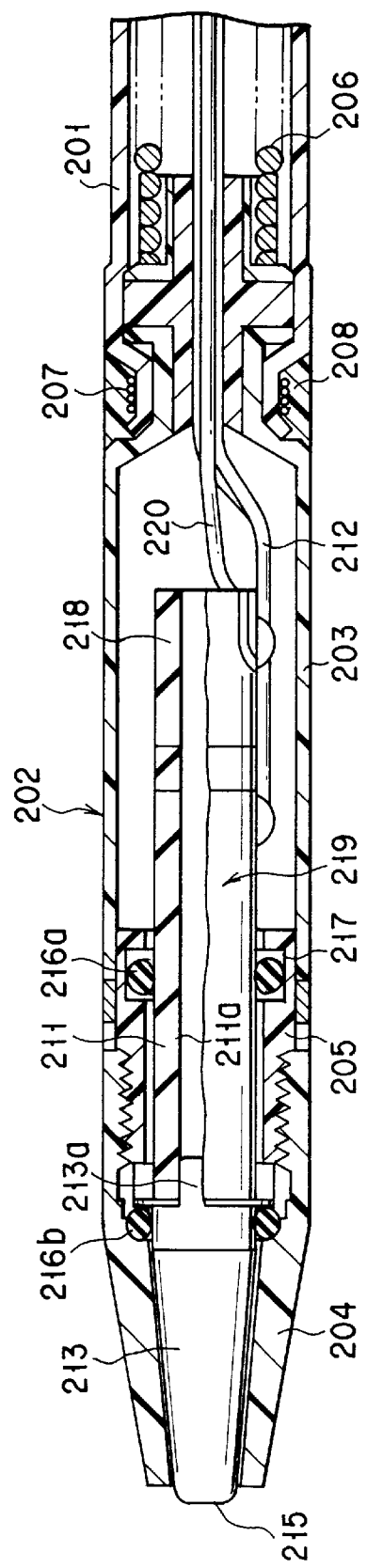
FIG. 21A
FIG. 21B

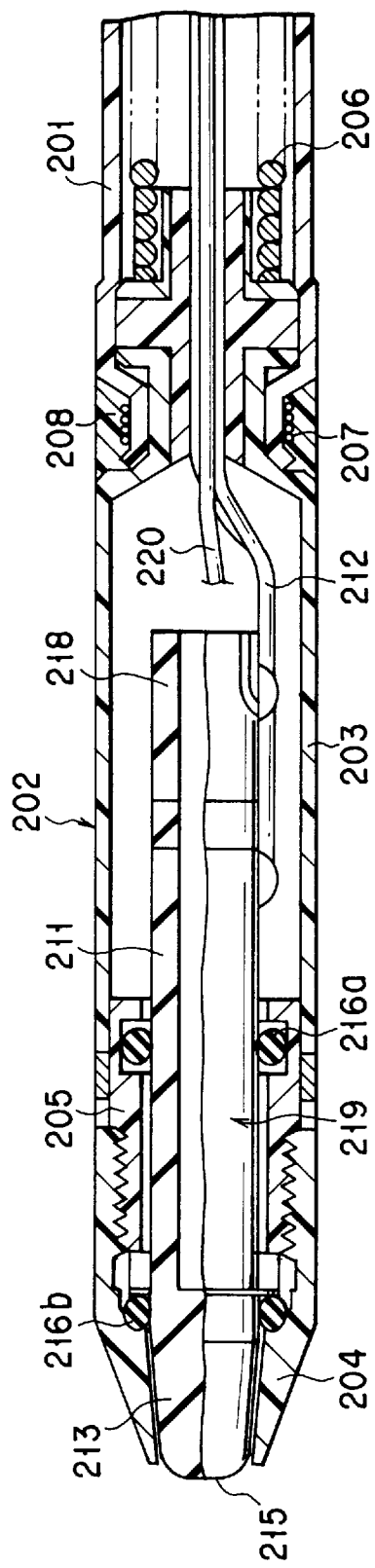
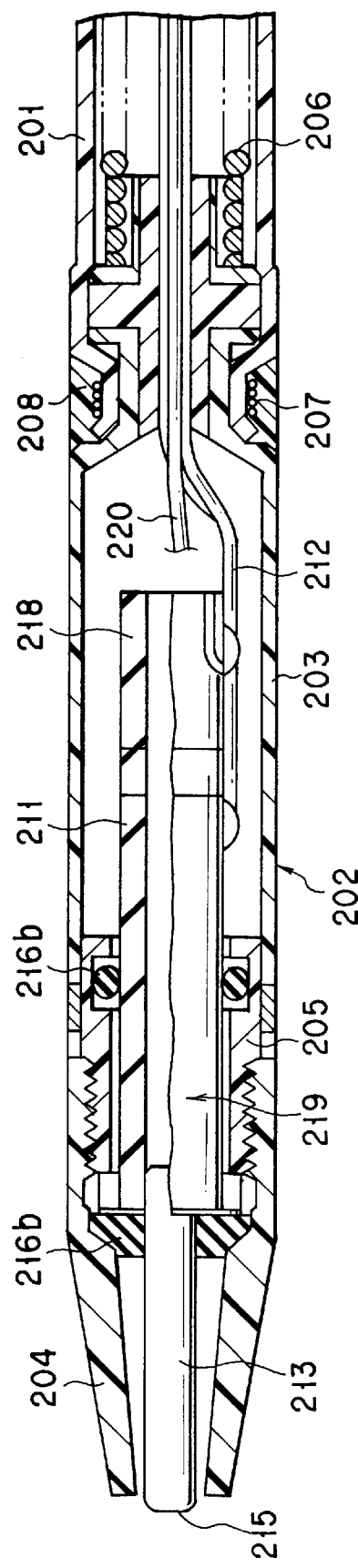
F I G. 22
F I G. 23

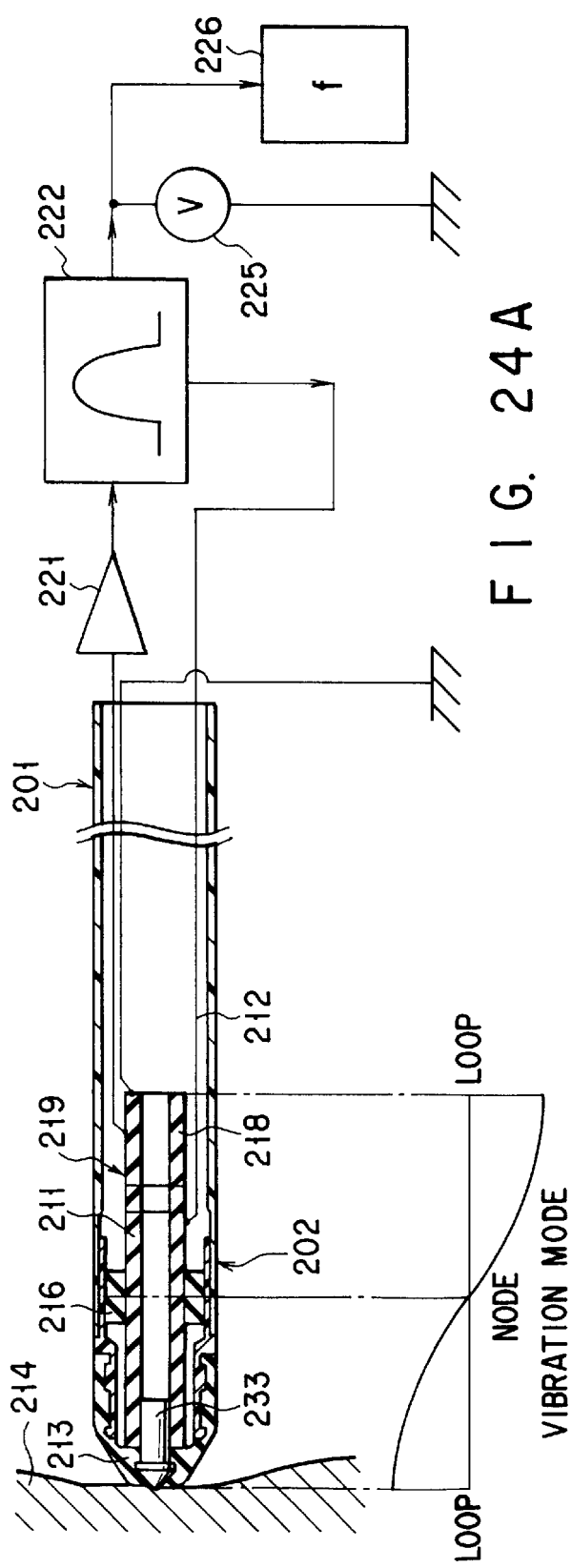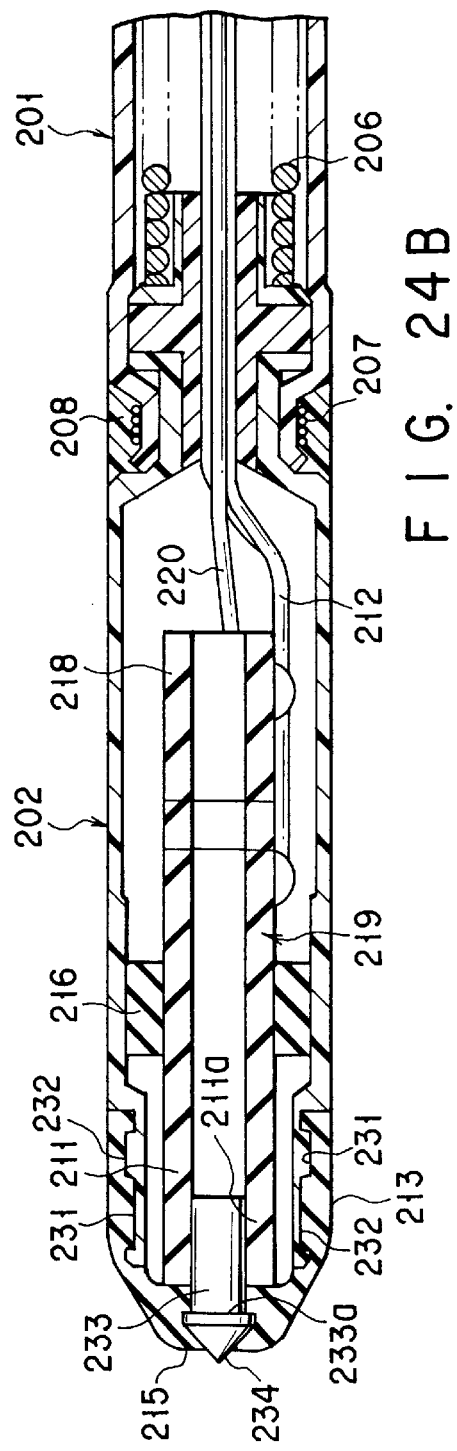

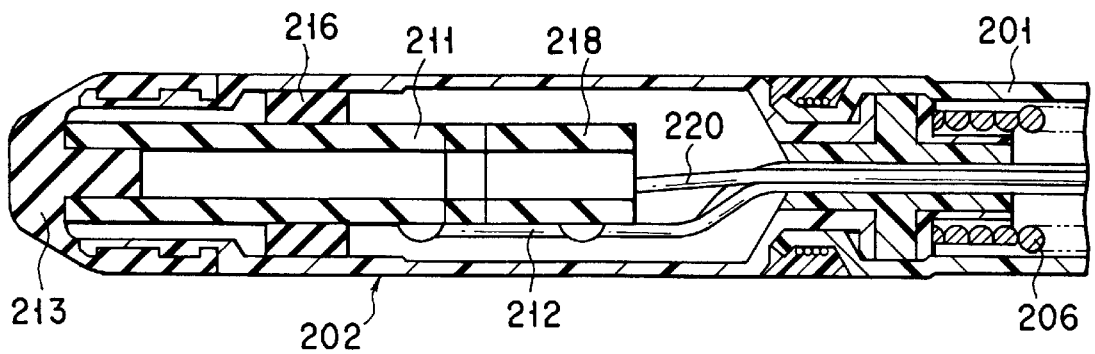
F I G. 26
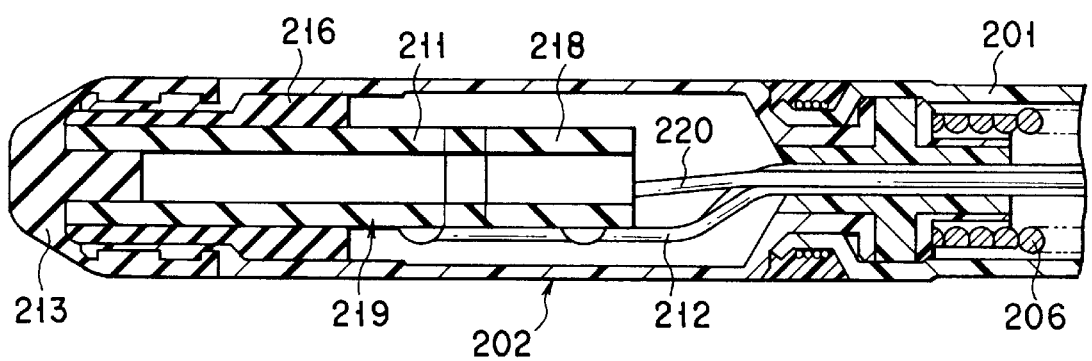
F I G. 27
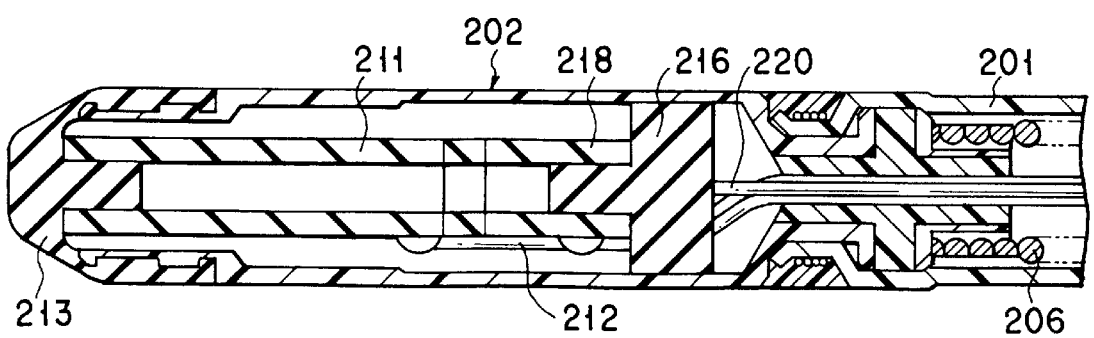
F I G. 28

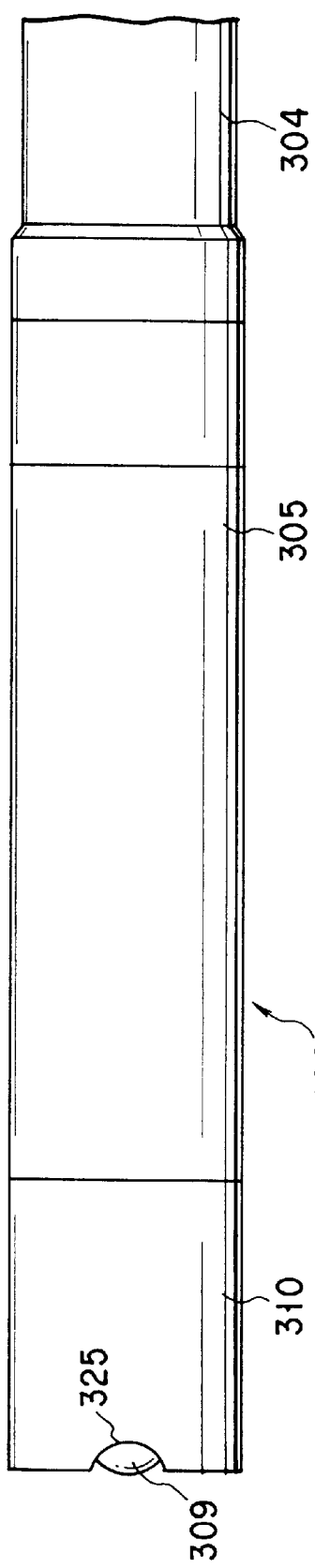
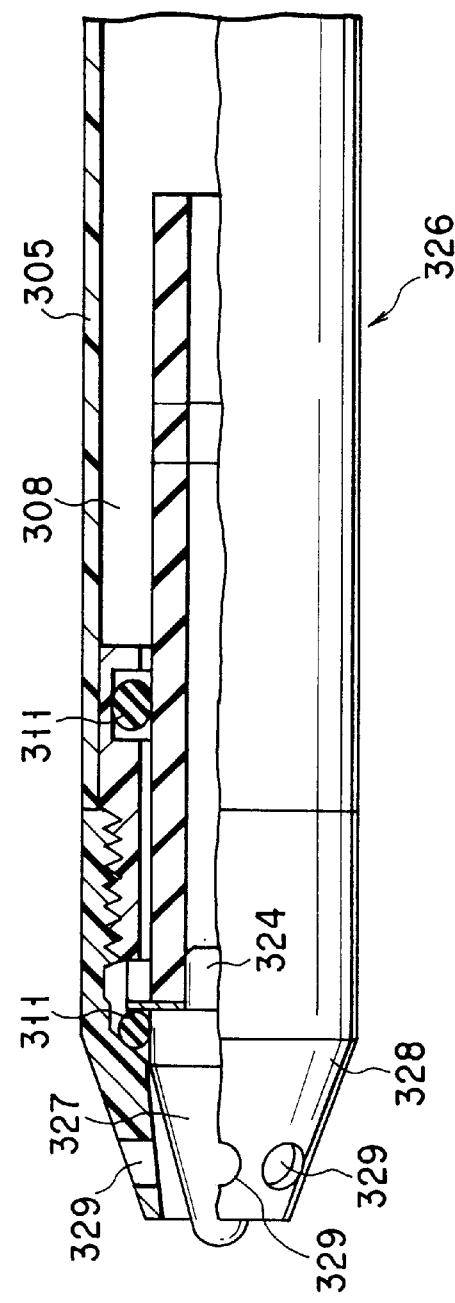
F I G. 31
F I G. 32

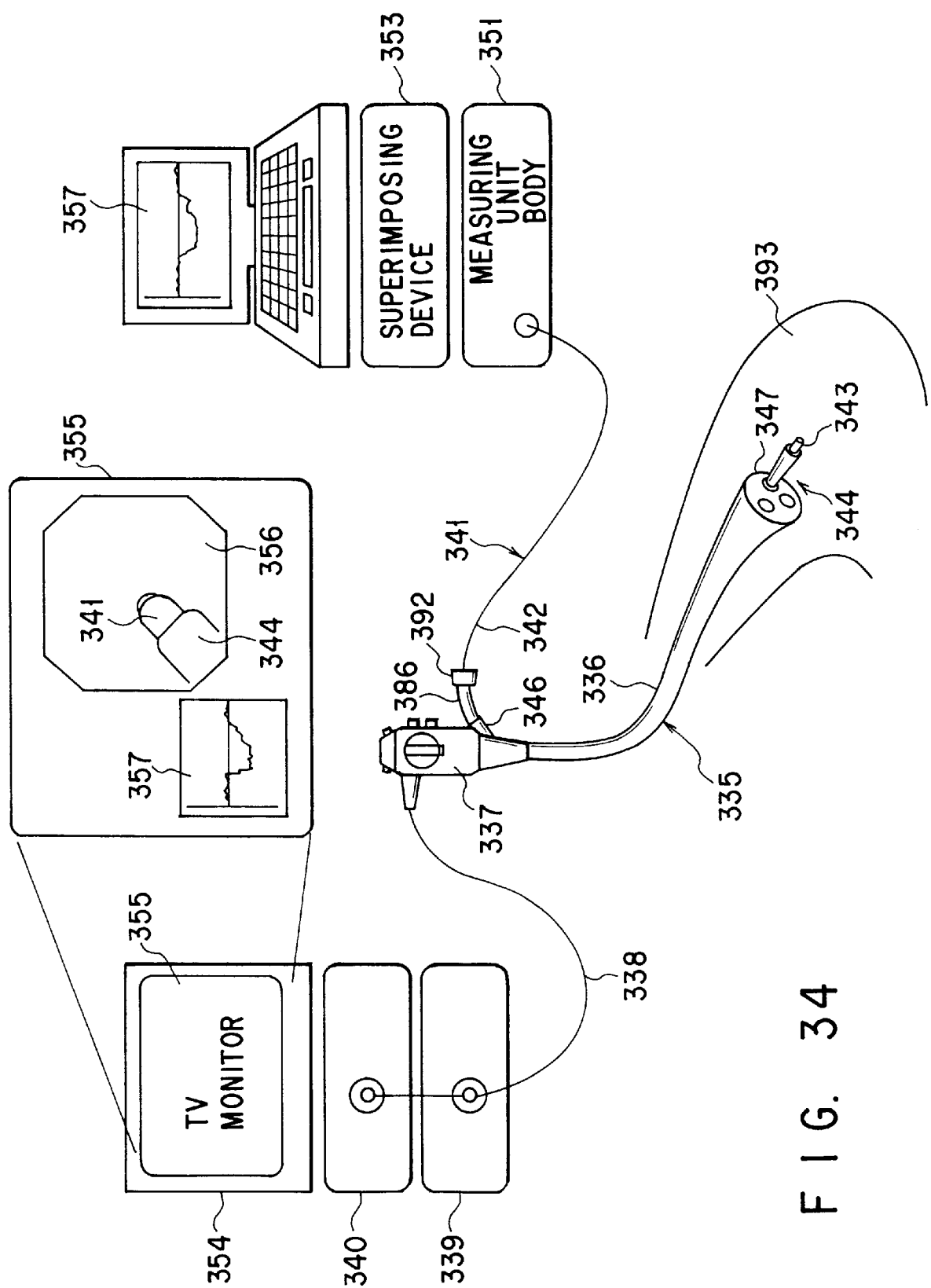
F I G. 34

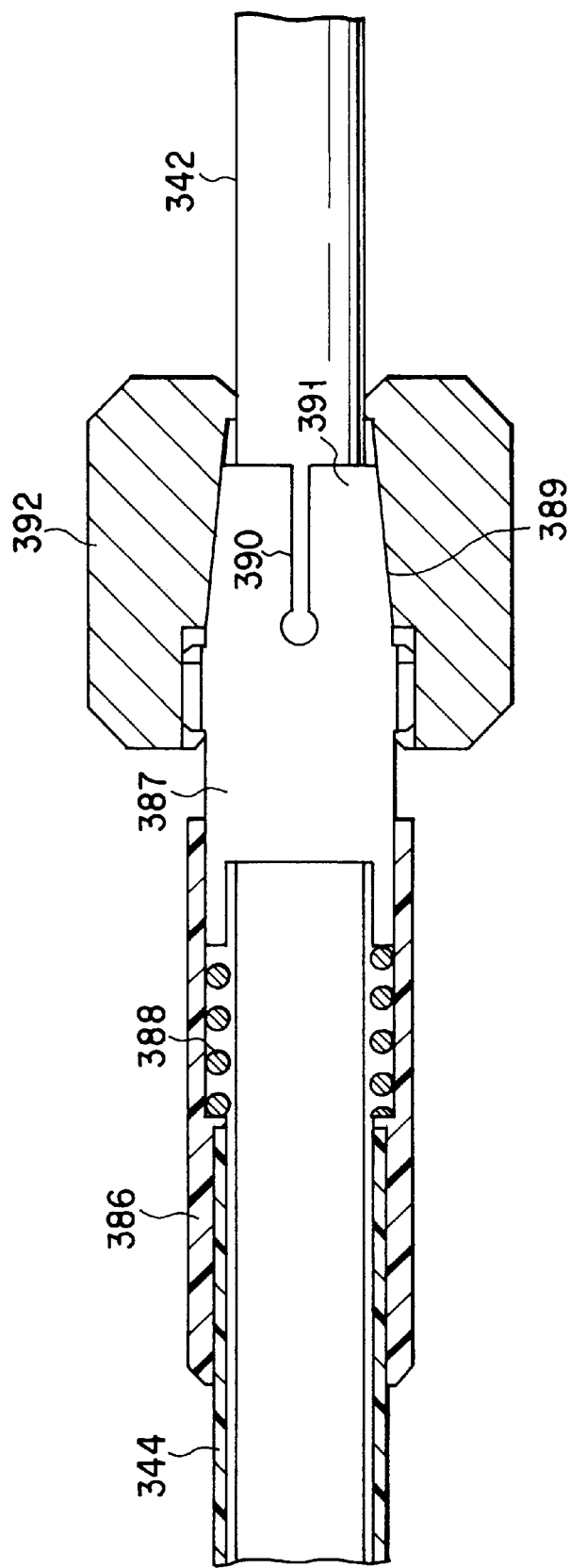
F I G. 36

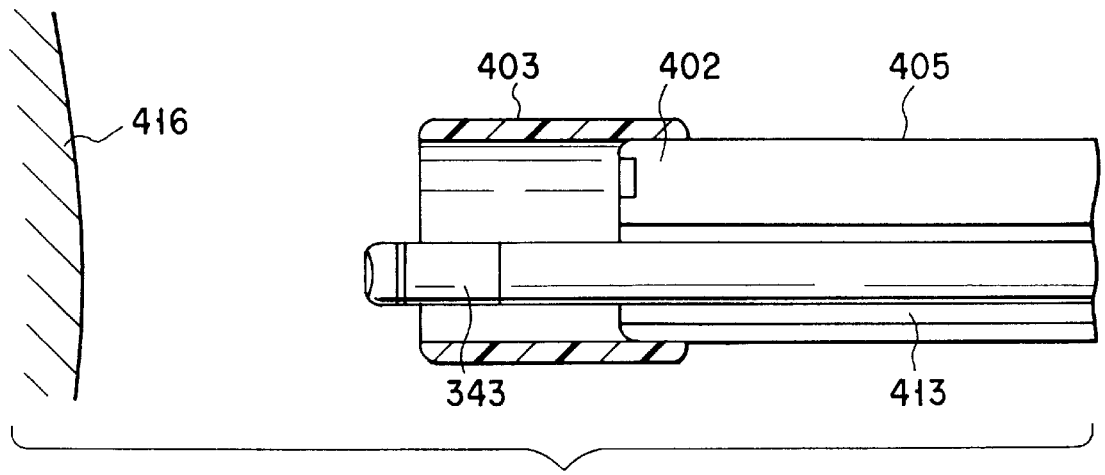
F I G. 40A
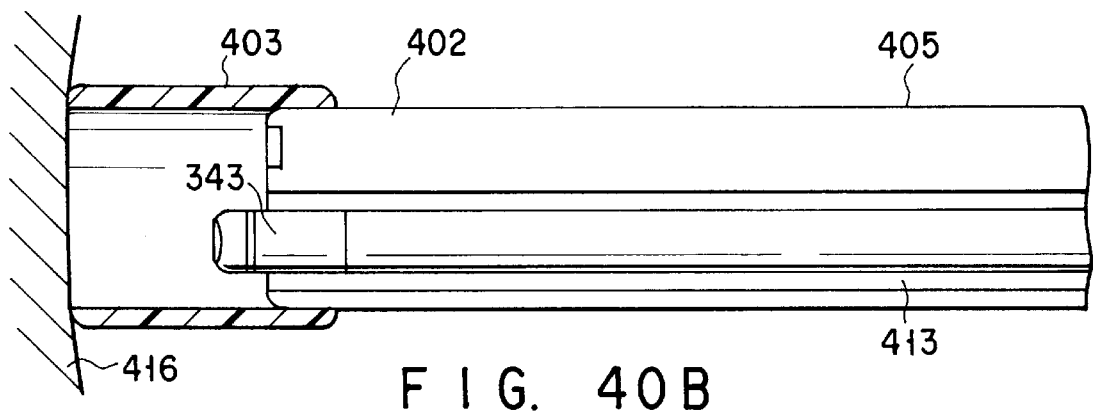
F I G. 40B
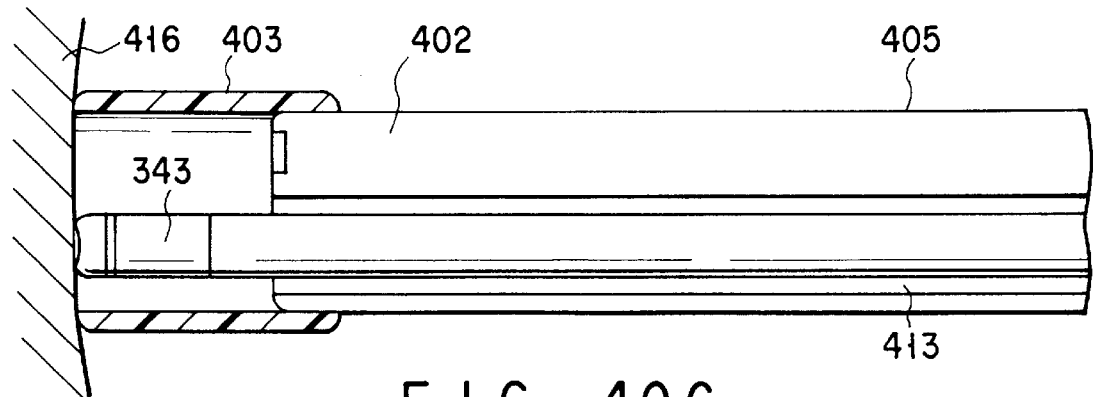
F I G. 40C

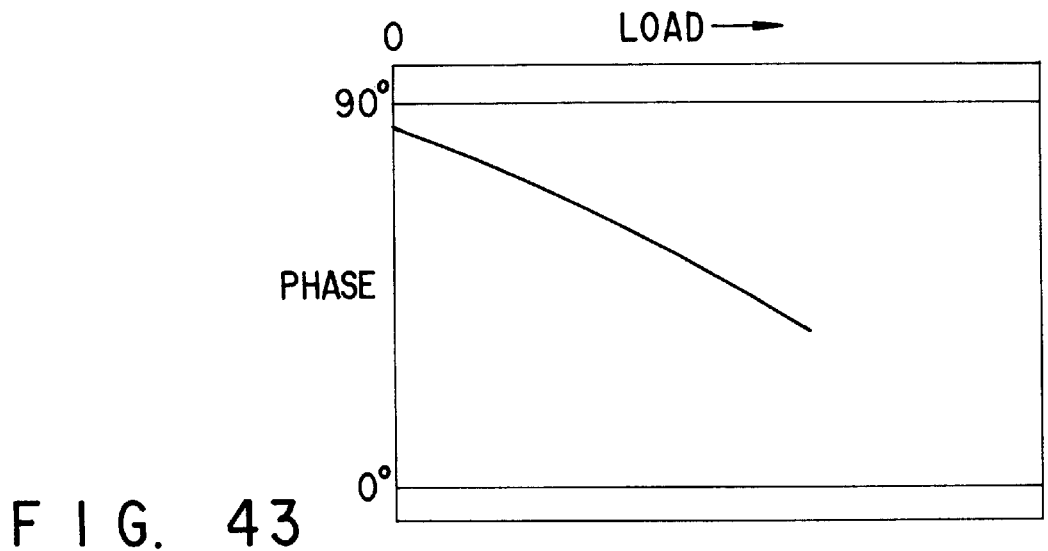
F I G. 43
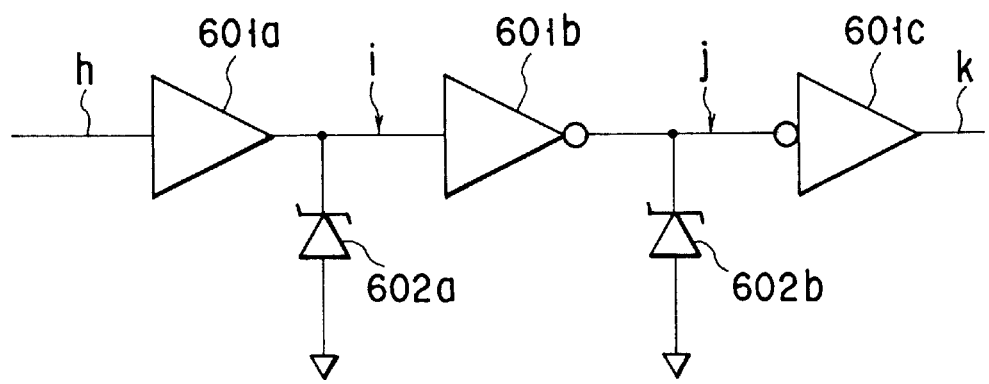
F I G. 44A
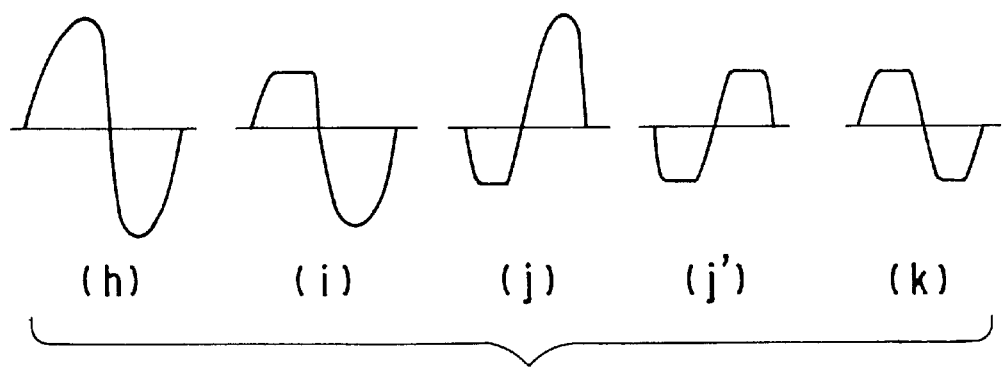
F I G. 44B

ENDOCELIAC PHYSICAL QUANTITY MEASURING APPARATUS HAVING EXCELLENT MEASURING RESOLUTION

BACKGROUND OF THE INVENTION

The present invention relates to an endoceliac physical quantity measuring apparatus for detecting a change in a resonance state caused when an organic tissue as an object of measurement is touched by a body vibrating in a resonant state, and for determining physical quantities of the tissue based on the change.

Endoceliac physical quantity measuring apparatuses are described in, for example, Jpn. Pat. Appln. KOKOKU Publication No. 40-27236, Jpn. Pat. Appln. KOKAI Publication Nos. 1-189583 and 2-290529, etc.

In these conventional measuring apparatuses, a vibration system that includes a contact to be made to touch an organic tissue and a vibrator connected mechanically to the contact is caused to resonate by means of a self-oscillation circuit based on a feedback loop. The impedance of the organic tissue obtained when the tissue is touched by the vibrator or contact is grasped as a change in the oscillation frequency of the self-oscillation circuit or a change in voltage, whereby information on physical quantities of the tissue is obtained. Parameters associated with the physical quantities include elasticity, density, viscosity, etc.

The apparatus described in Jpn. Pat. Appln. KOKOKU Publication No. 40-27236 further comprises a horn member, which is located between the vibrator and the contact in order to magnify a vibrating amplitude. Also described in this publication is an apparatus that measures the softness of a substance at the distal end of a metal needle, especially an organic tissue, in the following manner. Ultrasonic vibration energy from an ultrasonic oscillator is given to the metal needle through an electroacoustic transducer, a change in mechanical load compared with ultrasonic vibration at the distal end of the needle is fetched as a change in the acoustic impedance of the transducer, and the change in the acoustic impedance is measured.

Another endoceliac physical quantity measuring apparatus is described in Jpn. Pat. Appln. Publication No. 7-241869. In this apparatus, a piezoelectric vibrator having a contact to be caused to touch an organic tissue is provided with an exciting electrode and a feedback electrode. The vibrator is caused to resonate by returning an output from the feedback electrode to the exciting electrode through a band-pass filter that has a band-pass frequency lower than the resonance frequency of the vibrator with the organic tissue untouched, or in unloaded state. Then, physical quantities of the organic tissue are obtained by detecting a change in the resonance frequency caused when the tissue is touched by the contact. When the contact touches a soft object such as an organic tissue, in general, the impedance of the vibrator increases with its resonance frequency going down, so that the output of the feedback electrode lowers. The band-pass filter passes the lowered frequency output from the feedback electrode with quarter amplitude, so that the voltage returned to the exciting electrode increases. Thus, the resonant state of the vibrator can be maintained despite the increase of the impedance, so that the physical quantities can be measured covering a wide range. The physical quantities of the organic tissue can be also obtained by detecting a change in the voltage applied to the exciting electrode.

According to the conventional endoceliac physical quantity measuring apparatuses, moreover, the vibration system that includes the vibrator to be made to touch an organic tissue is formed from a metallic material adapted for high acoustic velocity, in order to enhance the effect of vibration transmission. Also, a casing member covering the vibration system is supported by means of an elastic member so that vibration is prevented from being transmitted to the casing member.

These endoceliac physical quantity measuring apparatuses have advantages in enjoying quantitative measurement of physical quantities of organic tissues by means of a non-destructive electrical measurement that requires only a short time. On account of these advantages, the apparatuses of this type are expected to be used as tactile sensors for the measurement of the elasticity of the human body's skin or for industrial robots.

According to the conventional endoceliac physical quantity measuring apparatuses, however, a physical quantity of an organic tissue obtained when the tissue is touched by the piezoelectric vibrator or the contact connected mechanically thereto is grasped as a change in the oscillation frequency of the self-oscillation circuit or a change in voltage, whereby information on the physical quantity of the tissue is obtained. In detecting differences between physical quantities of a soft object such as an organic tissue, especially a very soft internal tissue such as the inner wall of the stomach or esophagus, therefore, the resolution is so low that measurement data are subject to substantial dispersion. Further, the outputs of the measuring apparatuses are influenced considerably by the contact load between the organic tissue and the contact, so that the accuracy of the measurement is lowered.

For example, the amplitude of a feedback signal from the feedback electrode of the apparatus described in Jpn. Pat. Appln. Publication No. 7-241869 is subject to the influence of dispersion according to individual vibrators. In detecting the change of the voltage applied to the exciting electrode, moreover, the bandpass filter's Q-factor must be high enough to allow the reduced amplitude of the feedback signal to be augmented by increasing the gain. In consequence, it is difficult to adjust the respective frequency characteristics of the band-pass filter and the piezoelectric vibrator to one another.

In the prior art endoceliac physical quantity measuring apparatuses described above, furthermore, the impedance of the organic tissue as the object of measurement is considerably lower than the vibration energy of the vibrator, so that the variation of the oscillation frequency or voltage caused as the tissue is touched by the vibrator is much smaller than that obtained before the touch. Technically, therefore, it is very difficult to fetch electrically the variation of the oscillation frequency or voltage that is attributable to the touch on the organic tissue. Even if the variation can be fetched, the resulting data includes a lot of noises and lacks reliability. In general, for these reasons, it is hard to make high-accuracy measurements using these conventional measuring apparatuses In the above described measuring apparatus that has the horn member interposed between the vibrator and the contact to augment the amplitude of vibration of the contact, to thereby ensure high-accuracy measurements, the vibrator, horn member, and contact are arranged in a straight line. Accordingly, the apparatus has so long an overall length that its operability is poor, and requires use of many components that result in a high cost.

According to the conventional endoceliac physical quantity measuring apparatuses, moreover, the casing member that covers the vibration system is supported by means of the elastic member, so that the apparatuses have problems including complicated construction, low assembly performance, and poor operability attributable to its large outside diameter. In the case the apparatus is inserted into a patient's body through an endoscope to measure physical quantities of an organic tissue for diagnostic purposes, in particular, the endoscope used is expected to have a large diameter, which inevitably inflicts pain on the patient.

In the conventional endoceliac physical quantity measuring apparatuses described above, furthermore, the detected change of the impedance is greatly influenced by the load or angle of engagement under or at which the vibrator, for use as an electroacoustic transducer to be directly in touch with an organic tissue, or the contact, as a vibration transmitting member for guiding the vibration of the transducer to the tissue, touches the tissue.

Thus, accurate measurements of physical quantities require skilled operation. In the case where the object of measurement is a soft structure, such as an organic tissue, in particular, measurement data are subject to substantial dispersion, and it is very hard to make reliable measurements with high reproducibility.

BRIEF SUMMARY OF THE INVENTION

Accordingly, a first object of the present invention is to provide an endoceliac physical quantity measuring apparatus which is capable of measuring physical quantities of a soft object of measurement, such as an organic tissue, with improved resolution.

A second object of the invention is to provide an endoceliac physical quantity measuring apparatus which is capable of facilitating an adjustment operation in order to ensure enhanced detecting capability with greater output change.

A third object of the invention is to provide an endoceliac physical quantity measuring apparatus which is capable of measuring physical quantities of an organic tissue with high accuracy, which has a relatively simple, easy to manufacture, low-priced construction which has improved operability and a reduced size, and which inflicts less pain on a patient even in endoscopic use.

A fourth object of the invention is to provide an endoceliac physical quantity measuring apparatus which is capable of measuring physical quantities of a soft object of measurement, such as an organic tissue, with ease and reliability.

In order to achieve the first object described above, an endoceliac physical quantity measuring apparatus in an aspect of the invention comprises: a contact adapted to touch an organic tissue; a vibrator connected mechanically to the contact; a frequency characteristic detecting circuit for detecting parameters associated with the frequency characteristics of the vibrator; load detecting means for detecting a load acting between the organic tissue and the contact; arithmetic means for computing physical quantities of the organic tissue on the basis of the parameters associated with the frequency characteristics detected by the frequency characteristic detecting circuit and the load detected by the load detecting means; and presentation means for presenting the physical quantities computed by the arithmetic means.

In order to achieve the second object described above, moreover, an endoceliac physical quantity measuring apparatus in another aspect of the invention further comprises binary-coding means for binary-coding a feedback signal from the vibrator and feeding back the obtained binary-coded signal to the vibrator.

In order to achieve the third object described above, moreover, an endoceliac physical quantity measuring apparatus in still another aspect of the invention comprises a mechanical vibration unit having a shape with a sectional area reduced in the direction of propagation of vibration; a self-oscillation circuit for vibrating the mechanical vibration unit in a resonant state; and measuring means for measuring physical quantities of an organic tissue in accordance with change information on a resonance state obtained when the organic tissue is touched by the mechanical vibration unit.

In order to achieve the fourth object described above, furthermore, an endoceliac physical quantity measuring apparatus in a further aspect of the invention further comprises a mechanical vibration unit including a contact adapted to touch an organic tissue and an electroacoustic transducer; a fixing member attached to peripheral portion of the contact of the mechanical vibration unit; and measuring means for obtaining change information on the state of the contact when the organic tissue is touched by the contact, thereby measuring physical quantities of the organic tissue.

Additional object and advantages of the invention will be set forth in the description which follows, and in part will be obvious from the description, or may be learned by practice of the invention The object and advantages of the invention may be realized and obtained by means of the instrumentalities and combinations particularly pointed out in the appended claims

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 5 is a block diagram showing an endoceliac physical quantity measuring apparatus composed of a physical quantity sensor unit and a physical quantity measuring system according to a sixth embodiment of the invention;

FIG. 6 is a block diagram showing a configuration of a voltage detecting circuit according to the sixth embodiment;

FIG. 7 is a block diagram showing a configuration of a voltage detecting circuit according to a seventh embodiment of the invention;

FIG. 8 is a block diagram showing an endoceliac physical quantity measuring apparatus composed of a physical quantity sensor unit and a physical quantity measuring system according to an eighth embodiment of the invention;

FIG. 13 is a diagram showing phase and gain characteristics of a piezoelectric vibrator;

FIG. 14 is a diagram showing phase and gain characteristics of a band-pass filter;

FIG. 15 is a diagram partially showing an arrangement of an endoceliac physical quantity measuring apparatus according to a twelfth embodiment of the invention;

FIG. 16 is a diagram partially showing an arrangement of an endoceliac physical quantity measuring apparatus according to a thirteenth embodiment of the invention;

FIG. 18 is a diagram showing the states of signals at individual nodes of the apparatus of FIG. 17;

FIG. 21A is a schematic view for illustrating an endoceliac physical quantity measuring apparatus according to a sixteenth embodiment of the invention;

FIG. 21B is a longitudinal sectional view of the distal end portion of a physical quantity sensor unit shown in FIG. 21A;

FIG. 22 is a longitudinal sectional view of the distal end portion of a physical quantity sensor unit according to a seventeenth embodiment of the invention;

FIG. 23 is a longitudinal sectional view of the distal end portion of a physical quantity sensor unit according to an eighteenth embodiment of the invention;

FIG. 24A is a schematic view for illustrating a physical quantity sensor unit according to a nineteenth embodiment of the invention;

FIG. 24B is a longitudinal sectional view of the distal end portion of the sensor unit shown in FIG. 21A;

FIG. 26 is a longitudinal sectional view of the distal end portion of a physical quantity sensor unit according to a twentieth embodiment of the invention;

FIG. 27 is a longitudinal sectional view of the distal end portion of a physical quantity sensor unit according to a twenty-first embodiment of the invention;

FIG. 28 is a longitudinal sectional view of the distal end portion of a physical quantity sensor unit according to a twenty-second embodiment of the invention;

FIG. 31 is an exterior view showing an external appearance of the distal end portion of the sensor unit according to the twenty-third embodiment;

FIG. 32 is an exterior view, partially in section, showing the distal end structure of a physical quantity sensor unit according to a twenty-fourth embodiment of the invention;

FIG. 34 is a schematic view for illustrating an endoscopic-use arrangement of an endoceliac physical quantity measuring apparatus composed of a physical quantity sensor unit and a physical quantity measuring system according to a twenty-sixth embodiment of the invention;

FIG. 36 is a sectional view showing an arrangement of the handling-side portion of the sensor unit according to the twenty-sixth embodiment fitted with a fixing tube of the physical quantity sensor unit according to a fourth embodiment;

FIGS. 40A, 40B and 40C are diagrams for illustrating steps of procedure for operating the sensor unit according to the twenty-seventh embodiment;

FIG. 43 is a diagram showing a relation between load and phase;

FIGS. 44A and 44B are diagrams showing a twenty-ninth embodiment of the invention.

DETAILED DESCRIPTION OF THE INVENTION

Figure 1A:
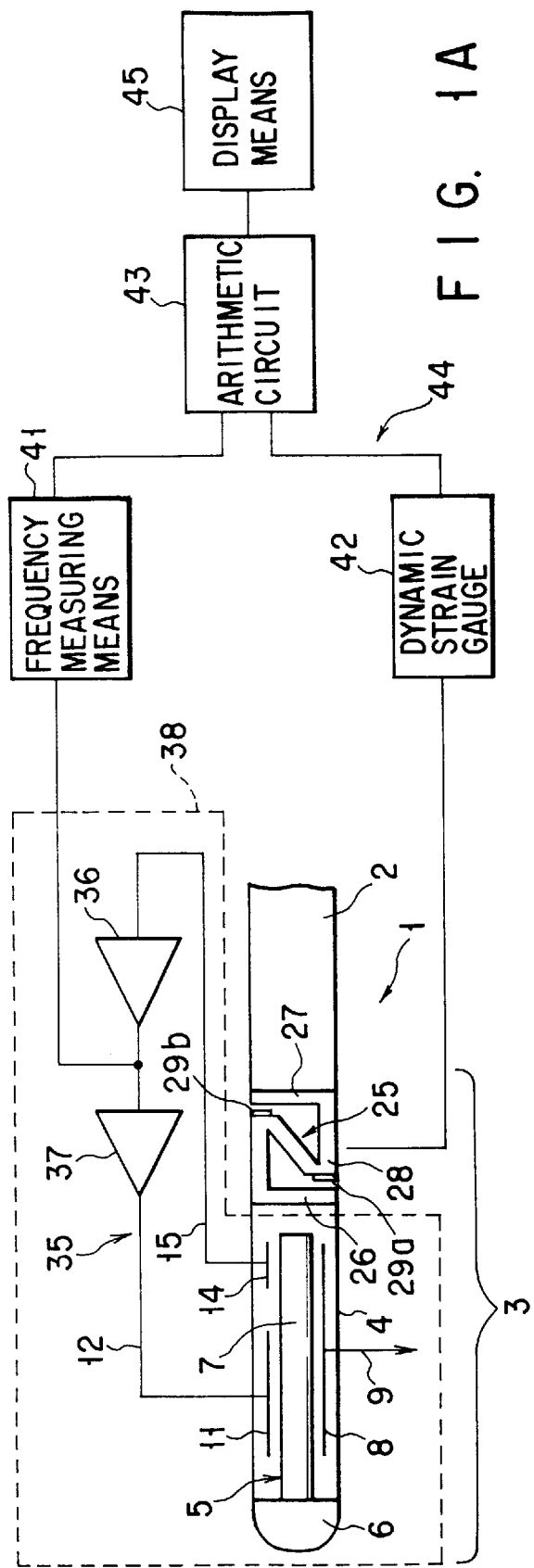
FIG. 1A is a block diagram showing an endoceliac physical quantity measuring apparatus composed of a physical quantity sensor unit and a physical quantity measuring system according to a first embodiment of the present invention.
Figure 1B:
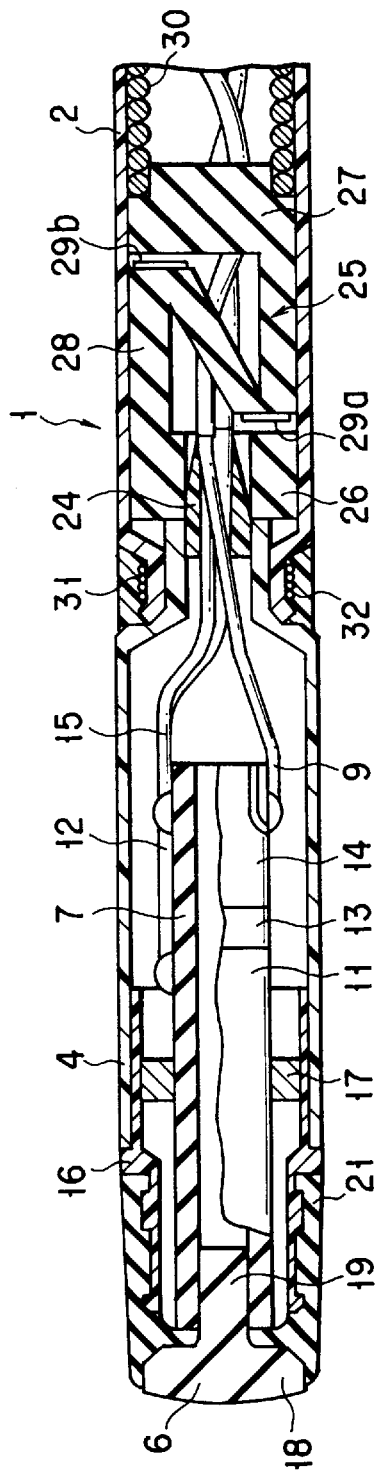
FIG. 1B is a sectional view showing the internal structure of the distal end portion of the sensor unit according to the first embodiment.
Figure 2:
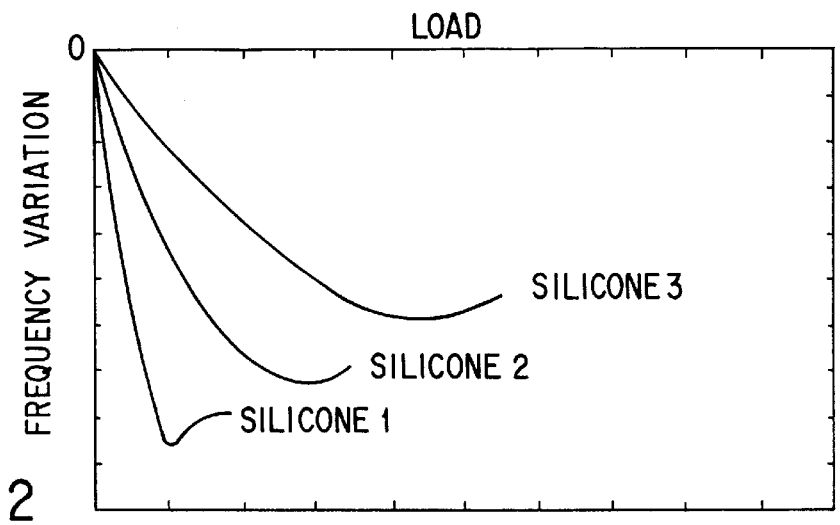
FIG. 2 is a graph showing relations between contact load and frequency change.
Figure 3:
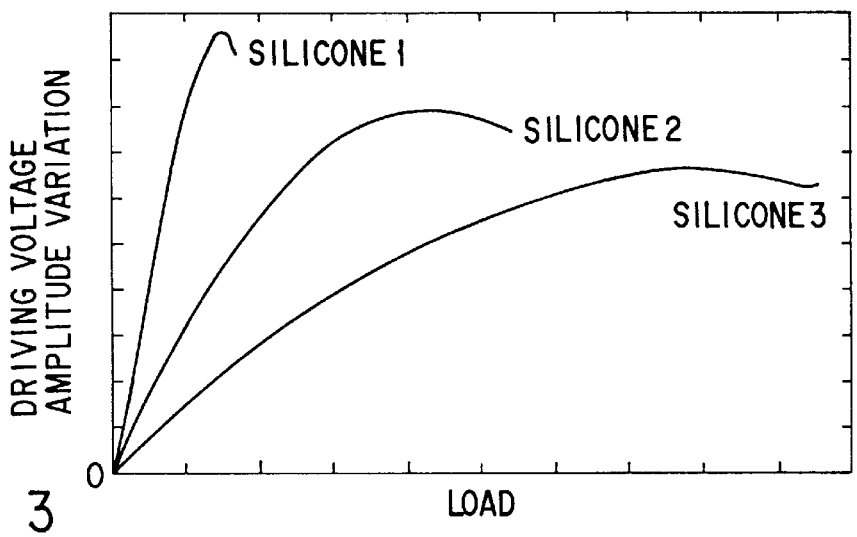
FIG. 3 is a graph showing relations between contact load and the resonance voltage amplitude of a driving electrode of an electroacoustic transducer.
Figure 4:
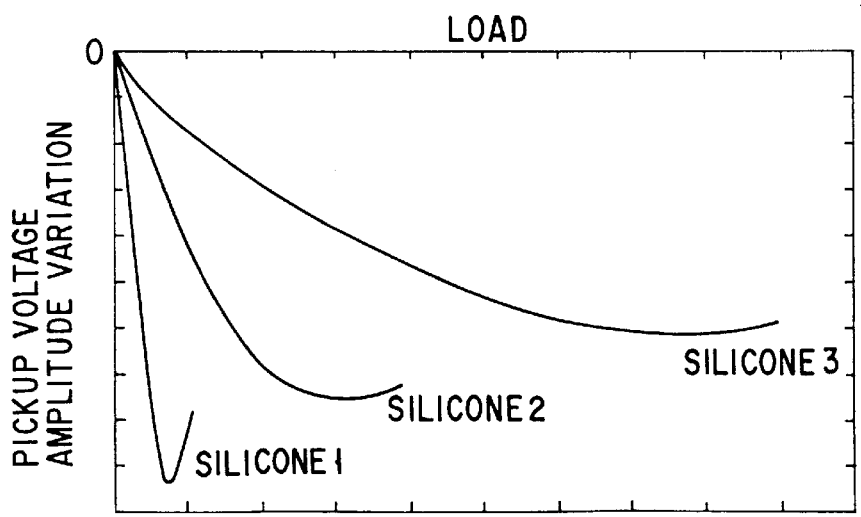
FIG. 4 is a graph showing relations between contact load and output voltage amplitude change in a detecting electrode of the electroacoustic transducer.

Referring first to FIGS. 1 to 4, a first embodiment of the present invention will be described. FIG. 1A is a block diagram showing an endoceliac physical quantity measuring apparatus composed of a physical quantity sensor unit and a physical quantity measuring system according to the present embodiment, and FIG. 1B is a sectional view showing the internal structure of the distal end portion of the physical quantity sensor unit according to the first embodiment. FIG. 2 is a graph showing relations between contact load and frequency change, FIG. 3 is a graph showing relations between contact load and resonance voltage amplitude change in a driving electrode of an electroacoustic transducer, and FIG. 4 is a graph showing relations between contact load and output voltage amplitude change in a detecting electrode of the electroacoustic transducer.

The following is a description of an arrangement of the first embodiment.

In FIG. 1, numeral 1 denotes a sensor probe. The probe 1 comprises a holding member 2 formed of an elongate flexible tube and a physical quantity sensor unit 3 attached to the distal end of the member 2. The sensor unit 3 is formed by coaxially incorporating an electroacoustic transducer 5 into a substantially cylindrical casing 4 and attaching a contact 6 to the distal end of the casing 4. The transducer 5 includes a piezoelectric vibrator 7 that is formed of a sintered cylindrical piezoelectric ceramic material, such as PZT, and is polarized in its radial direction. A metal film is formed on the inner peripheral surface of the vibrator 7, covering the overall length from the front end thereof to the rear end, and is used as a grounding electrode 8. A grounding conductor 9 is connected to the electrode 8 by soldering. The other end of the conductor 9 is connected to the ground level of the physical quantity measuring system. A driving electrode 11 of a metal film is formed on the outer peripheral surface of the vibrator 7, covering about ¾ of the overall length of its cylindrical portion from the front end thereof. A driving conductor 12 is connected to the electrode 11. That portion of the vibrator 7 which is covered by the electrode 11 constitutes a vibrating section.

Further, a detecting electrode 14 of a metal film is provided on the outer peripheral surface of the vibrator 7. The electrode 14 is situated nearer to the rear end of the vibrator 7 than the driving electrode 11 with a space 13 for insulation between the two electrodes 11 and 14. The detecting electrode 14 is connected with a signal conductor 15 that connects with the physical quantity measuring system. That portion of the vibrator 7 which is covered by the detecting electrode 14 constitutes a detecting section. Thus, the vibrator 7 is provided with the three electrodes 8, 11 and 14.

As shown in FIG. 1B, the vibrator 7 is held in a central position in the casing 4 by means of a ring-shaped fixing member 17 interposed between the vibrator 7 and the inner surface of a connecting ring 16 that doubles as a cover attached to the distal end portion of the casing 4. The fixing member 17 is located near a break in the vibration of the vibrator 7, so that the vibration of the vibrator 7 cannot be easily transmitted to the casing 4 for covering.

The distal end portion of the contact 6 constitutes a large-diameter contact portion 18, the distal end face of which forms a spherical contact surface to be held against an organic tissue. The proximal end portion of the contact 6 constitutes a columnar projection 19 that has an outside diameter a little smaller than the inside diameter of the cylindrical portion of the vibrator 7. The projection 19 is inserted tight in the cylindrical portion of the vibrator 7, and these two structures are bonded together. Thus, the electroacoustic transducer 5 and the contact 6 are connected mechanically integrally, so that the acoustic connection between them is firm. A stepped portion at the boundary between the large-diameter contact portion 18 and the small-diameter projection 19 of the contact 6 is finished with a radius grinding machine, the section radius of which varies smoothly. Accordingly, the vibration mode of the whole structure from the electroacoustic transducer 5 to the contact 6 is subject to only minor frequency noises.

The side peripheral surface of the distal end portion 18 of the contact 6 is covered by a cylindrical elastic member 21 that is formed of an elastic material such as polyurethane or silicone rubber. The elastic member 21 is fitted on the distal end portion of the connecting ring 16. The ring 16 is fixed to the casing 4 in a manner such that its proximal end portion is fitted in the distal end portion of the casing 4.

The physical quantity sensor unit 3 is provided with a force sensor 25 at the rear end of the casing 4. The sensor 25 constitutes load detecting means for detecting load that acts between the organic tissue and the contact 6. In the sensor 25, a Z-shaped elastic arm portion (elastic element) 28 is located between a front-end pillar portion 26 and a rear-end pillar portion 27. The two opposite ends of the arm portion 28 are connected to the pillar portions 26 and 27, individually, so that the sensor 25 is an integral structure. A plurality of strain gauges 29a and 29b formed of, for example, a semiconductor are bonded as detecting elements on those portions of the elastic arm portion 28 which are stressed intensively. When each of these gauges 29a and 29b is subjected to a stress, its resistance changes, whereby the applied force is detected.

The front-end pillar portion 26 of the force sensor 25 is fixed to the rear end of the casing 4, and the rear-end pillar portion 27 to the distal end of the holding member 2. The member 2 has a reinforcing core coil 30 therein. The distal end edge of the holding member 2 is fitted on the rear end of the casing 4, fastened with a piece of string 31, and fixed with an adhesive 32. The sensor 25 is covered liquid-tight by the casing 4 and the holding member 2.

The grounding conductor 9, driving conductor 12, and signal conductor 15 are collectively guided to the holding member 2 through a hollow portion and side gaps of the force sensor 25. The rear end of the casing 4 and a hollow of the front-end pillar portion 26 form a soldering portion 24. In this case, the core of a coaxial cable is used for each of the conductors 12 and 15, and the shielding wire of the cable serves as the grounding conductor 9.

An output signal from the detecting section of the physical quantity sensor unit 3 is transmitted to the physical quantity measuring system 35 by means of the signal conductor 15, amplified by a power amplifier, e.g., an amplifier circuit 36, of the measuring system 35, and applied to the input of a filter circuit 37. The filter circuit 37 is a band-pass filter that has specific bandwidths of about 10% above and below the basic oscillation frequency of the electroacoustic transducer 5 and the contact 6 as its center frequency, for example. The band-pass frequency of the filter circuit 37 is adjusted to a frequency lower than the resonance frequency of the vibrator 7. The circuit 37 serves to remove noises from the output of the detecting section and prevent the transducer 5 from vibrating in an undesired high-order mode.

The output of the filter circuit 37 is amplified by means of a power amplifier (not shown), for example, and is supplied to the vibrating section by means of the driving conductor 12. The vibration of the vibrating section is detected again in the detecting section.

The above channels are connected so that the detected vibration output of the electroacoustic transducer 5 is positively fed back to the driving power of the transducer 5. Thus, the vibrating section and the detecting section of the transducer 5, amplifier circuit 36, and filter circuit 37 form a closed self-oscillation loop. A mechanical vibration system composed of the transducer 5 and the contact 6 constitutes a resonance circuit 38, which undergoes integral mechanical resonance vibration at a frequency such that the loop gain of the closed loop has its maximum.

On the other hand, the output end of the filter circuit 37 is connected with frequency measuring means 41, such as a frequency counter for detecting the resonance frequency, whereby the frequency of the operating self-oscillation circuit can be monitored. The measuring means 41 may be located in any position within the closed loop of the self-oscillation circuit.

Further, the output end of the force sensor 25 is connected with a dynamic strain gauge 42 for determining load acting on the contact 6 of the physical quantity sensor unit 3. During the measurement, the gauge 42 determines the load on the contact 6 by the output of the sensor 25.

An arithmetic circuit 43 constitutes a measuring section 44, which receives and computes the respective outputs of the frequency counter (frequency measuring means) 41 and the dynamic strain gauge 42, and converts them into physical quantity information on the organic tissue that touches the contact 6 of the physical quantity sensor unit 3. Measured physical quantity values computed in the arithmetic circuit 43 of the measuring section 44 are presented on presentation means. For example, the computation results are stored in a storage device or displayed on display means 45.

The following is a description of the operation of the arrangement described above.

The mechanical vibration system, which is composed of the electroacoustic transducer 5 and the contact 6, undergoes integral mechanical resonance vibration at a frequency such that the loop gain of the aforesaid closed loop has its maximum.

When an operator, having the holding member 2 in his hand, causes the organic tissue to touch the contact 6 of the physical quantity sensor unit 3, the resonance frequency of the vibrator 7 changes. As the organic tissue touches the contact 6, at the same time, a compressive force acts on the force sensor 25. The strain gauges 29a and 29b are deformed by this compressive force, and their resistances change. The change of the resistances of the gauges 29a and 29b is detected by the dynamic strain gauge 42. The arithmetic circuit 43 synchronously receives signals from the frequency counter 41 and the gauge 42.

The value of the signal from the frequency counter 41 obtained when the output of the dynamic strain gauge 42 takes a predetermined value (threshold value) is detected as a feature quantity indicative of a physical quantity of the organic tissue. The detected feature quantity may be numerically displayed intact on the display means 45. Alternatively, however, it may be converted in any suitable manner such that the converted value can be displayed in the form of, for example, a graph on the display means 45.

Preferably, the threshold value of the output of the dynamic strain gauge 42 is adjusted to a small load of contact between the organic tissue and the contact 6. The contact load is preferably adjusted to 20 gf or less, and further preferably to 10 gf or less, and most preferably to 2 gf or less.

FIG. 2 is a graph showing relations between the contact load and frequency change caused when the contact portion of the endoceliac physical quantity measuring apparatus is made to touch silicone rubbers with different physical quantities.

Referring to FIG. 2, the silicone rubber of silicone-3 is harder than the rubber of silicone-2, which is harder than the rubber of silicone-1. In comparing the physical quantities of soft objects, as seen from FIG. 2, the physical quantity resolution is improved if the change of the resonance frequency is detected in regions that are subjected to low contact loads.

FIG. 3 is a graph showing relations between the contact load and resonance voltage amplitude change in the driving electrode 11 of the electroacoustic transducer 5. These relations have the same tendency as the relations between the contact load and the resonance frequency change.

Accordingly, the same result can be obtained if the value of the resonance voltage amplitude change is used in place of that of the resonance frequency change. In this case, it is necessary only that an AC voltmeter be used instead of the frequency counter 41.

FIG. 4 is a graph showing relations between the contact load and output voltage amplitude change in the detecting electrode 14 of the electroacoustic transducer 5. These relations have the same tendency as the relations between the contact load and the resonance frequency change.

Accordingly, the same result can be obtained if the value of the output voltage amplitude change is used in place of that of the resonance frequency change. In this case, it is necessary only that an AC voltmeter be used instead of the frequency counter 41.

Also, the same result can be obtained by operating the apparatus in the same manner as in the present embodiment even in the case of an arrangement in which the filter circuit 37 is removed from the resonance circuit 38. In this case, moreover, a filter with flat transmission bandwidths, such as a stagger-tuned filter, may be located in place. Piezoelectric materials, such as piezoelectric ceramics, piezoelectric rubber, PVDF (polyvinylidene difluoride), etc., may be used for the force sensor 25. Alternatively, an optical force sensor or a capacitance-type force sensor may be used for this purpose.

An example of a force sensor is described in a paper entitled "A Flexible High-Resolution Tactile Imager with Video Signal Output" (by Makoto Shimojo, et al.) in Japan Mechanical Society Paper Collection (Vol. 57, No. 537) and a paper entitled "Improvement of a flexible sensor with pressure-sensitive rubber" (by Naoki Shinozaki, et al.) in J. Jpn. Soc. Stomatognathic Function (2, pp. 57–63, 1995). According to this force sensor, an array-type sensor of pressure-sensitive rubber can be obtained from a single element.

Furthermore, an optical sensor is described on page 371 of a paper entitled "Medical Application of Micromachine Technology" (by Yasuhiro Ueda) in Precision Engineering Society Journal (Vol. 62, No. 3, 1996).

According to the first embodiment described above, the ability of the apparatus to discriminate differences in physical quantities of even soft objects of measurement, such as organic tissues, can be improved.

The following is a description of a second embodiment of the present invention. Although the second embodiment is arranged substantially in the same manner as the first embodiment, its function is different. Only a difference between the first and second embodiments will be described below.

The value of the signal from the dynamic strain gauge 42 obtained when the output of the frequency counter 41 takes a predetermined value (threshold value) is detected as a feature quantity indicative of a physical quantity of the organic tissue. The detected feature quantity may be numerically displayed intact on the display means 45, or converted in any suitable manner such that the converted value can be displayed on the display means 45, FIG. 2 is a graph showing the relations between the contact load and the frequency change caused when the contact portion of the endoceliac physical quantity measuring apparatus is made to touch silicone rubbers with different physical quantities.

In comparing the physical quantities of soft objects, as seen from FIG. 2, the physical quantity resolution is improved if contact is detected when a threshold value for the variation of the resonance frequency is exceeded by the resonance frequency variation.

According to the second embodiment described above, the ability of the apparatus to discriminate differences in physical quantities of soft organic tissues can be improved.

The following is a description of a third embodiment of the present invention. Although the third embodiment is arranged substantially in the same manner as the first embodiment, its function is different. Only a difference between the first and third embodiments will be described below.

In the case where the endoceliac physical quantity measuring apparatus is caused to touch an organic tissue, according to the result shown in FIG. 2, the variation of the resonance frequency takes its extreme value and starts to decrease at a point of time after it increases on the minus side as the contact load increases. The softer the organic tissue, the greater the extreme value of the resonance frequency variation on the minus side is. The softer the organic tissue, moreover, the smaller the contact load value for the extreme value is.

As is evident from the above description, the physical quantities of the organic tissue can be identified by the resonance frequency value obtained when the resonance frequency value variation takes the extreme value as the contact load changes.

Accordingly, the signal value from the frequency counter 41 is measured simultaneously with the output of the dynamic strain gauge 42. The output value of the frequency counter 41 obtained when the variation of the signal from the counter 41 takes the extreme value on the minus side is detected as a feature quantity indicative of a physical quantity of the organic tissue The detected feature quantity may be numerically displayed intact on the display means 45, or converted in any suitable manner such that the converted value can be displayed on the display means 45.

The method according to the present embodiment can ensure the same operation and effects without measuring the contact load.

According to the third embodiment described above, the ability of the apparatus to discriminate differences in physical quantities of soft organic tissues can be improved.

The following is a description of a fourth embodiment of the present invention. Although the fourth embodiment is arranged substantially in the same manner as the third embodiment, its function is different. Only a difference between the third and fourth embodiments will be described below.

As is evident from the result shown in FIG. 2, the physical quantities of the organic tissues can be identified by the contact load value obtained when the resonance frequency value variation takes the extreme value. Accordingly, the signal value from the frequency counter 41 is measured simultaneously with the output of the dynamic strain gauge 42. The output value of the dynamic strain gauge 42 obtained when the variation of the signal from the counter 41 takes the extreme value on the minus side is detected as a feature quantity indicative of a physical quantity of the organic tissue. The detected feature quantity may be numerically displayed intact on the display means 45, or converted in any suitable manner such that the converted value can be displayed on the display means 45.

According to the fourth embodiment described above, the ability of the apparatus to discriminate differences in physical quantities of soft organic tissues can be improved.

The following is a description of a fifth embodiment of the present invention. Although the fifth embodiment is arranged substantially in the same manner as the first embodiment, its function is different. Only a difference between the first and fifth embodiments will be described below.

In the case where the endoceliac physical quantity measuring apparatus is caused to touch an organic tissues according to the result shown in FIG. 2, the variation of the resonance frequency takes its extreme value and starts to decrease at a point of time after it increases on the minus side as the contact load increases. The softer the organic tissue, the greater the inclination of the resonance frequency change to the contact load before the resonance frequency variation takes the extreme value on the minus side is. This indicates that the physical quantities of the organic tissue can be identified by the inclination of the resonance frequency change to the contact load.

Accordingly, the signal value from the frequency counter 41 is measured simultaneously with the output of the dynamic strain gauge 42. (F1, f1) and (F2, f2) are given as values for two different measurements in a region for a load lower than when the variation of the signal from the frequency counter 41 takes the extreme value on the minus side. F1 is the output value (contact load value) of the dynamic strain gauge 42 at a first measuring point, f1 is the output value (resonance frequency value) of the frequency counter 41 at the first measuring point, and F2 and f2 are the respective output values of the gauge 42 and the counter 41 at a second measuring point. A ratio (f2−f1)/(F2−F1) of the resonance frequency change to the contact load change is computed by means of the arithmetic circuit (computing means) 43. The ratio of the resonance frequency change to the contact load change is detected as a feature quantity indicative of a physical quantity of the organic tissue. The detected feature quantity may be numerically displayed intact on the display means 45, or converted in any suitable manner such that the converted value can be displayed on the display means 45.

Alternatively, the number of measuring points may be increased so that the ratio of the resonance frequency change to the contact load change can be obtained by a computing method such as the method of least squares.

Alternatively, moreover, the number of measuring points may be increased so that the changing rate of the resonance frequency with the contact load change at zero can be extrapolated by computation.

According to the fifth embodiment described above, the ability of the apparatus to discriminate differences in physical quantities of soft organic tissues can be improved.

Referring now to FIGS. 5 and 6, a sixth embodiment of the present invention will be described. FIG. 5 is a block diagram showing an endoceliac physical quantity measuring apparatus composed of a physical quantity sensor unit and a physical quantity measuring system according to the present embodiment, and FIG. 6 is a block diagram showing a configuration of a voltage detecting circuit.

An arrangement of the sixth embodiment will be described first. The endoceliac physical quantity measuring apparatus according to the sixth embodiment is cleared of the section corresponding to the force sensor that is used in the first embodiment. A detecting electrode 14, which is attached to a vibrator 7, is connected to a physical quantity measuring system 35 that includes an amplifier circuit 36 and a filter circuit 37. The output of the measuring system 35 is delivered to frequency measuring means 41 and a voltage detecting circuit 51. The respective outputs of the measuring means 41 and the circuit 51 are applied to the input of an arithmetic circuit 43.

The voltage detecting circuit 51 has a circuit configuration shown in FIG. 6. In FIG. 6, numeral 52 denotes a buffer with a high-impedance input, which serves to prevent the circuit 51 from influencing the resonance vibration of the piezoelectric vibrator 7. Numeral 53 denotes a low-pass filter, the cutoff frequency of which is lower than the resonance frequency of the vibrator 7. Numeral 54 designates a second amplifier circuit, which serves to amplify an output signal from the low-pass filter 53. The output of the second amplifier circuit 54 is connected to a voltmeter 55, which is connected to the arithmetic circuit 43.

The following is a description of the operation of the present embodiment. When a contact 6 of a physical quantity sensor unit 3 is held against an organic tissue, the resonance frequency of the vibrator 7 lowers with the physical quantities of the organic tissue.

Since the vibrator 7 is fixed by means of a fixing member 17, on the other hand, the vibrator 7 receives a compressive force from a contact load that acts between the contact 6 and the organic tissue. Accordingly, a voltage is produced by a piezoelectric effect in that part of the vibrator 7 which is located on the contact side of the fixing member 17, and appears at a driving electrode 11 situated corresponding to that part. The potential of the electrode 11 is obtained by superposing the voltage attributable to the piezoelectric effect on an output signal from the filter circuit 37 that drives the vibrator 7 for resonance vibration. The voltage attributable to the piezoelectric effect, which is caused by mechanical contact, has only a frequency component that is lower enough than the resonance frequency of the vibrator 7.

The potential of the driving electrode 11 is delivered to the voltage detecting circuit 51. Since the low-pass filter 53 is included in the circuit 51, a resonance signal from the vibrator 7 is cut, and only a signal that is based on the voltage attributable to the piezoelectric effect is transmitted to the second amplifier circuit 54. The circuit 54 amplifies the signal, and voltmeter 55 detects the voltage.

Thus, the voltage produced by the piezoelectric effect is proportional to the compressive force, so that the arithmetic circuit 43 computes the contact load between the contact 6 and the organic tissue in accordance with the value detected by the voltmeter 55.

Other processes of operation are carried out by the same method of the first embodiment, and the physical quantities of the organic tissue are displayed on display means 45.

Alternatively, the physical quantities of the organic tissue may be displayed by the methods according to the second to fifth embodiments.

According to the sixth embodiment described above, the vibrator 7 of the physical quantity sensor unit 3 can constitute a force sensor of a piezoelectric-effect type as load detecting means for measuring the contact load that acts between the organic tissue and the contact 6. Thus, the endoceliac physical quantity measuring apparatus can be simplified in construction and reduced in size. For other effects, the sixth embodiment resembles the first embodiment.

Referring now to FIG. 7, a seventh embodiment of the present invention will be described. FIG. 7 is a block diagram showing a configuration of a voltage detecting circuit.

Although the seventh embodiment has the same basic arrangement as the sixth embodiment, its voltage detecting circuit 51 is different. As shown in FIG. 7, the circuit 51 is designed so that the output of a buffer 52 is delivered to a high-pass filter 56 and a second buffer 57. The cutoff frequency of the filter 56 is lower than the resonance frequency of the vibrator 7. The respective outputs of the high-pass filter 56 and the second buffer 57 are amplified differentially by means of a differential amplifier 58. The output of the amplifier 58 is applied to the input of a voltmeter 59.

The following is a description of the operation of the voltage detecting circuit 51 according to the present embodiment. A signal inputted through the high-pass filter 56 is cleared of low-frequency components. Although the filter 56 transmits resonance-frequency components of the vibrator 7, therefore, it never transmits the voltage attributable to the piezoelectric effect produced by the contact load that acts between the contact 6 and the organic tissue. On the other hand, the second buffer 57 transmits all signals. When the difference between these two signals is amplified by means of the differential amplifier 58, it is cut by the high-pass filter 56, and the second buffer 57 outputs only the transmitted voltage attributable to the piezoelectric effect. This output is detected by the voltmeter 59. For other processes of operation, the seventh embodiment resembles the sixth embodiment.

According to the seventh embodiment described above, the vibrator 7 of the physical quantity sensor unit 3 can constitute load detecting means for measuring the contact load that acts between the organic tissue and the contact 6. Thus, the endoceliac physical quantity measuring apparatus can be simplified in construction and reduced in size. Further, data can be obtained at high speed. For other effects, the seventh embodiment resembles the first embodiment.

Referring now to FIG. 8, an eighth embodiment of the present invention will be described. FIG. 8 is a block diagram showing an endoceliac physical quantity measuring apparatus composed of a physical quantity sensor unit and a physical quantity measuring system according to the present embodiment.

Although the eighth embodiment has the same basic arrangement as the sixth embodiment, these embodiments are different in the following point. A vibrator 7 of a physical quantity sensor unit 3 is provided with a fourth electrode 61 that is situated nearer to a contact 6 than a fixing member 17, and the electrode 61 is connected to a voltage detecting circuit 51.

The following is a description of the operation of the arrangement described above. A voltage is produced in the fourth electrode 61 on the contact side by a piezoelectric effect produced by a contact load that acts between the contact 6 and an organic tissue. This voltage is detected by the voltage detecting circuit 51. For other processes of operation, the eighth embodiment resembles the sixth or seventh embodiment.

The eighth embodiment produces the same effects of the sixth embodiment.

Figure 9:
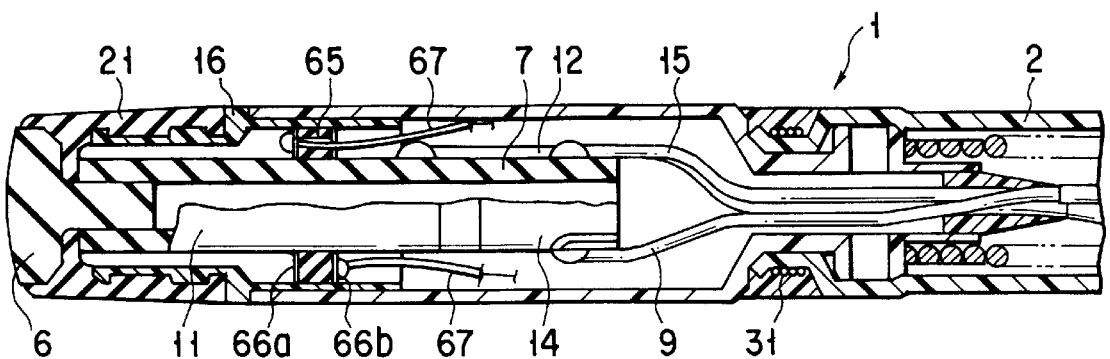
FIG. 9 is a longitudinal sectional view of a physical quantity sensor unit of an endoceliac physical quantity measuring apparatus according to a ninth embodiment of the invention.

Referring now to FIG. 9, a ninth embodiment of the present invention will be described. FIG. 9 is a longitudinal sectional view of a physical quantity sensor unit of an endoceliac physical quantity measuring apparatus according to the present embodiment.

The ninth embodiment is constructed in the same manner as the eighth embodiment except for the following point. A fixing member 65 for holding a vibrator 7 is formed of a piezoelectric ceramic material, and is provided with electrodes 66a and 66b, thus forming a piezoelectric-effect force sensor for use as load detecting means. The electrodes 66a and 66b are connected to a voltage detecting circuit 51 by means of electric wires 67, individually.

The following is a description of the operation of the arrangement described above. When a contact 6 touches an organic tissue, it is pressed so that a shearing stress acts on a vibrator fixing member 65. Accordingly, a voltage is produced between the electrodes 66a and 66b that are attached to the fixing member 65, and is detected by means of a voltage detecting circuit 51. Based on the result of the detection, an arithmetic circuit 43 computes a contact load that acts between the contact 6 and the organic tissue. For other processes of operation, the ninth embodiment resembles the eighth embodiment.

According to the ninth embodiment described above, the vibrator fixing member and the force sensor can be composed of the same member, so that the apparatus can be simplified in construction and reduced in size. Further, data can be obtained at high speed. For other effects, the ninth embodiment resembles the first embodiment.

Figure 10:
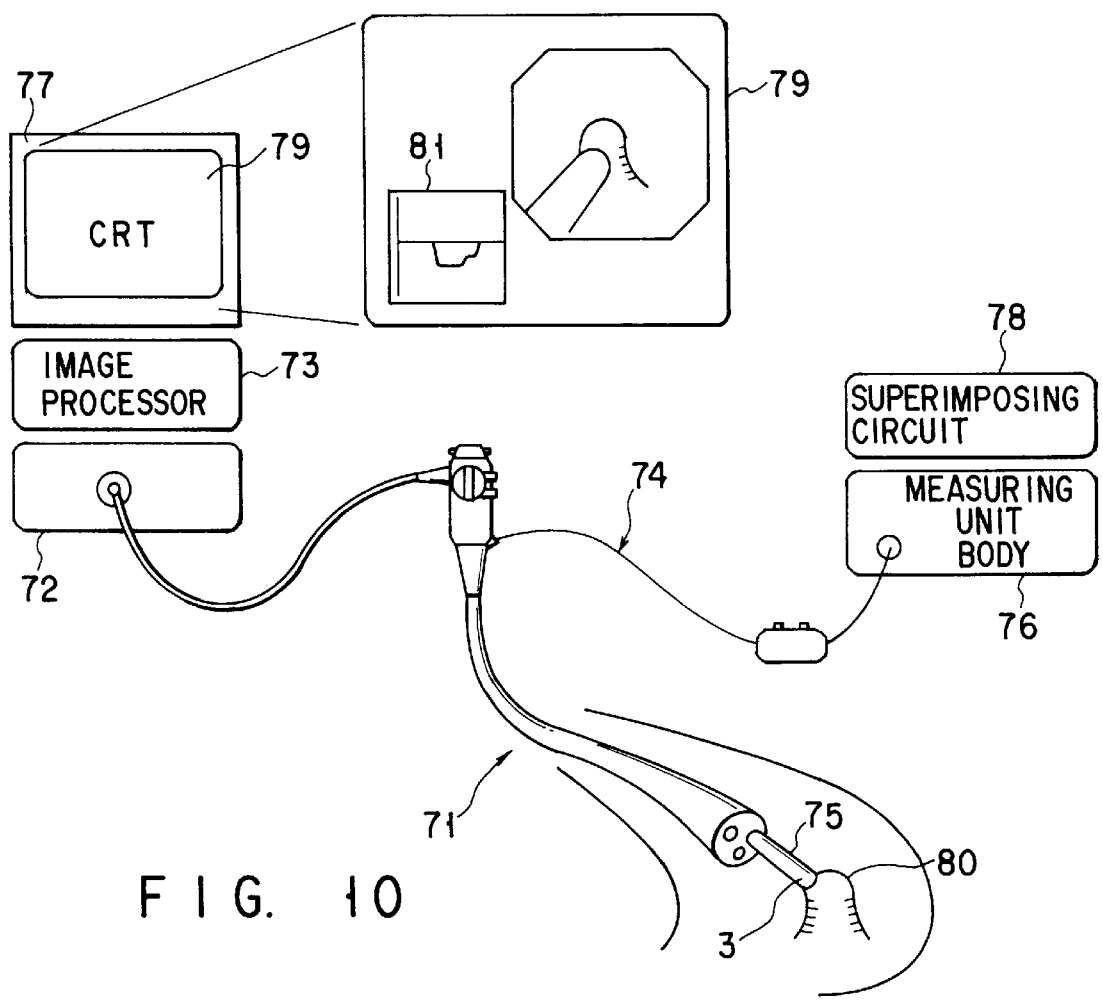
FIG. 10 is a diagram for illustrating a system using an endoceliac physical quantity measuring apparatus according to a tenth embodiment of the invention under endoscopic observation.

Referring now to FIG. 10, a tenth embodiment of the present invention will be described. FIG. 10 is a diagram for illustrating a system that uses an endoceliac physical quantity measuring apparatus under endoscopic observation.

In FIG. 10, numeral 71 denotes an endoscope, which is connected to an endoscopic light source unit 72 and an endoscopic image processor 73. Numeral 74 denotes a sensor catheter, which includes a flexible insert section 75 that has a physical quantity sensor unit 3 of the endoceliac physical quantity measuring apparatus in its distal end portion, and can be inserted into a forceps hole in the endoscope. The proximal end of the catheter 74 is connected to a measuring unit body 76, which contains a frequency counter 41, dynamic strain gauge 42, arithmetic circuit 43, etc. Also, the measuring unit body 76 outputs information on the measuring apparatus as a video signal that can be displayed on a CRT 77.

The video signal from the measuring unit body 76 and an endoscopic image from the endoscopic image processor 73 are applied to a superimposing device 78, whereupon they are superimposed and displayed on a screen 79 of the CRT 77.

The following is a description of the operation of the arrangement described above.

The CRT 77 is observed as the insert section of the endoscope 71 is inserted into the body cavity, and an organic tissue 80 to be measured for physical quantities is displayed on the screen 79 of the CRT 77. Then, the insert section 75 of the sensor catheter 74 is passed through the forceps hole in the endoscope 71 so that the physical quantity sensor unit 3 at the distal end of the catheter 74 projects from the distal end of the endoscope. When the catheter 74 is caused further to project from the endoscope 71 so that it touches the organic tissue 80, the state of vibrator resonance in the endoceliac physical quantity measuring apparatus changes. This change is converted into physical quantity information 81, which is displayed superimposed on the screen 79 of the CRT 77. Thereupon, the operator can appreciate physical quantities of the organic tissue 80 as he observes the endoscopic image.

According to the tenth embodiment described above, the physical quantities of the organic tissue in the body cavity can be measured through the endoscope. Also, physical quantity data can be observed together with the endoscopic image.

The load detecting means according to the present invention may be of various types, including an optical force sensor, capacitance-type force sensor, piezoelectric-effect force sensor, etc. The piezoelectric-effect force sensor may be composed of piezoelectric ceramics, piezoelectric rubber, PVDF, etc. All or some of the embodiments described herein may be combined without departing from the scope of the invention.

As the effects of the first to tenth embodiments described herein are coordinated, the ability of the apparatus to discriminate differences in physical quantities of soft objects of measurement, such as organic tissues, can be improved, and the reliability of measured data can be heightened.

Figure 11:
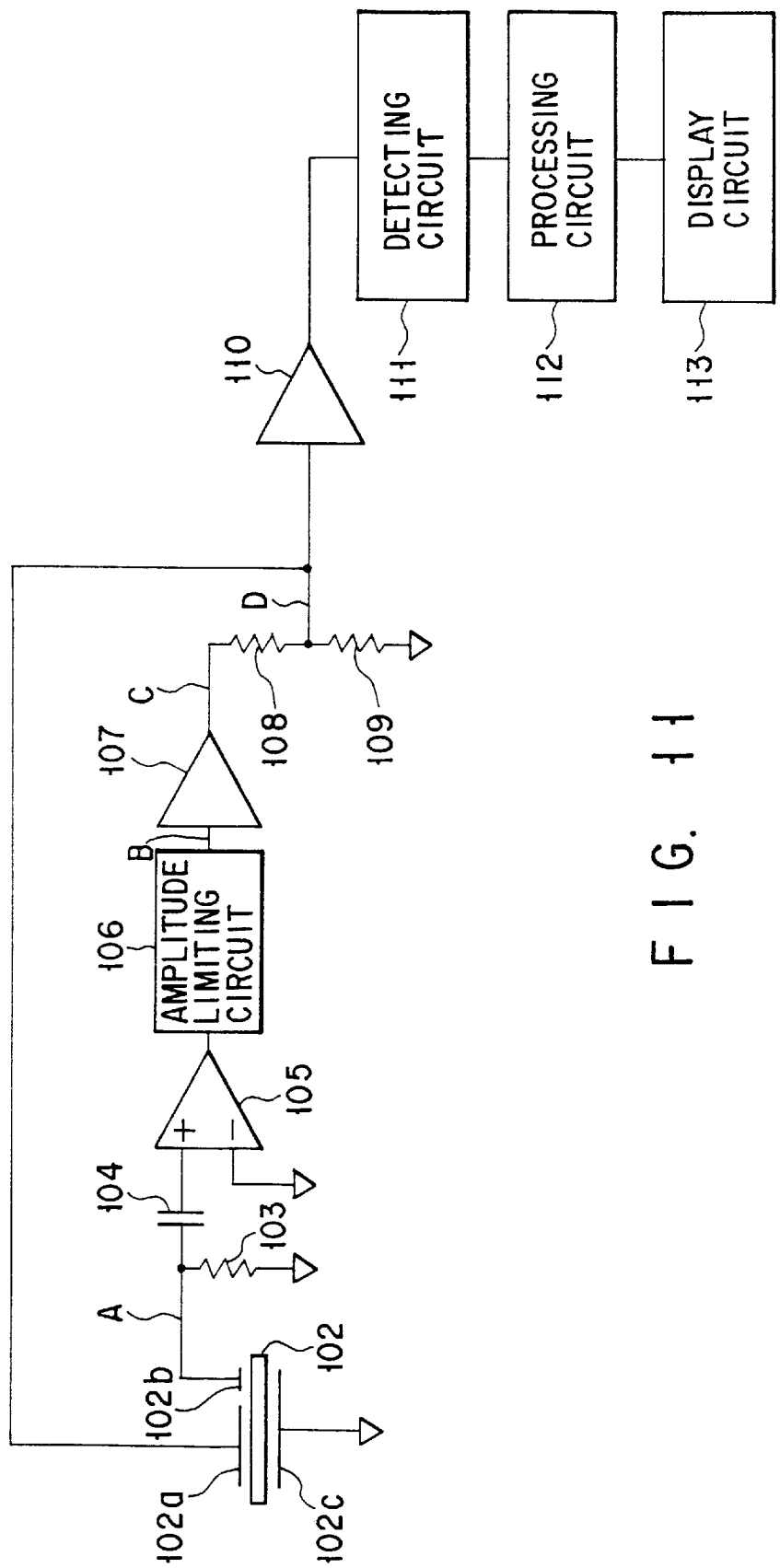
FIG. 11 is a diagram showing an arrangement of an endoceliac physical quantity measuring apparatus according to an eleventh embodiment of the invention.

FIG. 11 is a diagram showing an arrangement of an endoceliac physical quantity measuring apparatus according to an eleventh embodiment of the present invention.

As shown in FIG. 11, a piezoelectric vibrator 102 is provided with an exciting electrode 102a, feedback electrode 102b, common grounding electrode 102c, and contact (not shown). The feedback electrode 102b of the vibrator 102 is connected to the noninverted input of a comparator 105 through a high-pass filter, which is composed of a resistor 103 and a capacitor 104. As the high-pass filter is interposed in this manner, a signal from the feedback electrode 102b is applied to the input of the comparator 105 after it is cleared from its DC component. It is to be desired that the resistor 103 should have a resistance value approximate to the impedance value of the feedback electrode 102b at the resonance frequency of the piezoelectric vibrator 102.

The inverted input of the comparator 105 is grounded, and the output thereof is connected to the input of a band-pass filter 107. An amplitude limiting circuit 106 is provided at the junction. The output of the filter 107 is grounded through resistors 108 and 109. Further, the junction of the resistors 108 and 109 is fed back to the exciting electrode 102a of the piezoelectric vibrator 102. Preferably, the resistance value of the resistor 108 is greater than the impedance value of the electrode 102a at the resonance frequency. The resistor 109 is provided in order to cancel a DC voltage produced in the exciting electrode 102a, and preferably has a resistance higher enough than that of the resistor 108.

The above elements constitute a resonance circuit section of the apparatus of the present embodiment. The output of the resonance circuit is also connected to the input of a buffer 110, the output of which is connected to the input of a display circuit 113 through a detecting circuit 111 and a processing circuit 112. The buffer 110 has a high-impedance input lest a signal transmitted to the detecting circuit 111 influence the resonance state. The circuit 111 is composed of a frequency detecting circuit or a voltage amplitude detecting circuit. The processing circuit 112 serves to convert the output of the detecting circuit 111 into information on physical quantities. The display circuit 113 is used to display measured physical quantity information. These elements constitute the endoceliac physical quantity measuring apparatus according to the present embodiment.

Referring now to FIG. 13, phase and gain characteristics of the piezoelectric vibrator 102 will be described.

FIG. 13 shows characteristics of a signal delivered from the feedback electrode 102b when a low-amplitude signal with a continuously varying frequency is applied to the exciting electrode 102a. In FIG. 13, E and F represent a frequency-gain characteristic and a frequency-phase characteristic, respectively. A frequency at which the vibrator 102 is resonant corresponds to a point P at which the gain characteristic E assumes its maximum value. At this point of time, the phase characteristic is subject to a phase rotation of about +90°.

Referring further to FIG. 14, phase and gain characteristics of the band-pass filter 107 will be described.

Figure 12A:
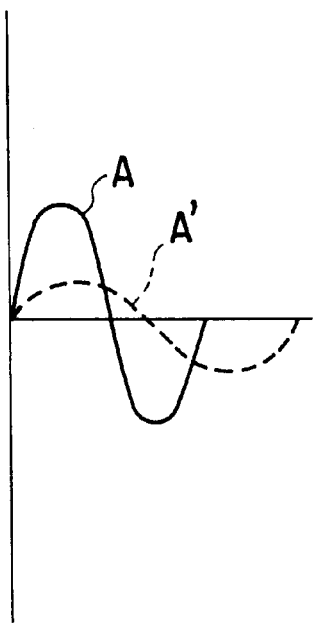
FIGS. 12A, 12B, 12C and 12D are diagrams showing the states of signals at individual nodes of the apparatus of FIG. 11.

In FIG. 14, G and H represent a frequency-gain characteristic and a frequency-phase characteristic, respectively. A band-pass frequency as a feature quantity of the band-pass filter 107 corresponds to a point Pf at which the gain characteristic G assumes its maximum value. At this point of time, the phase rotation of the phase characteristic is 0°. At a frequency higher than Pf, the gain decreases as the frequency increases, and the phase characteristic rotates negatively toward –90°. Since the resonance frequency is approximate to the resonance frequency of the piezoelectric vibrator 102, the phase of the signal delivered from the feedback electrode 102b, compared with that of the signal applied to the exciting electrode 102a, is advanced for +90°. The signal delivered from the feedback electrode 102b corresponds to a signal A represented by full line in FIG. 12A.

The following is a detailed description of the operation of the endoceliac physical quantity measuring apparatus according to present embodiment.

Figure 12B:
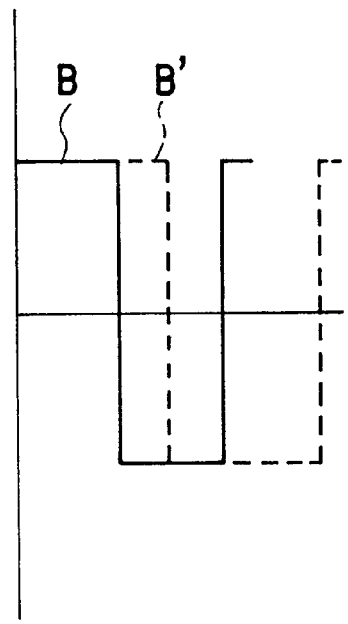

In the arrangement described above, the feedback signal A from the feedback electrode 102b of the piezoelectric vibrator 102 is applied to the noninverted input of the comparator 105 after its DC component is removed by means of the high-pass filter. The feedback signal A is represented by full line in FIG. 12A. After the feedback signal A is compared with a reference signal (zero-volt signal in this case) and binary-coded in the comparator 105, it is delivered from the output of the comparator, and its amplitude is limited by the amplitude limiting circuit 106. Thereafter, the signal is delivered as an output signal B to the band-pass filter 107. The output signal B is represented by full line in FIG. 12B.

Figure 12C:
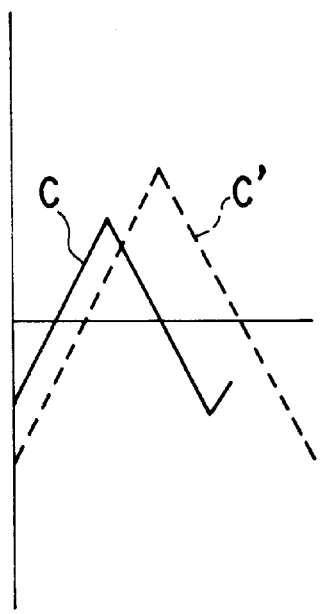

As shown in FIG. 14, the band-pass filter 107 has the phase and gain characteristics. If the band-pass frequency is adjusted in advance to a level lower than the resonance frequency of the piezoelectric vibrator 102, an output signal C is delivered from the filter 107, as indicated by full line in FIG. 12C. At this point of time, the phase of the signal C, compared with that of the signal B, is advanced for –90° on account of the phase characteristic of the band-pass filter 107.

Figure 12D:
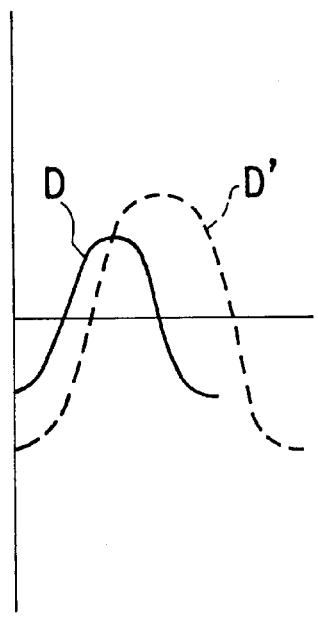

The signal C is applied to the resistor 108. Since the resistor 108 and the piezoelectric vibrator 102 constitutes a low-pass filter, the signal C is rounded to have the shape of a signal D, as indicated by full line in FIG. 12D, and is fed back to the exciting electrode 102a of the vibrator 102. Since there is a phase difference of approximately 90° between the signals D and A, the vibrator 102 is subjected to positive feedback and undergoes resonance vibration.

If a soft object of measurement, such as an organic tissue, is caused to touch a contact (not shown), the frequency-gain characteristic of the piezoelectric vibrator 102 changes.

Thereupon, the resonance frequency of the vibrator 102 lowers, so that the resonant-state gain and the extent of rotation of the phase also lower. A signal A' from the feedback electrode 102b is indicated by broken line in FIG. 12A. The signal A' is applied to the input of the comparator 105, whereupon it turns to a signal B' indicated by broken line in FIG. 12B. As is also evident from FIG. 12B, the signal B', which is obtained through the comparator, has a waveform with the same amplitude as when in a noncontact state and different in frequency only, although the signal A' has a reduced amplitude.

The output signal B' from the comparator 105 is applied to the band-pass filter 107, and its gain increases as the frequency characteristic of the filter 107 and the resonance frequency are lowered. Thus, an output signal C' from the filter 107 has an increased amplitude. The signal C' is represented by broken line in FIG. 12C. Since the impedance of the piezoelectric vibrator 102 is increased at this point of time, the ratio in impedance between the resistor 108 and the exciting electrode 102a of the vibrator 102 changes, so that a voltage applied to the vibrator 102 increases. A signal D' applied to the vibrator 102 at this time is represented by broken line in FIG. 12D.

The respective changes of the signals D and D' are transmitted to the detecting circuit 111 through the buffer 110, and are delivered through the processing circuit 112 to the display circuit 113 to be displayed thereby.

In the endoceliac physical quantity measuring apparatus according to the eleventh embodiment, as described above, the amplitude voltage of the signal applied to the band-pass filter can be made constant by receiving the signal from the feedback electrode 102b of the piezoelectric vibrator 102 by means of the comparator 105. Accordingly, the increase in gain of the output of the filter 107 that is caused when the resonance frequency is lowered can be secured on a higher level than when the comparator 105 is not inserted.

In the case where the detecting circuit 111 is provided with voltage amplitude detecting means, moreover, a greater amplitude variation can be detected, and the sensor resolution can be improved. Since the gain of the signal from the feedback electrode 102b need not be adjusted, furthermore, the resulting endoceliac physical quantity measuring apparatus is easy to adjust.

The following is a description of an endoceliac physical quantity measuring apparatus according to a twelfth embodiment of the present invention.

FIG. 15 is a diagram partially showing an arrangement of the apparatus according to the twelfth embodiment. The apparatus of the present embodiment is constructed basically in the same manner as the one shown in FIG. 11, provided that a peripheral circuit of its comparator 105 is arranged differently, as shown in FIG. 15. In the following, a description of the same portions as are shown in FIG. 11 is omitted, and different portions will be described in the main.

As shown in FIG. 15, a feedback electrode 102b of a piezoelectric vibrator 102 is grounded through a resistor 114, and is connected to the noninverted input of a comparator 105. The inverted input of the comparator 105 is connected to a potentiometer 115. For the arrangement of other components, the twelfth embodiment resembles the eleventh embodiment.

In this arrangement, a signal from the feedback electrode 102b of the piezoelectric electrode 102 is applied to the noninverted input terminal of the comparator 105. According to the present embodiment, a reference signal for the comparator 105 can be adjusted by means of the potentiometer 115, which serves to regulate the ratio between comparator output signals.

In the endoceliac physical quantity measuring apparatus according to the twelfth embodiment, as described above, the output ratio of the comparator 105 can be regulated by adjusting the potentiometer 115 despite a DC component voltage involved in the signal generated by the feedback electrode 102b.

The following is a description of an endoceliac physical quantity measuring apparatus according to a thirteenth embodiment of the present invention.

FIG. 16 is a diagram partially showing an arrangement of the apparatus according to the thirteenth embodiment.

The apparatus of the present embodiment is constructed basically in the same manner as the one shown in FIG. 11, provided that a peripheral circuit of its comparator 105 is arranged differently, as shown in FIG. 16. In the following, a description of the same portions as are shown in FIG. 11 is omitted, and different portions will be described in the main.

As shown in FIG. 16, the input side of the comparator 105, like that of the eleventh embodiment, is composed of a high-pass filter that includes a resistor 103 and a capacitor 104, while the output of the comparator is connected to a potentiometer 116. The potentiometer 116 is provided in order to divide an output signal from the comparator 105. For the arrangement of other components, the thirteenth embodiment resembles the eleventh embodiment.

In this arrangement, the amplitude of the output signal from the comparator 105 is controlled by dividing the signal by means of the potentiometer 116. Also, the signal amplitude is regulated by adjusting the potentiometer 116.

According to the thirteenth embodiment, as described above, the amplitude of a signal applied to a band-pass filter 107 can be regulated by means of the potentiometer 116.

The following is a description of an endoceliac physical quantity measuring apparatus according to a fourteenth embodiment of the present invention.

Figure 17:
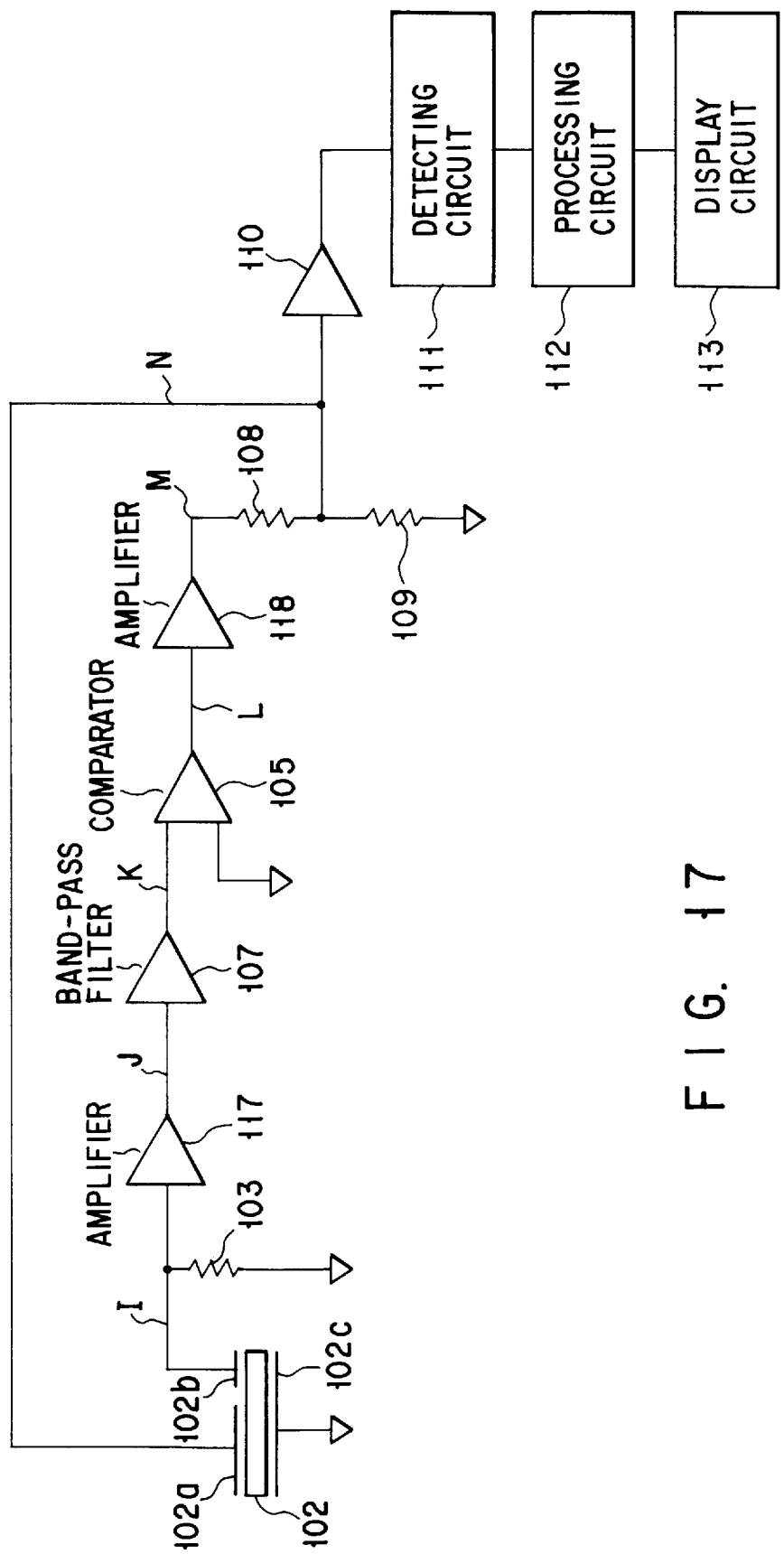
FIG. 17 is a diagram showing an arrangement of an endoceliac physical quantity measuring apparatus according to a fourteenth embodiment of the invention.

FIG. 17 is a diagram partially showing an arrangement of the apparatus according to the fourteenth embodiment.

The apparatus of the present embodiment is constructed basically in the same manner as the one shown in FIG. 11. In the following, a description of the same portions as are shown in FIG. 11 is omitted, and different portions will be described in the main.

As shown in FIG. 17, the output of a feedback electrode 102b of a piezoelectric vibrator 102 is grounded through a resistor 103, and is connected to the input of an amplifier 117. The output of the amplifier 117 is connected to the noninverted input of a comparator 105 through a band-pass filter 107. The inverted input of the comparator 105 is grounded, and the output thereof is connected to an amplifier 118. The output of the amplifier 118 is grounded through resistors 108 and 109, the junction of which is connected to the input of a buffer 110. The output of the buffer 110 is connected to the input of a display circuit 113 through a processing circuit 112. The amplifier 117 receives a high-impedance signal from the feedback electrode 102b of the piezoelectric vibrator 102, and transmits it to the band-pass filter 107 in the next stage. The amplifier 118, which receives the output of the comparator 105, serves to amplify power for driving the vibrator 102.

In this arrangement, a signal I shown in FIG. 18 is delivered from the feedback electrode 102b of the piezoelectric vibrator 102. This signal I is amplified to become a signal J by the amplifier 117. Further, the signal J is passed through the band-pass filter 107 to become a signal K. Since the filter 107 has a bandpass frequency lower than the resonance frequency of the vibrator 102, the signal K has a waveform that is subject to a phase delay of about 90°, as compared with the signal J.

The output of the band-pass filter 107 is applied to the comparator 105 and binary-coded therein. As shown in FIG. 18, the output of the comparator 105 is in the form of a square wave L that is subject to a phase delay of 90° behind the signal I from the feedback electrode 102b of the piezoelectric vibrator 102.

The square wave L is applied to the input of the amplifier 118, whereupon it is subjected to necessary power amplification for the drive of the piezoelectric vibrator 102, thereby turning to a square wave M. This output signal M from the amplifier 118 applied to an exciting electrode 102a of the vibrator 102. Before the square wave M is applied to the electrode 102a, it is rounded like a signal N on account of a capacitance effect of the vibrator 102. According to the gain and phase characteristics of the vibrator 102, the phase is advanced for −90° in the vicinity of the resonance frequency of the vibrator 102, so that a signal that appears at the feedback electrode 102b resembles the signal I. Thus, in this arrangement, the piezoelectric vibrator 102 is subjected to positive feedback with a uniform phase.

The following is a description of a case in which an organic tissue is caused to touch a contact (not shown) that is connected to the piezoelectric vibrator 102. If the organic tissue is a soft one, the vibrator is lowered in frequency and gain and reduced in phase rotation in the resonant state, and its impedance increases. Thus, the resonance frequency of the apparatus according to the present embodiment lowers.

The amplitude of the signal from the feedback electrode 102b is reduced, and the phase difference between the signals I and N becomes smaller. Although the signal J amplified by the amplifier 117 is applied to the band-pass filter 107, the gain of the filter 107 is increased and the phase delay is reduced due to the lowered resonance frequency. Since the output signal K from the filter 107 is applied to the comparator 105, the respective amplitudes of the waveforms L and M, results of the output from the comparator 105, never change, and only the resonance frequency is changed.

Since the phase delay in the band-pass filter 107 is reduced, moreover, the phase delay of the signal N is also reduced. Even when the organic tissue touches the contact, therefore, mismatching between phases of the resonance circuit can be kept slight. Since the impedance of the piezoelectric vibrator 102 increases, furthermore, the amplitude of the voltage applied to the exciting electrode 102a of the vibrator 102 is increased by a voltage dividing effect produced between the resistor 108 and the vibrator 102. Even when the amplitude from the feedback electrode 102b is reduced, therefore, the voltage applied to the exciting electrode 102a can be kept high enough by the effect of the comparator.

According to the fourteenth embodiment, as described above, a square wave can be used to drive the piezoelectric vibrator 102. Accordingly, the impedance value of the vibrator 102 can be measured by observing the voltage applied to the exciting electrode 102a of the vibrator 102. Thus, physical quantities of the organic tissue can be measured in accordance with the impedance characteristic of the vibrator 102. For other effects, the fourteenth embodiment resembles the eleventh embodiment.

The following is a description of a system according to a fifteenth embodiment of the present invention. In this system, any of the endoceliac physical quantity measuring apparatuses according to the eleventh to fourteenth embodiments is inserted into a forceps hole in an endoscope, and physical quantities of an organic tissue are measured through the endoscope.

Figure 19:
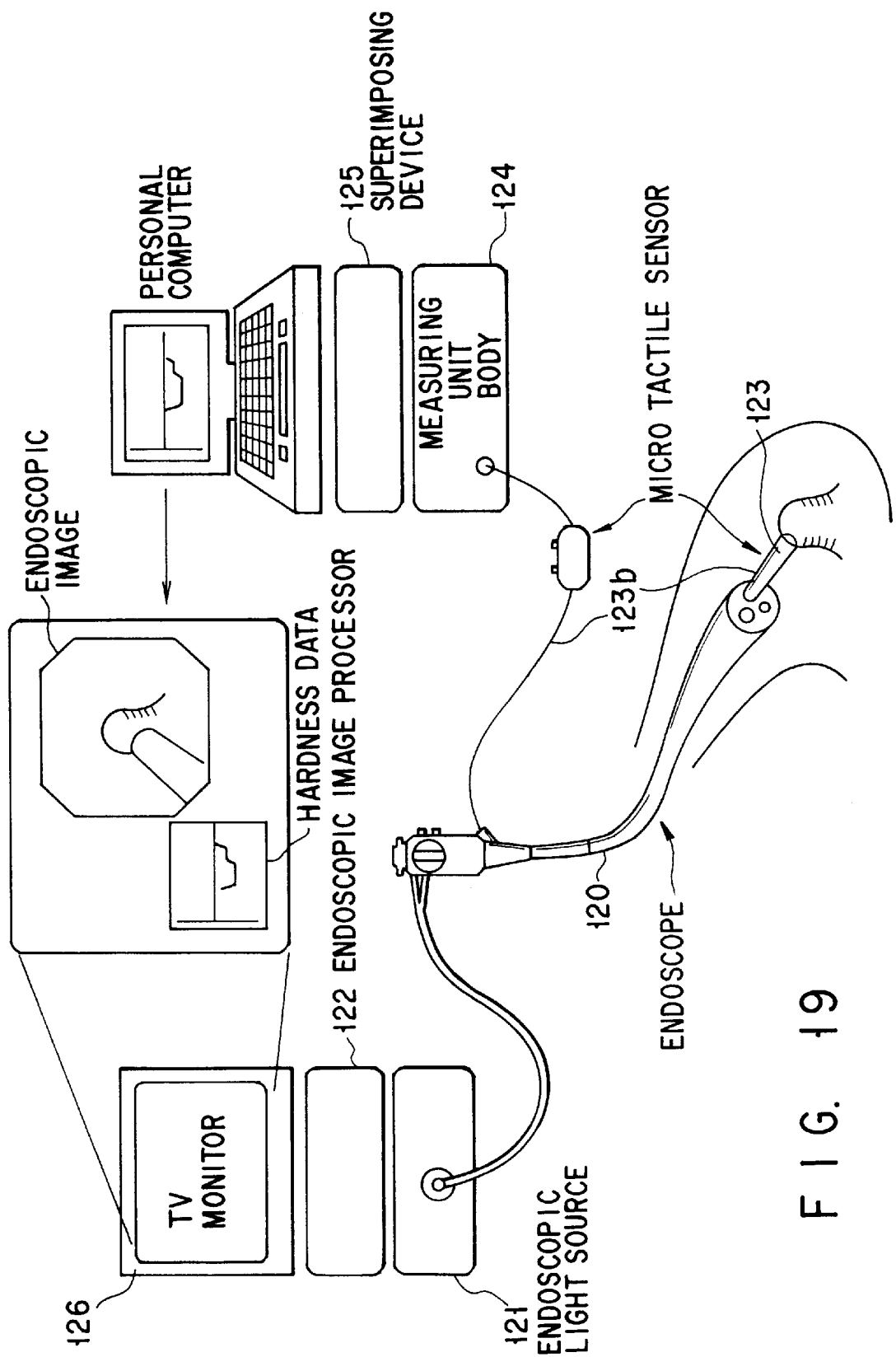
FIG. 19 is a diagram showing an arrangement of an endoceliac physical quantity measuring apparatus according to a fifteenth embodiment of the invention.

As shown in FIG. 19, an endoscope 120 is connected to an endoscopic light source 121 and an endoscopic image processor 122. A sensor catheter 123 has the endoceliac physical quantity measuring apparatus according to the present invention in its distal end portion, and includes a flexible insert section 123b that can be inserted into the forceps hole in the endoscope. The catheter 123 is connected to a measuring unit body 124, which contains the detecting circuit 111 and the processing circuit 112 shown in FIG. 11.

The measuring unit body 124 outputs information on a physical quantity sensor as a video signal that can be displayed on a CRT. The video signal from the measuring unit body 124 and an endoscopic image from the endoscopic image processor 122 are applied to a superimposing device 125, whereupon they are superimposed and displayed on a TV monitor 126.

Figure 20:
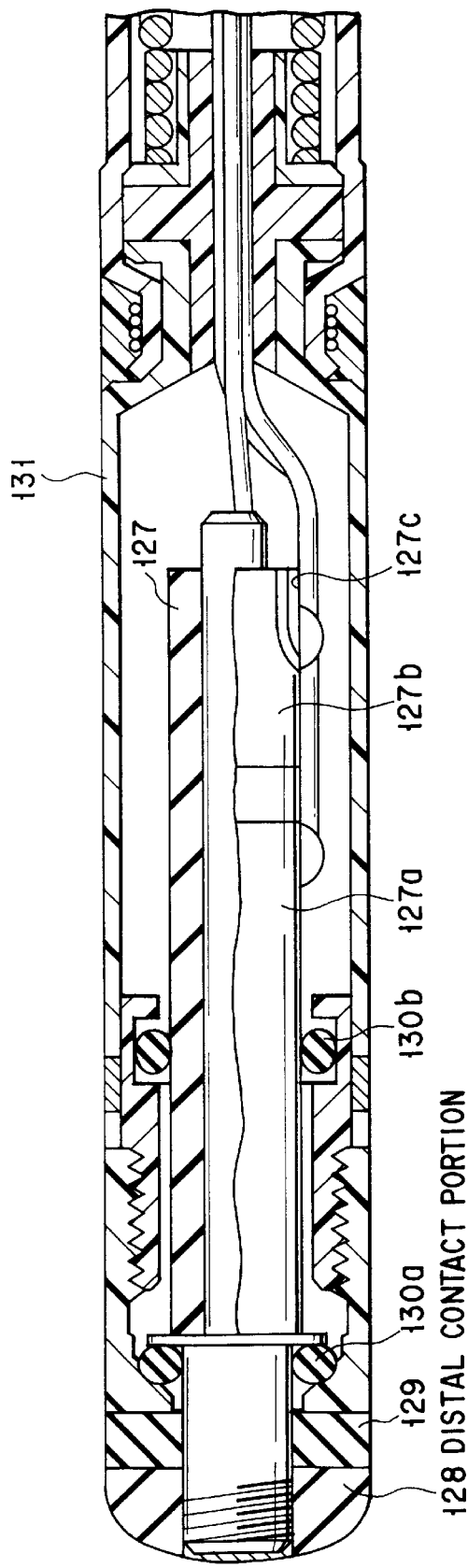
FIG. 20 is a sectional view showing an arrangement of the distal end portion of a sensor catheter.

FIG. 20 is a sectional view showing an arrangement of the distal end portion of the sensor catheter 123.

In FIG. 20, a piezoelectric vibrator 127 is provided with an exciting electrode 127a, feedback electrode 127b, and common grounding electrode 127c. These electrodes are connected with an electric cable, and is connected with the measuring unit body 124 of FIG. 19 by means of the insert section 123b. A distal contact portion 128 is connected mechanically to the vibrator 127.

A gasket 129, which is formed of silicone rubber or polyurethane, serves to keep the physical quantity sensor watertight lest water get into the sensor when the outer surface of the sensor is wetted. O-rings 130a and 130b position the piezoelectric vibrator 127 lest it come into contact with a sheath 131.

With this arrangement, the TV monitor 126 is observed as the endoscope 120 is inserted into the body cavity, and the organic tissue to be measured for physical quantities is displayed on the monitor 126. Then, the sensor catheter 123 is passed through the forceps hole in the endoscope 120 so that it projects from the distal end of the endoscope. When the catheter 123 is caused further to project from the endoscope 120 so that it touches the organic tissue, the state of resonance in the endoceliac physical quantity measuring apparatus changes. This change is converted into physical quantity information, which is displayed superimposed on the TV monitor 126. Thereupon, the operator can appreciate physical quantities of the organic tissue as he observes the endoscopic image.

According to the fifteenth embodiment, as described above, the physical quantities of the organic tissue in the body cavity can be measured through the endoscope. Also, physical quantity data can be observed together with the endoscopic image.

Although various embodiments of the present invention have been described herein, it is to be understood that the invention is not limited to these embodiments, and that various changes and modifications may be effected therein by one skilled in the art without departing from the scope or spirit of the invention. In any of the embodiments described above, for example, the apparatus comprises the band-pass filter. It is to be understood, however, that the same effects can be obtained from any of the embodiments without the use of the band-pass filter.

Putting the effects of the eleventh to fifteenth embodiments together, there may be provided an endoceliac physical quantity measuring apparatus in which change in a resonant-state amplitude is enhanced by using a square signal waveform in the resonance circuit, so that the detecting capability is improved, and gain adjustment is easy.

Referring now to FIGS. 21A and 21B, a sixteenth embodiment of the present invention will be described.

FIG. 21A shows an outline of an endoceliac physical quantity measuring apparatus according to the sixteenth embodiment. In FIG. 21A, numeral 201 denotes an elongate catheter that forms the body of a physical quantity sensor probe. The catheter 201 can be introduced into a patient's body cavity through a guide channel of an endoscope by a measurer (not shown). As shown in FIG. 21B, a casing 202 having the same diameter as the catheter 201 is attached coaxially to the distal end of the catheter. The casing 202 is composed of proximal-side casing member 203 and a distal-side casing member 204. The two members 203 and 204 are coupled together in a manner such that the proximal end portion of the distal-side member 204 is screwed onto a connecting ring 205 that is fixed to the inner surface of the distal end portion of the proximal-side member 203. The respective end faces of the members 203 and 204 abut against each other.

The distal end of a coil core 206 of the catheter 201 and the distal end portion of the catheter are put on the rearmost end portion of the proximal-side casing member 203. The distal end portion of the catheter 201 is fastened at its spool portion 207 and fixed by means of a sealant 208. On the other hand, the distal end portion of the coil core 206 is brazed to the rearmost end portion of the proximal-side casing member 203.

The distal end portion of the distal-side casing member 204 is in the form of a tapered cylinder. A cylindrical vibrator 211, having a space therein, is disposed coaxially in the casing 202. While this vibrator 211 is formed of, for example, a piezoelectric ceramic material, it may alternatively be formed of a crystal oscillator, magnetostrictive element, or high-molecular piezoelectric material (PVDF). The vibrator 211 is polarized in its radial direction, and is fitted with electrodes on its inner and outer peripheral surfaces, individually. When a voltage that varies with time is applied to the two electrodes on the inner and outer peripheral surfaces by means of feeder cords 212, the vibrator 211 is excited to start mechanical vibration.

A contact 213, which extends axially in front of the hollow vibrator 211, is fixedly bonded to the distal end of the vibrator in a coaxial manner. Formed on the rear end of the contact 213 is a projection 213a, which is fitted tight in a bore 211a of the vibrator 211. Since the projection 213a is fixed in a manner such that it is fitted tight in the vibrator bore 211a, the contact 213 and the vibrator 211 are intimately in touch with each other. At least the vibrator 211 and the contact 213 constitute a mechanical vibration unit.

The outer peripheral surface of the contact 213 is tapered toward the distal end side in the axial direction, covering a length equal to ¼ of the wavelength of an axial elastic vibration. Accordingly, the contact 213 magnifies the amplitude of vibration. Preferably, in general, the contact 213 should be shaped so that the sectional area of the mechanical vibration unit, which includes the contact 213 or the vibrator 211, is reduced in the direction of propagation of vibration, covering a length equal to at least ¼ to ½ of the wavelength of the axial elastic vibration from the distal end portion of the contact 213. Further, the contact 213 preferably has an overall length equal to ¼ to ½ of the wavelength of the axial elastic vibration of the mechanical vibration unit.

The tapered outer peripheral surface of the contact 213 is inclined so as to fit the tapered inner surface of the distal-side casing member 204. The distal end of the contact 213 has the shape of a truncated cone that can be held against an object of measurement, that is, an organic tissue 214. Thus, only the distal end portion of the contact 213 forms a narrow flat abutting surface that serves as an abutting portion 215.

A detecting element 218 is located close to and coaxially with the proximal end portion of the vibrator 211. The element 218 can vibrate in cooperation with the vibrator 211, thus serving as a sensor for monitoring the amplitude and frequency of the vibration of the vibrator 211. The detecting member 218, like the vibrator 211, may be formed of a piezoelectric ceramic material or crystal oscillator. An integral unit including the vibrator 211, contact 213, and detecting element 218 is held on the inner surface of the casing 202 with the aid of two ring-shaped elastic members 216a and 216b. The one elastic member 216a is fitted in an inner peripheral groove 217 of the connecting ring 205 that is fixed to the casing 202, while the other elastic member 216b is interposed between the outer peripheral portion of the rear end portion of the contact 213 and the inner surface portion of the distal-side casing member 204. Since the elastic members 216a and 216b are interposed between the casing 202 and the vibrator 211 and between the casing 202 and the contact 213, respectively, the mechanical vibration of the vibrator 211 cannot be transmitted to the casing 202. Mechanical vibration of a mechanical vibration system 219 composed of the integral unit that includes the contact 213, vibrator 211, and detecting element 218 cannot be inhibited if the elastic members 216a and 216b are provided individually for breaks in the mechanical vibration. The elastic members 216a and 216b may be located in any other positions than those on the contact 213. The abutting portion 215 of the contact 213 is mounted so as to project from the distal end of the casing 202.

As shown in FIG. 21A, on the other hand, an output signal from the detecting element 218 is applied to the input of a filter circuit 222 through an amplifier circuit 221 of an apparatus that is installed outside the catheter 201, by means of an output cord 220. The output of the filter circuit 222 is applied again to the input of the vibrator 211 in the casing 202, and serves as a driving signal for the vibrator 211. Thus, the vibrator 211, detecting element 218, amplifier circuit 221, and filter circuit 222 form a closed self-oscillation circuit. As this self-oscillation circuit is activated, the mechanical vibration system 219, composed of the vibrator 211, contact 213, and detecting element 218, undergoes mechanical resonance vibration as the integral mechanical vibration unit.

The filter circuit 222 may be formed of, for example, a band-pass filter, integral circuit, differential circuit, or peaking circuit that has a frequency band whose gain varies depending on the frequency.

Voltage measuring means 225 and frequency measuring means 226 are connected to the output line of the filter circuit 222, whereby the voltage and frequency of the operating self-oscillation circuit can be monitored. These measuring means 225 and 226 may be located in any suitable positions in the self-oscillation circuit.

According to the arrangement described above, the measurer introduces the catheter 201 into the body cavity through an auxiliary instrument, such as an endoscope. Then, the measurer operates the catheter 201 to touch the surface of the organic tissue 214 with the distal end of the contact 213 in resonance vibration. If the organic tissue 214 is an elastic object, such as rubber, the resonance frequency of the mechanical vibration system 219 slightly lowers as the acoustic impedance of the system 219, that is, a physical quantity of the tissue 214, increases. Since the contact 213 is tapered so that its sectional area is reduced toward the distal end in the axial direction, the acoustic impedance of the organic tissue 214 is enhanced as it is transmitted to the vibrator 211. Thus, the change of the resonance frequency for the vibrator 211 is accelerated sharply, so that the effect of resonance frequency lowering is great.

According to the sixteenth embodiment described above, the resonance state considerably changes with a slight change of the physical quantity or acoustic impedance of the organic tissue 214, so that the frequency and voltage changes are substantial. Despite the simple construction and low price, therefore, the apparatus of the present embodiment can make a high-accuracy physical quantity measurement, sensitively responding to a slight change of the physical quantity. Also, there may be provided a low-priced physical quantity sensor unit that has a relatively simple construction and can be manufactured with ease.

Referring now to FIG. 22, a seventeenth embodiment of the present invention will be described.

FIG. 22 is a longitudinal sectional view showing only the distal end portion of a physical quantity sensor unit according to the seventeenth embodiment. This physical quantity sensor unit is a piezoelectric ceramic member manufactured by integrally forming the contact 213 and the vibrator 211 according to the sixteenth embodiment. The outer peripheral surface of the distal end portion of the contact 213, which is integral with the vibrator 211, is tapered. Since other components and a resonance circuit (not shown) are identical with their counterparts of the sixteenth embodiment, a description of those elements is omitted.

In this arrangement, the vibrator 211 and the contact 213 are formed as one integral part, so that they require no such assembling operation as bonding.

According to the seventeenth embodiment described above, there may be provided a low-priced physical quantity sensor unit that can be assembled more easily without abandoning any of the effects of the sixteenth embodiment.

Putting the effects of the sixteenth and seventeenth embodiments together, there may be provided a relatively low-priced physical quantity sensor unit that can measure physical quantities of organic tissues with high accuracy, and has a relatively simple construction such that it can be manufactured with ease.

Referring now to FIG. 23, an eighteenth embodiment of the present invention will be described. FIG. 23 is a longitudinal sectional view showing only the distal end portion of a physical quantity sensor unit according to the eighteenth embodiment. This physical quantity sensor unit is provided with a rod-shaped contact 213 having a diameter equal to the inside diameter of the cylindrical vibrator 211 according to the sixteenth embodiment. The proximal end portion of the contact 213 is fixedly fitted in the distal end portion of the vibrator 211 in a manner such that the distal end portion of the contact 213 projects forward for a short length from the vibrator 211. Although there are no variations in the respective sectional areas of the vibrator 211 and the contact 213 in the direction of propagation of vibration, the sensor unit is designed so that the sectional area of the vibrator 211 is smaller than that of the contact 213. Further, the sectional area is reduced stepwise at a break of the vibration of the mechanical vibration system 219, that is, at a point where the vibration propagates from the vibrator 211 to the contact 213. Thus, the mechanical vibration system forms a stepped horn. The elastic member 216b has a shape fit for the horn.

According to the eighteenth embodiment described above, both the vibrator 211 and the contact 213 have a straight shape, as well as enjoying the effects of the sixteenth embodiment that ensure improved accuracy based on the varied sectional areas, so that manufacturing these components require no complicated processes of operation. Thus, there may be provided a low-priced physical quantity sensor unit whose contact 213 can be constructed with ease.

Referring now to FIGS. 24A, 24B, 25A and 25B, a nineteenth embodiment of the present invention will be described.

FIG. 24A shows an outline of an endoceliac physical quantity measuring apparatus according to the nineteenth embodiment. In FIG. 24A, numeral 201 denotes an elongate catheter that forms the body of a physical quantity sensor probe. The catheter 201 can be introduced into a patient's body cavity through a guide channel of an endoscope by a measurer (not shown). As shown in FIG. 24B, a casing 202 having the same diameter as the catheter 201 is attached coaxially to the distal end of the catheter. A cap-shaped contact 213 formed of an elastic material is connected to the distal end of the casing 202. The proximal end portion of the contact 213 is coaxially fitted on the distal end portion of the casing 202, and the contact 213 and the casing 202 are coupled in a manner such that their respective outer peripheral surfaces are flush with each other. A plurality of grooves 231 are formed in a fitting peripheral surface portion of the casing 202, and their mating ridges 232 are formed on a fitting peripheral surface portion of the contact 213. As the grooves 231 and the ridges 232 are caused to engage one another, the casing 202 and the contact 213 are connected to each other in a watertight manner. Alternatively, the components 202 and 213 may be fixed by adhesive bonding.

As in the case of the sixteenth embodiment, the distal end of a coil core 206 of the catheter 201 and the distal end portion of the catheter are put on the rearmost end portion of the casing 202. The distal end portion of the catheter 201 is fastened at its spool portion 207 and fixed by means of a sealant 208. On the other hand, the distal end portion of the coil core 206 is brazed to the rearmost end portion of the casing 202.

A cylindrical vibrator 211 is disposed coaxially in the casing 202. While this vibrator 211 is formed of, for example, a piezoelectric ceramic material, it may alternatively be formed of a crystal oscillator, magnetostrictive element, piezoelectric compound material, or piezoelectric polymer, e.g. PVDF. The vibrator 211 is polarized in its radial direction, and is fitted with electrodes on its inner and outer peripheral surfaces, individually. When a voltage that varies with time is applied to the two electrodes on the inner and outer peripheral surfaces by means of feeder cords 212, the vibrator 211 starts mechanical vibration.

The contact 213 has its distal end portion in the shape of a truncated cone, and a metallic core member 233 is provided in its central portion. The core member 233 is attached to the contact 213 by insert molding when the contact 213 is molded. By this insert molding, the elastic material of the contact 213 and the core member 233 are formed integrally in a watertight manner. Synthetic rubber, such as silicone rubber, fluororubber, etc., or resin material, such as polyurethane, fluoroplastics, etc., may be used as the elastic material for the contact 213.

The distal end portion of the contact 213, which has the shape of a truncated cone, is tapered. A flat distal end face of the contact 213 is formed as an abutting portion 215 to be held against an organic tissue 214. Further, the distal end portion of the core member 233 is has the shape of pointed cone, and its conical base portion 233a slightly projects like a flange. Only a pointed conical distal end 234 of the core member 233 is slightly exposed and projects from the abutting portion 215.

The rear end portion of the core member 233 is fitted tight in the distal end portion of the vibrator 211. Thus, the rear end portion of the core member 233 is fixed in a manner such that it is fitted tight in a bore 211a of the vibrator 211, so that the member 233 and the vibrator 211 are intimately in touch with each other. At least the vibrator 211 and the contact 213 constitute a mechanical vibration unit.

A detecting element 218 is located close to and coaxially with the proximal end of the vibrator 211. The element 218 can vibrate in cooperation with the vibrator 211, thus serving as a sensor for monitoring the amplitude and frequency of the vibration of the vibrator 211.

The detecting member 218, like the vibrator 211, may be formed of a piezoelectric ceramic material or crystal oscillator. The contact 213, vibrator 211, and detecting element 218 are held on the inner surface of the casing 202 with the aid of a ring-shaped elastic member 216. Since the elastic member 216 for retention is interposed between the casing 202 and the vibrator 211, the mechanical vibration of the vibrator 211 cannot be transmitted to the casing 202. The contact 213, vibrator 211, and detecting element 218 constitutes a mechanical vibration unit of a mechanical vibration system 219 in the form of an integral unit assembly.

As shown in FIG. 24A, the elastic member 216 for retention is provided at a break in the vibration of the mechanical vibration unit, so that the mechanical vibration cannot be inhibited. The member 216 may be located in any other position than that on the contact 213. The abutting portion 215 of the contact 213 and the rear end of the detecting element 218 are arranged so as to be situated on the loop of the mechanical vibration.

As shown in FIG. 21A, on the other hand, an output signal from the detecting element 218 is applied to the input of a filter circuit 222 through an amplifier circuit 221 of an apparatus that is installed outside the catheter 201, by means of an output cord 220. The output of the filter circuit 222 is applied again to the input of the vibrator 211 in the casing 202, and serves as a driving signal for the vibrator 211. Thus, the vibrator 211, detecting element 218, amplifier circuit 221, and filter circuit 222 form a closed self-oscillation circuit. As this self-oscillation circuit is activated, the mechanical vibration system 219, composed of the vibrator 211, contact 213, and detecting element 218, integrally undergoes mechanical resonance vibration.

Voltage measuring means 225 and frequency measuring means 226 are connected to the output line of the filter circuit 222, whereby the voltage and frequency of the operating self-oscillation circuit can be monitored. These measuring means 225 and 226 may be located in any suitable positions in the self-oscillation circuit.

Figure 25A:
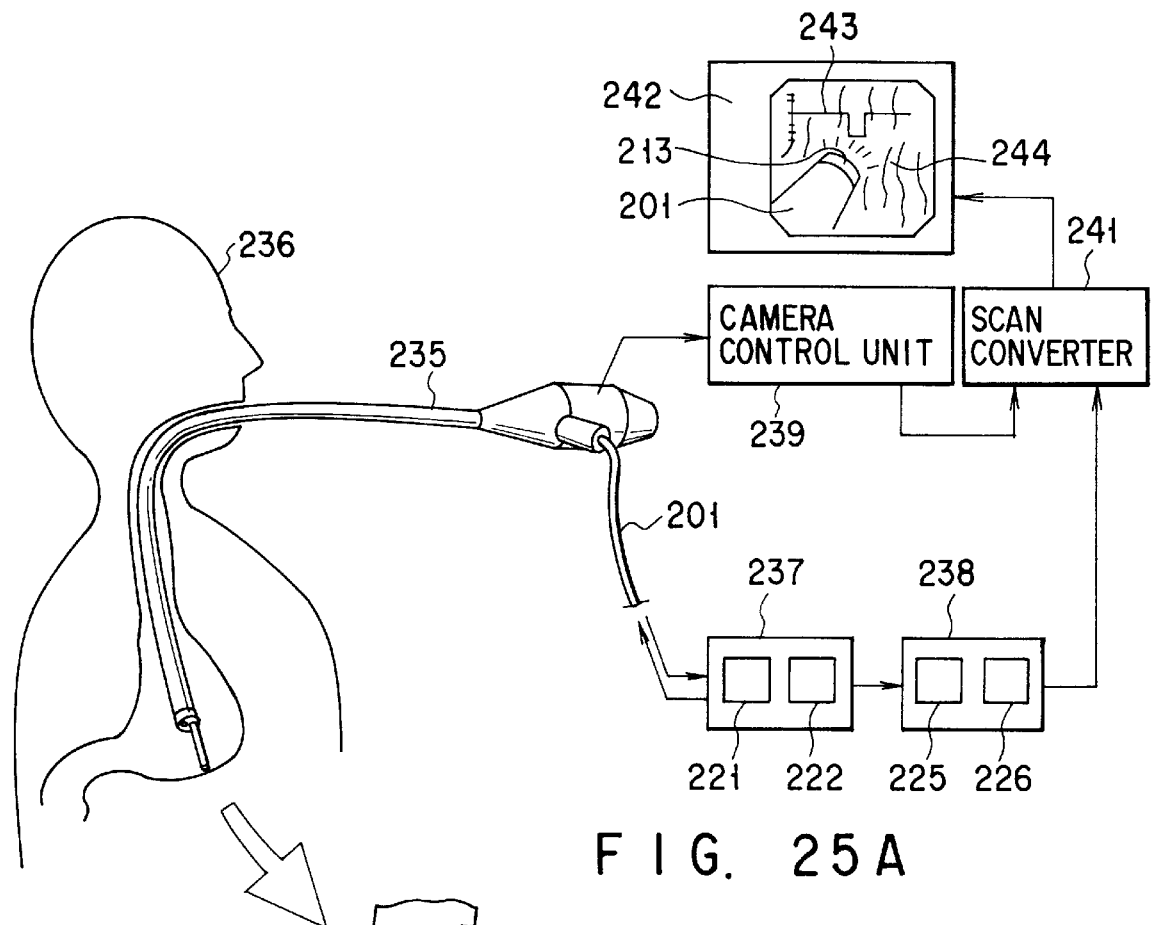
FIG. 25A is a schematic view for illustrating the way of using the sensor unit according to the nineteenth embodiment.
Figure 25B:
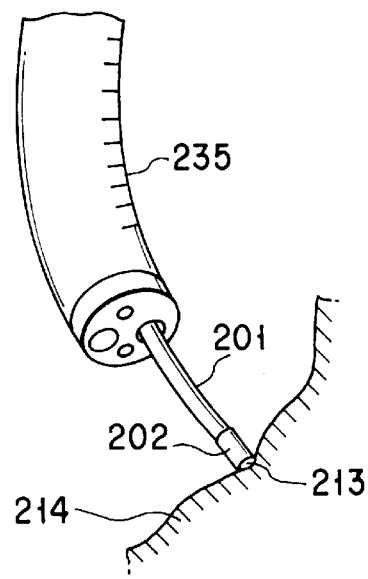
FIG. 25B is a perspective view showing the way the distal end of the sensor unit is held against an organic tissue.

FIG. 25A shows the way the physical quantity sensor unit is inserted into the body cavity of a patient 236 through a guide channel of an endoscope 235 and used to measure physical quantities for the alimentary canal. After the insert section of the endoscope 235 is inserted into the body cavity of the patient 236, the catheter 201 of the physical quantity sensor unit is introduced into the patient's alimentary canal through the channel of the endoscope 235. On the other hand, the amplifier circuit 221 and the filter circuit 222 are arranged in a controller 237 that is located outside the endoscope 235. The voltage measuring means 225 and the frequency measuring means 226 are arranged in a measuring section 238 that is also located outside the endoscope 235. Image signals obtained by means of the endoscope 235 are synthesized into an image by means of a camera control unit 239, and the resulting image is delivered through a scan converter 241 to a monitor 242 to be displayed thereon.

On the other hand, physical quantity information extracted in the measuring section 238 is graphically visualized and applied to the scan converter 241. A graph 243 indicative of the physical quantity information is superimposed on an observation picture of the endoscope 235 in the converter 241, and displayed overlapping a picture 244 on the screen of the monitor 242 obtained by means of the endoscope 225.

According to the nineteenth embodiment described above, the contact 213 can be manufactured as an integral molded component that combines a watertight structure and a vibration absorbing structure, as well as being originally expected to be a member that is adapted to touch the organic tissue 214. Thus, the contact 213 can be used as a low-priced physical quantity sensor unit that combines a plurality of functions, and parts of which can be manufactured and assembled with ease.

The contact 213 may be formed of a ceramic components for its central portion and a less elastic component for its peripheral portion.

Referring now to FIG. 26, a twelfth embodiment of the present invention will be described. A physical quantity sensor unit according to the present embodiment is obtained by omitting the core member 233 of the contact 213 according to the nineteenth embodiment and integrally forming the whole contact 213 from an elastic material.

Referring now to FIG. 27, a twenty-first embodiment of the present invention will be described.

FIG. 27 shows only the distal end portion of a physical quantity sensor unit according to the twenty-first embodiment. In this sensor unit, a fixing member 216 for holding a mechanical vibration system 219, compared with that of the physical quantity sensor unit according to the eighteenth embodiment, is formed of a foamed material such as polystyrene that contains a lot of air.

Since the fixing member 216 contains a lot of air, the twenty-first embodiment can provide an effect, as well as the effects of the sixteenth embodiment, such that the vibration absorbing efficiency of the fixing member is so high that it can absorb the slightest vibration of the vibrator 211 to be transmitted to the casing 202.

According to the twenty-first embodiment described above, the physical quantity sensor can provide an effect, as well as the effects of the eighteenth embodiment, such that the vibration of the vibrator 211 can be cut off substantially thoroughly from the casing 202, thus ensuring high-accuracy measurement.

Referring now to FIG. 28, a twenty-second embodiment of the present invention will be described.

FIG. 28 shows only the distal end portion of a physical quantity sensor unit according to the twenty-second embodiment. In this sensor unit, an elastic fixing member 216, compared with that of the physical quantity sensor unit according to the nineteenth embodiment, is located at the rear end of a detecting element 218 so that the element 218 is connected to a casing 202 by means of the member 216.

According to the twenty-second embodiment described above, a mechanical vibration system 219 composed of a vibrator 211, the detecting element 218, and a contact 213 is fixed to the casing 202 throughout its length from the contact 213 at the distal end to the detecting element 218 at the rear end, so that the individual elements of the system 219 can be positioned accurately with respect to the casing 202. Thus, the physical quantity sensor unit of the present embodiment can provide an effect, as well as the effects of the nineteenth embodiment, such that the constructing and assembling accuracy can be improved to lessen errors in measurement.

According to each embodiment described above, the physical quantity sensor unit is introduced into the body cavity as it is used to measure physical quantities of an organic tissue.

The vibrator according to the present invention is not limited to the structure that is polarized in its radial direction, and may alternatively be polarized in its axial direction and formed by stacking piezoelectric ceramic elements in layers.

Figure 29:
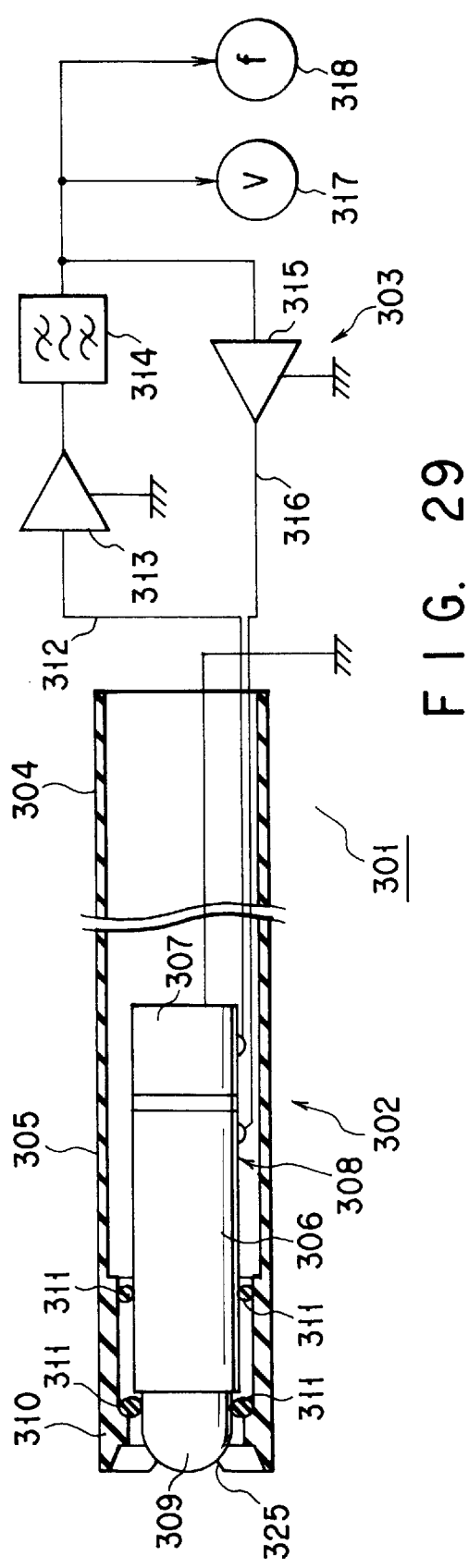
FIG. 29 is a block diagram showing an endoceliac physical quantity measuring apparatus composed of a physical quantity sensor unit and a physical quantity measuring system according to a twenty-third embodiment of the invention.
Figure 30:
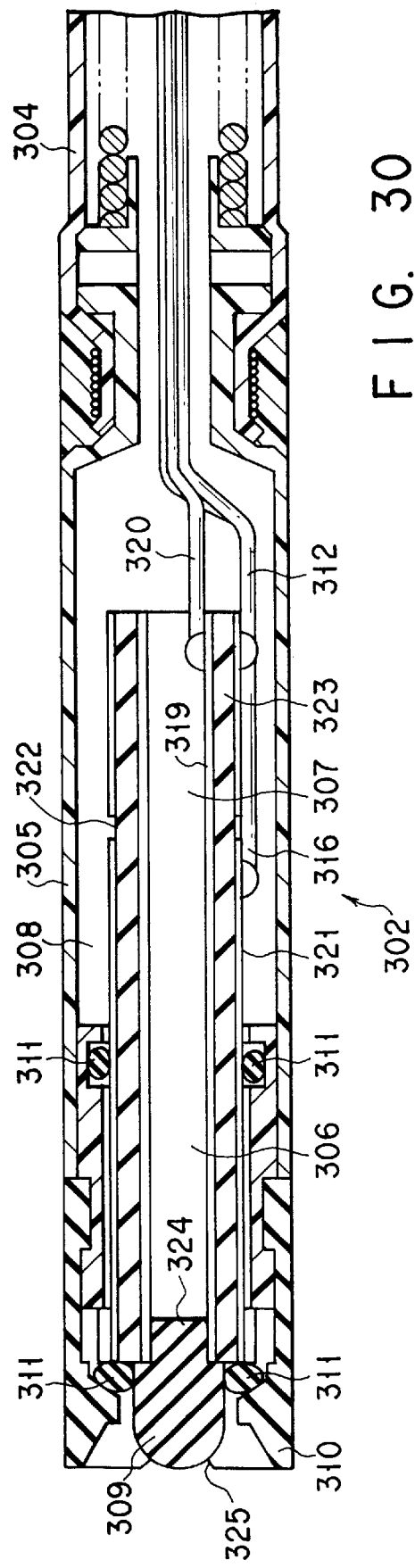
FIG. 30 is a sectional view showing the internal structure of the distal end portion of the sensor unit according to the twenty-third embodiment.

Referring now to FIGS. 29 to 31, a twenty-third embodiment of the present invention will be described. FIG. 29 is a block diagram showing an endoceliac physical quantity measuring apparatus composed of a physical quantity sensor unit and a physical quantity measuring system according to the present embodiment. FIG. 30 is a sectional view showing the internal structure of the distal end portion of the physical quantity sensor unit. FIG. 31 is an exterior view showing an external appearance of the distal end portion of the sensor unit.

As shown in FIG. 29, an endoceliac physical quantity measuring apparatus 301 comprises a physical quantity sensor unit 302 according to the present embodiment and a physical quantity measuring system 303. The measuring system 303 drives the sensor unit 302 and detects signals from the sensor unit, thereby measuring physical quantities.

The physical quantity sensor unit 302 includes a catheter 304 as an outer tube, which is to be held and operated by the operator. A casing 305 is provided at the distal end portion of the catheter 304. The casing 305 contains therein a cylindrical electroacoustic transducer 308, which comprises a vibrating section 306 for generating vibration to be applied to an organic tissue and a detecting section 307 for detecting the mode of vibration of the vibrating section 306. A contact 309 having a dome-shaped external shape is bonded to the distal end portion of the transducer 308. The vibration generated in the transducer 308 is applied to the organic tissue by causing the hemispherical distal end portion of the contact 309 to touch the tissue.

A cylindrical hood member 310, which opens on the distal end side, is attached to the outer periphery of the contact 309. The distal end of the contact 309 projects from the distal end opening of the hood member 310.

The electroacoustic transducer 308 and the contact 309 are held in position in the casing 305 by means of elastic members 311 such as O-rings of rubber. Since the elastic members 311 are interposed between the casing 305 and the transducer 308 and between the casing 305 and the contact 309, individually, the generated mechanical vibration can be prevented from being transmitted to the casing 305. The integral mechanical vibration of the electroacoustic transducer 308 and the contact 309 cannot be inhibited if the elastic members 311 are arranged at nodes in the vibration. Since the elastic members 311 are expected only to be able to support the transducer 308 and the contact 309 that are integral with each other, the elastic member on the side of the contact 309 is not indispensable. Thus, depending on the balance of weight, the elastic member may be provided only on the side of the transducer 308.

An output signal from the detecting section 307 is transmitted to the physical quantity measuring system 303 by means of a signal conductor 312, amplified by an amplifier circuit 313 of the measuring system 303, and applied to the input of a filter circuit 314. The filter circuit 314 is a band-pass filter that has specific bandwidths of about 10% above and below the basic oscillation frequency of the electroacoustic transducer 308 and the contact 309 as its center frequency, for example. The circuit 314 serves to remove noises from the output of the detecting section 307 and prevent the transducer 308 from vibrating in an undesired high-order mode.

The output of the filter circuit 314 is amplified by means of a power amplifier 315, and is supplied to the vibrating section 306 by means of a driving conductor 316. The vibration of the vibrating section is detected again in the detecting section 307.

The above channels are connected so that the detected vibration output of the electroacoustic transducer 308 is positively fed back to the driving power of the transducer 308. Thus, the vibrating section 306, detecting section 307, amplifier circuit 313, filter circuit 314, and power amplifier 315 form a closed self-oscillation loop. A mechanical vibration system composed of the electroacoustic transducer 308 and the contact 309 undergoes integral mechanical resonance vibration at a frequency such that the loop gain of the closed loop has its maximum.

On the other hand, the output end of the filter circuit 314 is connected to voltage measuring means 317 for use as a measuring section and frequency measuring means 318, whereby the voltage and frequency of the operating self-oscillation circuit can be monitored. The measuring means 317 and 318 may be located in any positions within the closed loop of the self-oscillation circuit.

Referring now to FIG. 30, the internal structure of the physical quantity sensor unit 302 according to the present embodiment will be described in detail.

The electroacoustic transducer 308, which is contained in the casing 305 and supported by its corresponding elastic member 311, is a cylindrical member formed of a sintered piezoelectric ceramic material, such as PZT. Also, the transducer 308 is polarized in the diametrical direction of its cylinder. A grounding electrode 319 formed of a metal film is provided covering the whole inner peripheral surface of the cylinder, and a grounding conductor 320 is soldered to the electrode 319. The other end of the conductor 320 is connected to the ground level of the physical quantity measuring system 303.

A driving electrode 321 formed of a metal film is provided on the outer peripheral surface of the cylinder of the electroacoustic transducer 308, covering about ¾ of the overall length of its cylindrical portion from the front end thereof to the rear end. The power amplifier 315 is connected to the electrode 321 by means of the driving conductor 316. That portion of the transducer 308 which is covered by the driving electrode 321 forms the vibrating section 306.

A detecting electrode 323 formed of a metal film is provided on that portion of the outer peripheral surface of the cylinder of the electroacoustic transducer 308 which is situated on the rear end side of the driving electrode 321, with a space 322 secured between the electrodes 321 and 323. The detecting electrode 323 is connected to the amplifier circuit 313 by means of the signal conductor 312. That portion of the electroacoustic transducer 308 which is covered by the detecting electrode 323 forms the detecting section 307.

A columnar projection 324 that has an outside diameter a little smaller than the inside diameter of the cylinder of the electroacoustic transducer 308 is formed integrally on the proximal end portion of the dome-shaped contact 309. The projection 324 is inserted tight in the cylindrical portion of the transducer 308, and these two structures are bonded together. Thus, the acoustic connection between the contact 309 and the transducer 308 is firm.

Referring now to FIGS. 30 and 31, the construction of the hood member 310 that is attached to the outer periphery of the contact 309 will be described.

As described above, the hood member 310 is located covering the outer periphery of the contact 309, leaving the distal end portion of the contact exposed. A substantially semicircular notch 325 is cut in the top portion of the hood member 310, so that a gap is formed between the member 310 and the organic tissue even when a ring portion that constitutes the top portion of the member 310 abuts against the organic tissue.

The following is a description of the operation of the physical quantity sensor unit 302 according to the present embodiment.

A measurer operates the catheter 304 to touch the organic tissue with the distal end portion of the contact 309 in resonance vibration. At the same time, the top ring portion of the hood member 310 also touches the organic tissue under pressure.

Since the surface of the organic tissue is wet with fluids, the fluids are discharged through a gap secured by the notch 325. The notch 325 serves as a refuge for a force to pull the organic tissue as the top ring portion of the hood member 310 abuts against the peripheral portion of the surface of the tissue, so that no load acts on the tissue surface.

According to the physical quantity sensor unit 302 constructed in this manner, the hood member 310 abuts and presses against the periphery of a region of the organic tissue to be measured. Even if the object of measurement is a soft structure, such as an organic tissue, therefore, deformation of the measurement region itself can be minimized, and the distal end portion of the contact 309 can be prevented from slipping off the measurement region.

Since the top ring portion of the hood member 310 is in surface contact with the organic tissue, the pressure and angle of engagement of the contact 309 with the measurement region can be made uniform, thus ensuring stable physical quantity measurement.

Since the fluids can be discharged through the gap in the notch 325 with the contact 309 and the hood member 310 in touch with the organic tissue, measurement errors attributable to the presence of a fluid layer on the measurement region can be reduced.

Although the electroacoustic transducer 308 according to the embodiment described above is formed of a piezoelectric ceramic material, it is to be understood that the transducer may be formed of any other material that has a function for electroacoustic conversion. For example, the electroacoustic transducer may be formed of piezoelectric polymer such as PVDF, crystal oscillator, electrostrictive material, or magnetostrictive material.

According to the embodiment described above, moreover, the vibrating section 306 and the detecting section 307 of the electroacoustic transducer 308 are formed by dividing an electrode attached to a sintered piezoelectric ceramic member. Alternatively, however, the vibrating and detecting sections 306 and 307 may be formed from separate piezoelectric ceramic members that are connected acoustically by adhesive bonding or the like.

FIG. 32 is an exterior view, partially in section, showing the distal end structure of a physical quantity sensor unit 326 according to a twenty-fourth embodiment of the present invention. Like reference numerals are used to designate the same members as are used in the twenty-third embodiment, and a description of those members is omitted.

A projection 324 on the proximal end portion of a contact 327 having a tapered distal end is inserted in and bonded to an electroacoustic transducer 308. The contact 327 is surrounded by a hood member 328. The outer periphery of the distal end of the member 328 is tapered, and a through hole or holes 329 are bored through the slanting side face of the member 328.

In the physical quantity sensor unit 326 according to the present embodiment constructed in this manner, fluids from an organic tissue can be discharged through a top opening of the hood member 328, a gap between the inner surface of the slanting side wall of the member 328 and the tapered slope of the contact 327, and the through hole(s) 329, with the contact 327 and the member 328 in touch with the organic tissue.

In the physical quantity sensor unit 326 according to the present embodiment, the through hole 329 for the discharge of fluids can be formed in the side wall of the hood member 328, so that the surface of the member 328 to abut against the organic tissue can be formed into a flat ring-shaped surface without an edge or the like. Thus, the organic tissue cannot be injured by the hood member 328.

Figure 33:
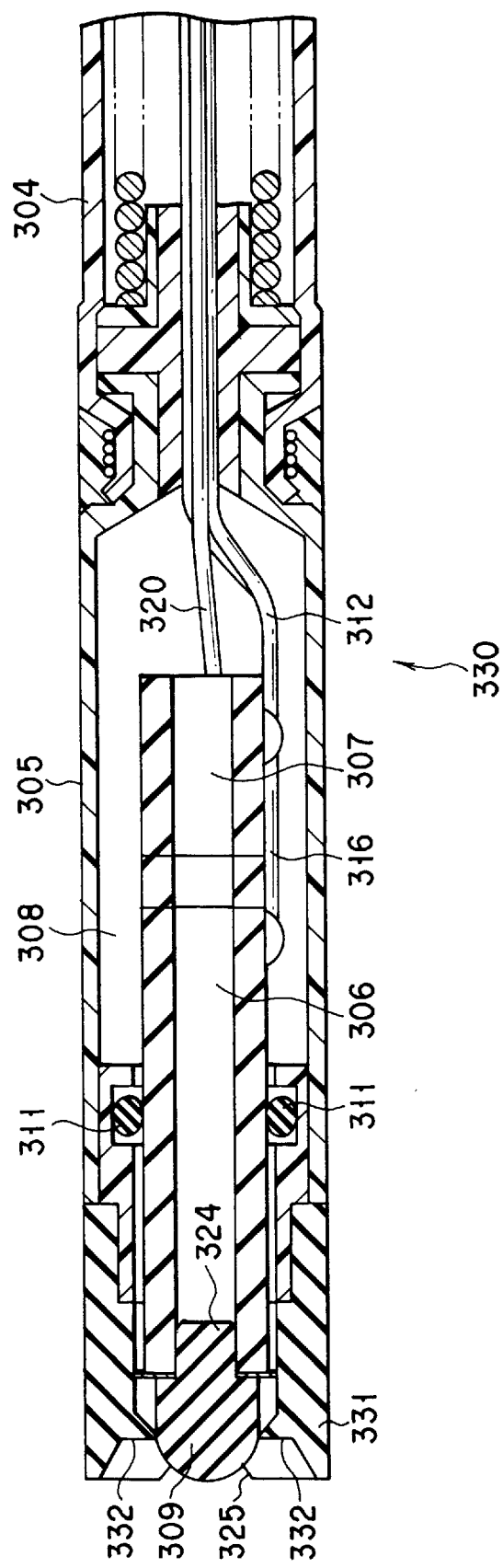
FIG. 33 is a sectional view showing the distal end structure of a physical quantity sensor unit according to a twenty-fifth embodiment of the invention.
Figure 35:
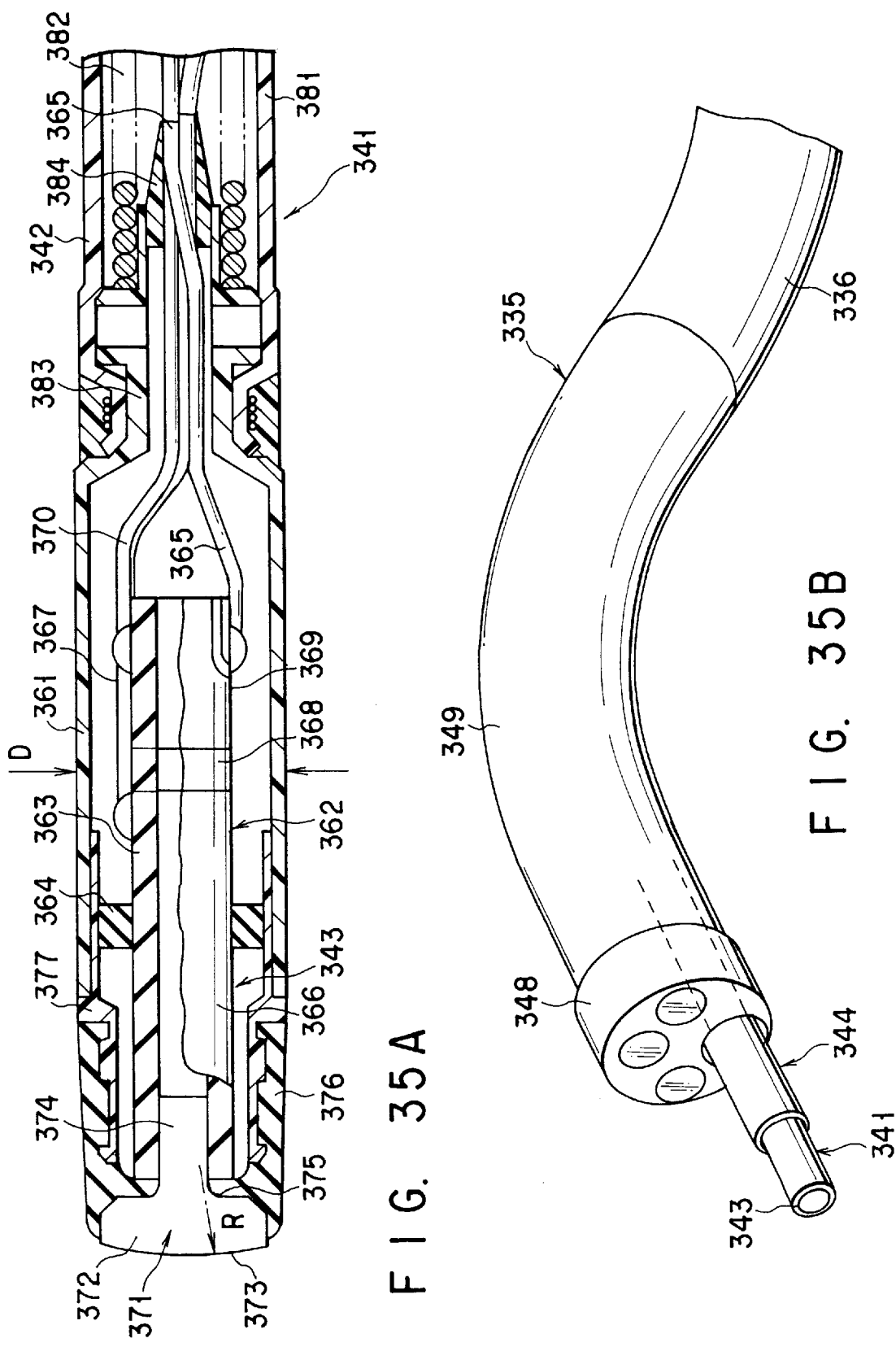
FIG. 35A is a sectional view showing the internal structure of the distal end portion of the sensor unit according to the twenty-sixth embodiment.
FIG. 35B is a perspective view of the distal end portion of an endoscope penetrated by the sensor unit according to the twenty-sixth embodiment.

FIGS. 33 is a sectional view showing the distal end structure of a physical quantity sensor unit 330 according to a twenty-fifth embodiment of the present invention.

The physical quantity sensor unit 330 according to the present embodiment comprises a hood member 331 formed of an elastic material such as silicone rubber. A projection 332 is formed on the inner peripheral surface of the member 331, and serves to support a contact 309. A description of other components, which are arranged in the same manner as those of the twenty-third embodiment, is omitted.

According to the physical quantity sensor unit 330 of the present embodiment, if a measurer applies an undue force to a catheter 304 by mistake, with the hood member 331 in touch with an organic tissue, this force is absorbed as the member 331 is deformed, so that the organic tissue cannot be injured.

Besides the aforesaid silicone rubber, synthetic rubber, such as fluororubber, or high-molecular resin material, such as polyurethane, polyethylene, etc., may be used as the elastic material for the hood member 331.

Figure 37A:
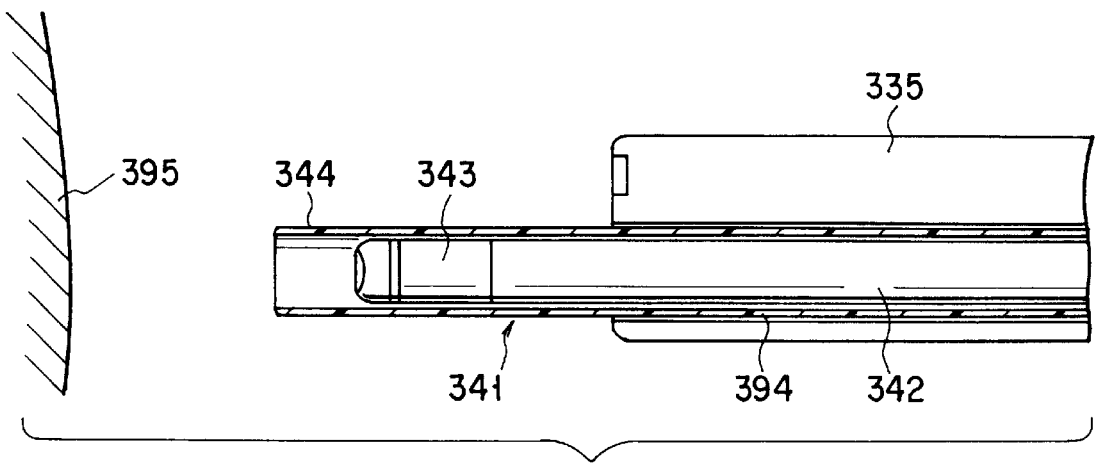
FIGS. 37A, 37B and 37C are diagrams for illustrating steps of procedure for operating the sensor unit according to the twenty-sixth embodiment.
Figure 37B:
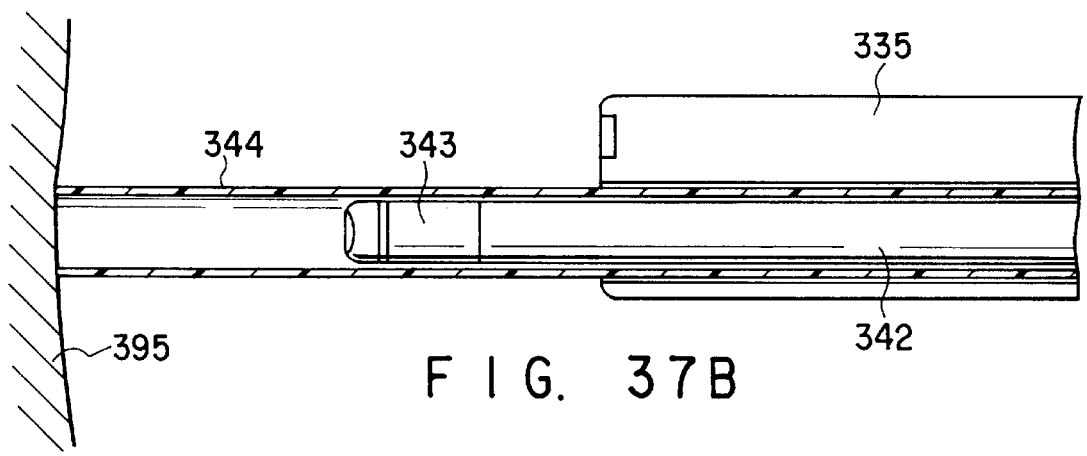
Figure 37C:
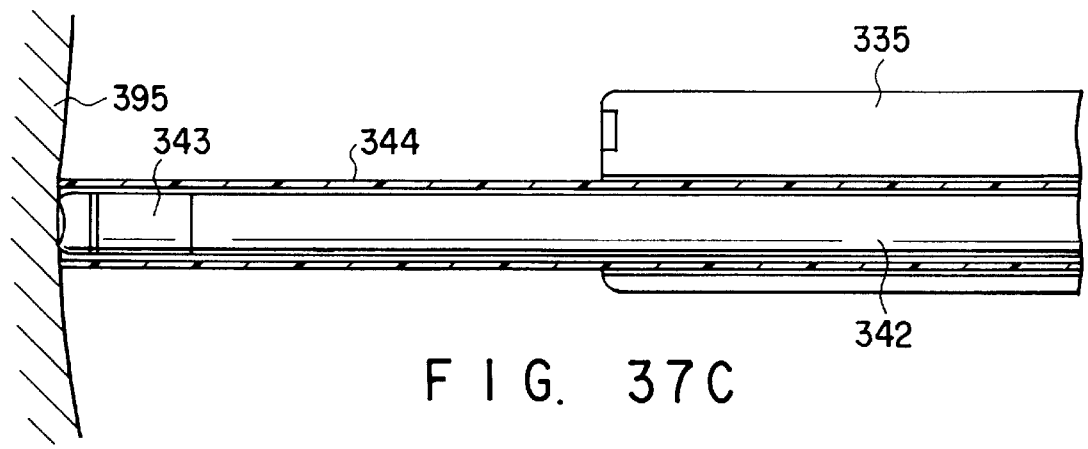

Referring now to FIGS. 34 to 37C, a twenty-sixth embodiment of the present invention will be described. FIG. 34 is a schematic view for illustrating an endoscopic-use arrangement of an endoceliac physical quantity measuring apparatus composed of a physical quantity sensor unit and a physical quantity measuring system according to the present embodiment. FIG. 35A is a sectional view showing the internal structure of the distal end portion of the sensor unit. FIG. 35B is a perspective view of the distal end portion of an endoscope penetrated by the sensor unit. FIG. 36 is a sectional view showing an arrangement of the handling-side portion of the sensor unit fitted with a fixing tube. FIGS. 37A, 37B and 37C are diagrams for illustrating steps of procedure for operating the sensor unit.

In FIG. 34, numeral 335 denotes an endoscope, which comprises an insert section 336 and a control section 337. The control section 337 is connected with a cable 338, which is connected to an endoscopic light source unit 339 and an endoscopic image processor 340. A sensor catheter 341 is inserted in an instrument guide channel (forceps hole) of the endoscope 335, whereby physical quantities of an organic tissue in the body cavity are measured under endoscopic observation.

The sensor catheter 341 includes a flexible insert section 342 that can be inserted into the instrument guide channel of the endoscope 335, and a physical quantity sensor unit 343 is contained in the distal end portion of the insert section 342. A cylindrical flexible member or tube 344, for use as a physical quantity sensor fixing member, is slidably fitted on the insert section 342 of the catheter 341. The insert section 342 of the catheter 341, with the tube 344 fitted thereon, can be inserted into the instrument guide channel of the endoscope 335 through an inlet port 346 in the control section 337 of the endoscope 335, and can be caused to project from a distal end opening 347 of the insert section 336 of the endoscope 335. The endoscope 335 is a flexible endoscope, and the position and direction of its distal end portion 348 can be changed by bending a bendable portion 349.

On the other hand, the sensor catheter 341 is connected to a measuring unit body 351, which contains a measuring unit, such as voltage measuring means, frequency measuring means, etc., and a video signal processing unit. The video signal processing unit of the measuring unit body 351 outputs information on the physical quantity sensor unit 343 as a video signal that can be displayed on a CRT. The video signal from the measuring unit body 351 and a video signal for an endoscopic image from the endoscopic image processor 340 are applied to a superimposing device 353 to be superimposed therein. Thereupon, physical quantity measurement data, along with an endoscopic image 356, is displayed in the form of, for example, a graph 357 on a screen 355 of a TV monitor 354. The physical quantity measurement data is applied to the input of a personal computer 358, whereupon it is processed and stored, and the graph 357 therefor can be displayed.

Referring now to FIG. 35A, the internal structure of the physical quantity sensor unit 343, which is contained in the distal end portion of the insert section 342 of the sensor catheter 341, will be described in detail.

The physical quantity sensor unit 343 includes an electroacoustic transducer 362 that is incorporated in a substantially cylindrical casing 361. The transducer 362 comprises a cylindrical vibrator 363, which is formed of a sintered piezoelectric ceramic material, such as PZT, and is polarized in the diametrical direction of its cylindrical portion. The vibrator 363 is supported by means of an elastic member 364.

A metal film is formed on the peripheral surface of the cylindrical portion of the vibrator 363, and is used as a grounding electrode. A grounding conductor 365 is connected to the grounding electrode by soldering. The other end of the conductor 365 is connected to the ground level of the physical quantity measuring system.

Further, a driving electrode 366 formed of a metal film is provided on the peripheral surface of the vibrator 363, covering about ¾ of the overall length of its cylindrical portion from the front end thereof to the rear end. A driving conductor 367 is connected to the electrode 366. That portion of the vibrator 363 which is covered by the driving electrode 366 constitutes a vibrating section. Furthermore, a detecting electrode 369 formed of a metal film is provided on that portion of the outer peripheral surface of the vibrator 363 which is situated on the rear end side of the driving electrode 366, with a space 368 secured between the electrodes 366 and 369. The detecting electrode 369 is connected to the physical quantity measuring system by means of a signal conductor 370. That portion of the vibrator 363 which is covered by the detecting electrode 369 constitutes a detecting section.

A contact 371 is coupled to the distal end portion of the electroacoustic transducer 362. A distal end portion 372 of the contact 371 forms a large-diameter contact portion, and the distal end face thereof forms a spherical contact surface 373 that can be applied to an organic tissue. The proximal end portion of the contact 371 forms a columnar projection 374 that has an outside diameter a little smaller than the inside diameter of the cylindrical portion of the vibrator 363. The projection 374 is inserted tight in the cylindrical portion of the vibrator 363, and these two structures are bonded together. Thus, the acoustic connection between the transducer 362 and the contact 371 is firm.

A stepped portion at the boundary between the large-diameter distal end portion 372 and the small-diameter projection 374 of the contact 371 is finished with a radius grinding machine to form a radiused surface 375, the section radius of which varies smoothly. Thus, the contact 371 has a shape that changes continuously from the projection 374 at the junction with the electroacoustic transducer 362 to the contact surface 373 at the distal end portion 372. Accordingly, the vibration mode of the whole structure from the transducer 362 to the contact 371 is subject to only minor frequency noises.

The peripheral surface of the distal end portion of the contact 371 that projects from the distal end of the electroacoustic transducer 362 is covered by a cylindrical elastic member 376 formed of an elastic material, such as polyurethane or silicone rubber. The elastic member 376 is coupled to the casing 361 by means of a joint ring 377, and its outside diameter is equal to that of the casing 361. The member 376 supports the distal end portion 372 of the contact 371. The cylindrical proximal end portion of the elastic member 376 is fitted on and bonded to the distal end portion of the joint ring 377. Alternatively, the member 376 may be screwed on the ring 377.

The diameter of the distal end portion 372 of the contact 371 is a little smaller than the outside diameter of the elastic member 376, and the diameter of the contact surface 373 of the distal end portion 372 is maximized. The spherical radius (R) of the contact surface 373 is larger than the diameter (D) of the casing 361 or the elastic member 376 as a coupling member coupled to the distal end portion 372 of the contact 371, especially than the casing diameter. While the outer periphery of the elastic member 376 is slightly tapered on the distal end side, the spherical radius R of the contact surface 373 is larger than the radius of the forefront end of the member 376. Thus, the spherical radius R of the contact surface 373 is larger than the diameter D of the thinnest coupling member.

As shown in FIG. 35A, a flexible part of the insert section 342 of the sensor catheter 341 is composed of a flexible tube 381 and a coil core 382 therein. The respective distal ends of these components 381 and 382 are connected to the proximal end portion of the casing 361 of the physical quantity sensor unit 343. The proximal end portion of the casing 361 has a small-diameter portion 383 on which the flexible tube 381 and the coil core 382 are fitted. The grounding conductor 365, driving conductor 367, and signal conductor 370 are collectively passed through the small-diameter portion 383. These conductors 365, 367 and 370 are fixed together without a gap in the passage portion therefor by soldering or the like, thus forming a lead wire fixing portion 384. In this case, a core of a coaxial cable is used for each of the conductors 367 and 370, and the shielding wire of each coaxial cable serves for the grounding conductor 365. The shielding wire portion of each coaxial cable is obtained by stripping the covering of the cable beyond the proximal end of the small-diameter portion 383 of the casing 361. The respective exposed portions of the shielding wires are joined together, passed together with the driving conductor 367 and the signal conductor 370 through the small-diameter portion 383, and collectively soldered at the proximal end portion of the portion 383.

As shown in FIGS. 34 and 35A, the insert section 342 of the sensor catheter 341 is movably passed through the cylindrical flexible member or tube 344 for use as the physical quantity sensor fixing member. Soft or elastic silicone resin, fluoroplastics, or high-molecular resin material, such as polyurethane, polyethylene, etc., may be used as the elastic material for the tube 344. The tube 344 is formed in a manner such that it can be slidingly inserted into the instrument guide channel of the endoscope 335.

FIG. 36 shows a positioning mechanism that can adjust the position of the sensor catheter 341 relative to the sensor fixing tube 344. A cylindrical sliding grip member 386 is fixedly attached to the handling-side end of the tube 344. The distal end portion of a cylindrical clamp member 387 is slidably fitted in the rear end portion of the grip member 386. The grip member 386 contains therein a coil spring 388 as an elastic member for urging the clamp member 387 rearward. The clamp member 387 is stopped when it is pushed into the grip member 386 for a fixed distances resisting the urging force of the spring 388. A taper portion 389 is formed on the rear end portion of the clamp member 387. A reducible-diameter clamp member 391 is obtained by forming a slit 390 in the rear end portion of the clamp member 387. A tightening ring 392 is screwed on the clamp member 387, and the inner surface of the proximal end portion of the ring 392 is tapered to fit the taper portion 389. As the clamp member 391 is screwed into the ring 392, its bore is reduced in diameter so that the insert section 342 of the sensor catheter 341 passed through the bore can be held in any desired position.

The following is a description of a method of operating the sensor catheter 341. First, the region of the catheter 341 to be held by means of the clamp member 391 is fixed, and is held in position with the member 391. When the clamp member 387 is pushed fully into the grip member 386, the contact surface 373 of the physical quantity sensor unit 343 is situated in a predetermined position relative to the distal end of the sensor fixing tube 344. For example, the surface 373 is located so as to project slightly from the distal end of the tube 344. The contact surface 373 can be made to be pressed with a greater force against the surface of an organic tissue 395 by increasing its projection. The relative positions of the contact surface 373 and the distal end of the tube 344 are selected depending on the nature of the tissue 395, depth of measurement, etc.

The screen 355 of the TV monitor 354 is observed as the insert section 336 of the endoscope 335 is inserted into a patient's body cavity 393, and an organic tissue to be measured for physical quantities is displayed on the TV monitor screen 355.

Then, the sensor catheter 341 and the sensor fixing tube 344 thereon are inserted into an instrument guide channel 394 of the endoscope 335 so that their respective distal ends project from the distal end of the endoscope, as shown in FIG. 37A. Subsequently, only the sensor fixing tube 344 on the catheter 341 is advanced under observation through the endoscope 335, whereupon the distal end of the tube 344 touches the surface of the organic tissue 395, as shown in FIG. 37B. Thus, the distal end of the tube 344 is held in position on the tissue 395.

The sensor catheter 341 is advanced through the tube 344 as a guide, and the physical quantity sensor unit 343 of the catheter 341 is applied to the surface of the organic tissue 395. At this point of time, the clamp member 387 is stopped and restrained from being pushed in further. When measuring operation is then carried out, the resonance state of the physical quantity sensor unit 343 is changed and converted into physical quantity information in the measuring unit body 351. Then, the graph 357 indicative of the physical quantity measurement data is displayed superimposed on the screen 355 of the TV monitor 354. Thereupon, the operator can appreciate physical quantities of the organic tissue 395 as he observes the endoscopic image.

Further, the operator can measure the physical quantities of the organic tissue and see the physical quantity data, while observing the conditions of the organic tissue through the endoscope 335 with the sensor catheter 341 in the instrument guide channel 394 of the endoscope.

In the patient's body cavity 393, in this case, the sensor catheter 341 is guided and held by means of the sensor fixing tube 344, so that the physical quantity sensor unit 343 of the catheter 341 can steadily engage the surface of the organic tissue 395 to be measured, and moreover, measurement conditions, including the angle and pressure of engagement, can be settled freely. Thus, accurate measurement data can be obtained from measurement in appropriate set conditions. Since the position in which the sensor catheter 341 is held by means of the clamp member 387 is adjustable, the force with which the catheter 341 is pressed against the organic tissue can be set accurately. Thus, the measurement conditions are settled so that reliable measurement data can be obtained. Further, a plurality of reliable measurement data can be obtained in various measurement conditions by changing the set force of pressure during the measurement. Furthermore, the load of the physical quantity sensor unit 343 pressed against the organic tissue can be varied by adjusting the repulsive force of the coil spring 388.

Since the spherical radius R of the contact surface 373 of the contact 371 of the physical quantity sensor unit 343 is larger than the diameter D of the coupling member such as the casing 361, the contact 371 can avoid running locally against the surface of the organic tissue 395 with an undue intensive force and excessively deforming the organism, and can extensively engage the organic tissue under a small load. Thus, true physical quantities of the contact surface of the organic tissue 395 can be measured more accurately. A desired steady output can be obtained by only touching the organism with the physical quantity sensor unit 343 under observation through the endoscope 335, in particular.

A notch may be cut in the distal end edge of the sensor fixing tube 344, covering ⅓ of its circumference. If the surface of the organic tissue is wet with fluids, in this case, the fluids can be discharged through the notch. If the top of the distal end of the tube 344 engages the organic tissue, moreover, the notch can serve as a refuge for a force to pull the tissue, so that no load acts on the tissue surface.

Figure 38A:
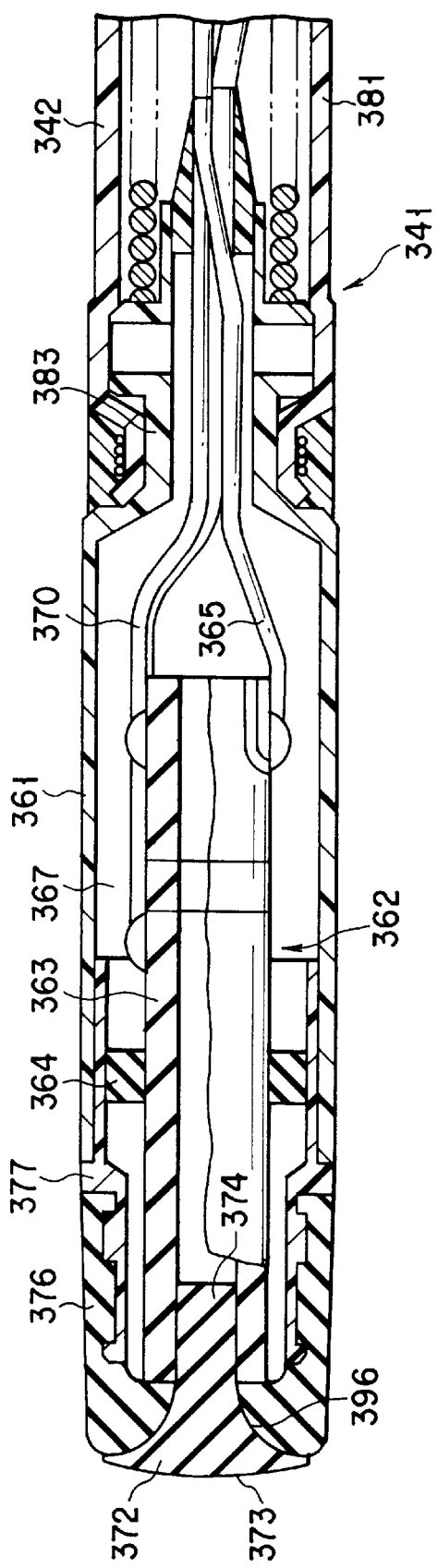
FIG. 38A is a sectional view showing the internal structure of the distal end portion of a modification of the sensor unit according to the twenty-sixth embodiment.

FIG. 38A shows an example of a modified physical quantity sensor unit 343 of a contact 371. In this contact 371, a radiused surface 396 rounded by radius grinding having a relatively wide radius is formed without any sharp difference in level, covering the range from the peripheral edge of the distal end of a large-diameter distal end portion 372 to a small-diameter projection 374. Thus, the profile of the contact 371 is trumpet-shaped. Accordingly, the vibration mode of the whole structure from the electroacoustic transducer 362 to the contact 371 is subject to a lower level of frequency noises than in the case of the twenty-sixth embodiment in which the contact 371 has the radiused surface 375. For the arrangement of other components, this modification resembles the twenty-sixth embodiment.

Figure 38B:
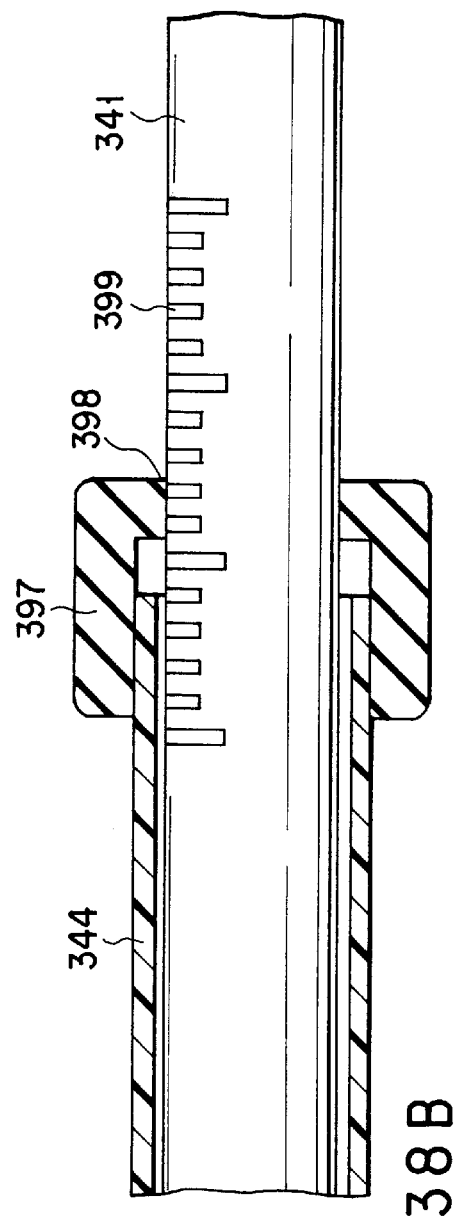
FIG. 38B is a sectional view showing a modification of a positioning mechanism capable of adjusting the position of a sensor catheter relative to a sensor fixing tube.

FIG. 38B shows a modification of the positioning mechanism that can adjust the position of the sensor catheter 341 relative to the sensor fixing tube 344. A cylindrical friction member 397 formed of an elastic material is fixed to the handling-side end of the tube 344, the catheter 341 is slidably passed through the member 397. A ring-shaped rib 398 is formed on the rear end of the friction member 397. The rib 398 elastically presses on the peripheral surface of the catheter 341 to be intimately in contact therewith. As the catheter 341 is advanced or retreated, the rib 398 is in sliding contact with the peripheral surface of the catheter 341, and can hold the catheter 341 in any desired position by means of frictional force. A scale 399 is attached to the outer periphery of the sensor catheter 341, whereby the distal end position of the catheter 341 relative to the distal end of the sensor fixing tube 344 can be identified. According to this arrangement, the position of the catheter 341 can be easily selected and adjusted by only pushing or pulling the catheter relatively to the tube 344.

Figure 39:
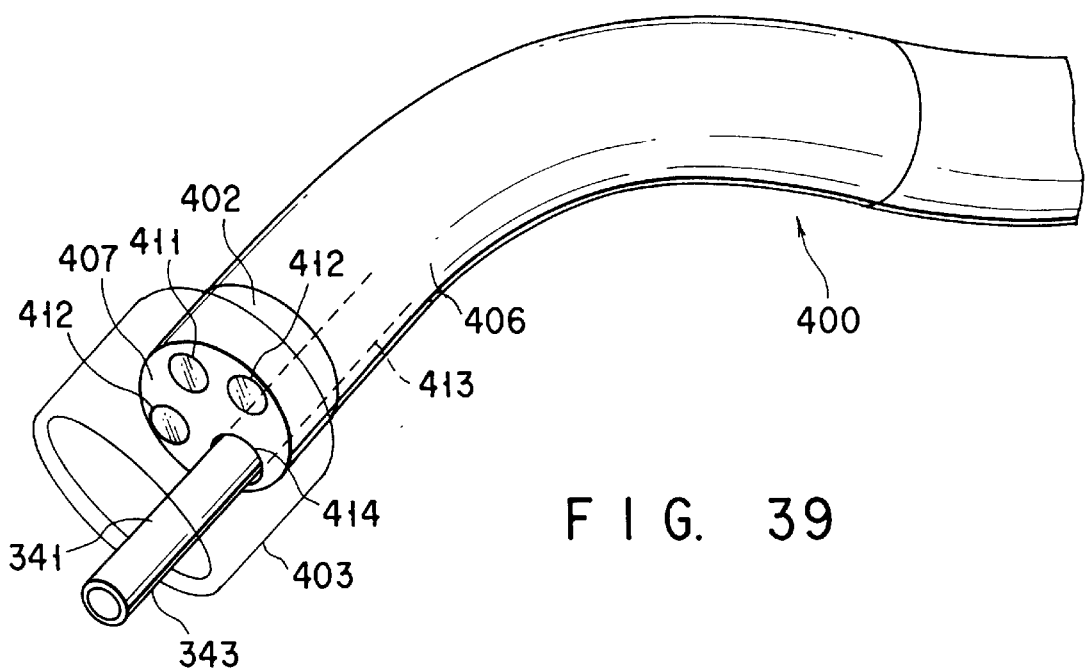
FIG. 39 is a perspective view of the distal end portion of an endoscope penetrated by a physical quantity sensor unit according to a twenty-seventh embodiment of the invention.

Referring now to FIGS. 39, 40A, 40B and 40C, a twenty-seventh embodiment of the present invention will be described. FIG. 39 is a perspective view of the distal end portion of an endoscope penetrated by a physical quantity sensor unit according to the present embodiment. FIGS. 40A, 40B and 40C are diagrams for illustrating steps of procedure for operating the sensor unit according to the present embodiment.

A sensor catheter 341, which contains a physical quantity sensor unit 343 in its distal end, is constructed in the same manner as that of the twenty-sixth embodiment. An endoscope 400 that is used with the catheter 341 is formed by fitting a distal end portion 402 of an insert section 405 with a hood member 403, a transparent cylindrical member for use as a fixing member. The hood member 403, which may be formed of an elastic member, is removably attached to the distal end portion 402 of the endoscope 400. The endoscope 400 is a flexible endoscope, and the position and direction of the distal end portion 402 of its insert section 405 can be changed by bending a bendable portion 406.

The hood member 403 surrounds a distal end face 407 of the distal end portion 402 of the endoscope 400. The distal end face 407, like that of a conventional endoscope, is provided with a view window 411 and illumination windows 412, along with a distal end opening 414 of an instrument guide channel 413. The sensor catheter 341 can be passed through the channel 413 so as to project into the inside space of the hood member 403 through the opening 414.

The following is a description of a method of operating the sensor catheter 341. First, the insert section 405 of the endoscope 400 is inserted into a patient's body cavity, and the distal end portion 402 is brought close to a region of an organic tissue 416 to be measured for physical quantities under observation, as shown in FIG. 40A. Then, the distal end edge of the hood member 403 is applied to the surface of the organic tissue 416, whereupon the member 403 is fixedly held on the tissue surface, as shown in FIG. 40B. Thus, the distal end portion 402 of the insert section 405 of the endoscope 400, along with the hood member 403 for use as the fixing member, is also fixed and held in a stable state.

When the sensor catheter 341 in the instrument guide channel 413 of the endoscope 400 is advanced, its distal end can be brought into contact with the surface of that region of the organic tissue 416 which is positioned inside the hood member 403, as shown in FIG. 40C. Thereupon, the resonance state of the physical quantity sensor unit 343 is changed by the contact, so that the output of the sensor unit 343 can be converted into physical quantity information in a measuring unit body.

With the effects of the twenty-third to twenty-seventh embodiments put together, the fixing member engages and positions the object of measurement. Even if the object is a soft structure, such as an organic tissue, therefore, the contact portion of the mechanical vibration system can be prevented from slipping off the measurement region, and can be caused steadily to touch the tissue. Thus, the measurement conditions are settled so that high-accuracy reliable physical quantity measurement can be effected. Since fixing member restrains the measurement region from being deformed, moreover, measurement errors can be reduced, and stable measurement can be carried out with ease.

According to the present embodiment in which the fixing member is movable, furthermore, the measurement conditions for the contact with the organic tissue can be varied accurately and easily.

Figure 41:
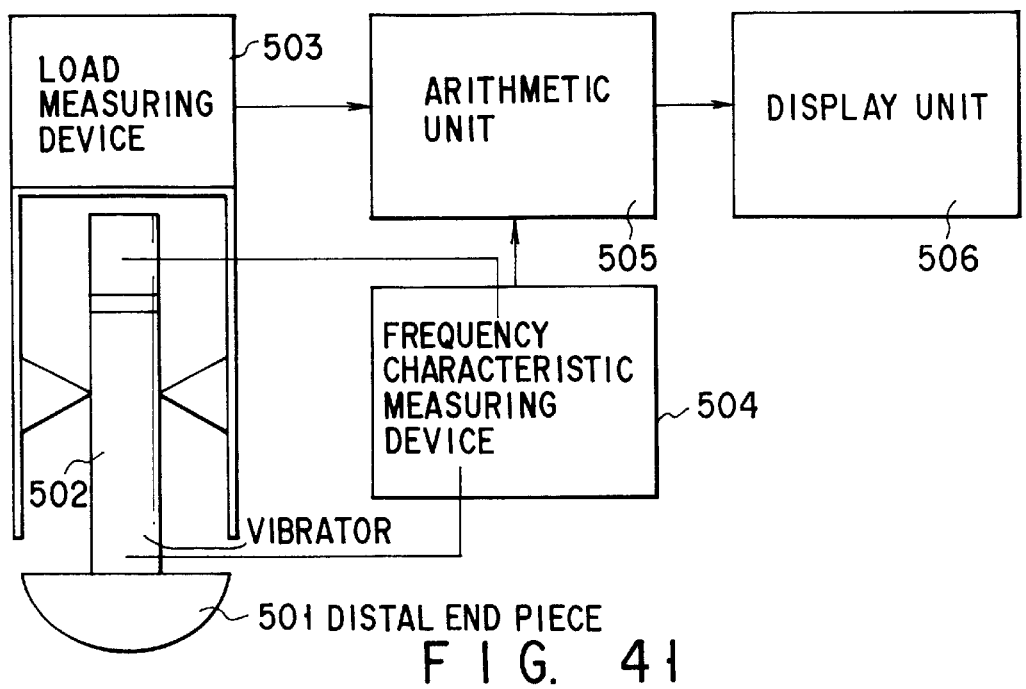
FIG. 41 is a diagram showing an arrangement of a twenty-eighth embodiment of the invention.

The following is a description of a twenty-eighth embodiment of the present invention. FIG. 41 is a diagram showing an arrangement of the twenty-eighth embodiment, which comprises a distal end piece 501, vibrator 502, load measuring device 503, frequency characteristic measuring device 504 such as a network analyzer, arithmetic unit 505, and display unit 506.

The distal end piece 501 is connected mechanically to the vibrator 502. The vibrator 502 is provided with three electrodes (INPUT, OUTPUT, and GND) including a grounding electrode. The electrode INPUT is an electrode to which burst waves from the frequency characteristic measuring device 504 are applied. The electrode OUTPUT is connected to the input of the measuring device 504. The electrode GND is a common grounding electrode. The device 504 measures the input and output characteristics (gain, phase rotation, etc.) of the vibrator 502 within the frequency range of the burst waves. The load measuring device 503 detects a force that acts between the distal end piece 501 and an organic tissue as an object of measurement. On receiving output signals from the measuring devices 503 and 504, the arithmetic unit 505 computes a physical quantity (viscosity) of the organic tissue. The display unit 506 displays the result of computation of the arithmetic unit 505 to the operator.

In connection with the arrangement described above, full lines in FIG. 42 individually represent the characteristics of the vibrator 502 in the vicinity of the basic natural frequency observed by means of the frequency characteristic measuring device 504. In this case, the phase angle of the output signal compared with the input signal at the frequency corresponding to the highest gain is a little less than 90°.

Figure 42:
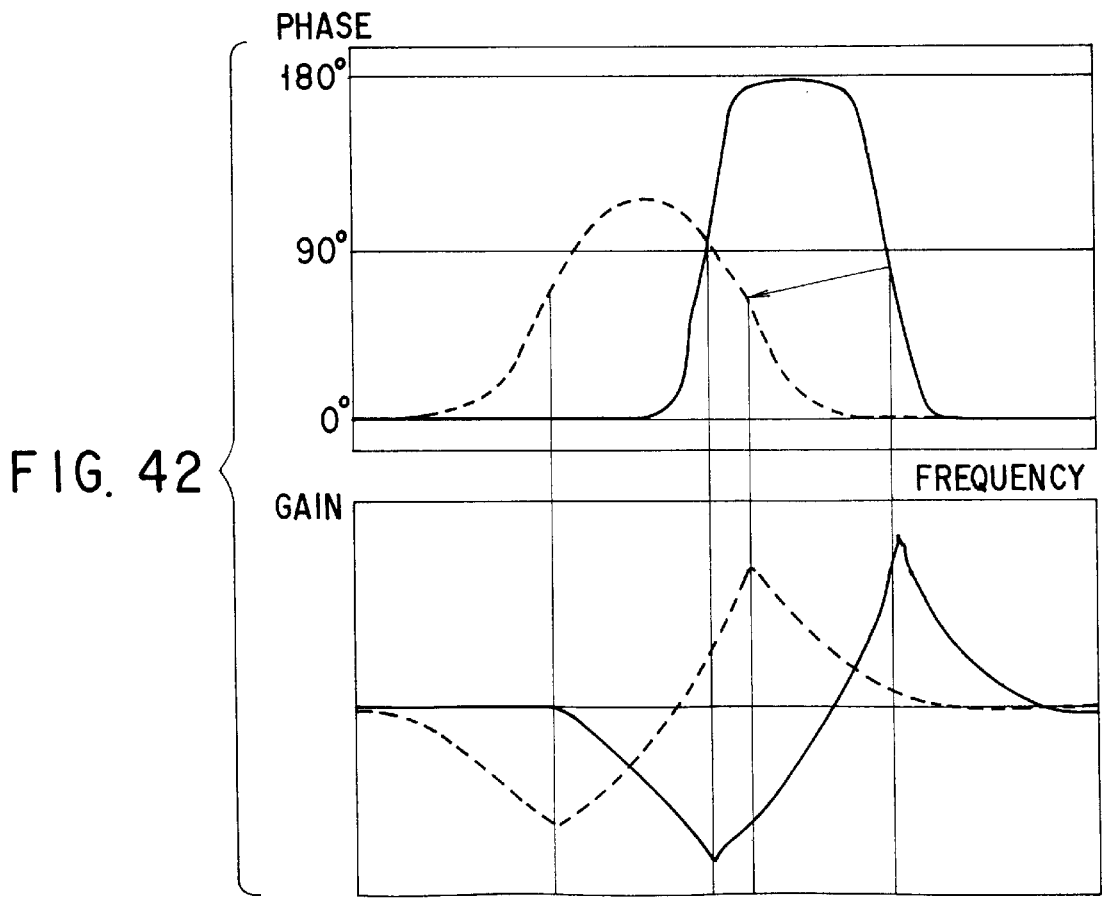
FIG. 42 is a diagram showing characteristics of a vibrator in the vicinity of a basic natural frequency observed by means of a frequency characteristic measuring device shown in FIG. 41.

When the distal end piece 501 is caused to touch the organic tissue, the frequency characteristics of the vibrator 502 vary in the manner indicated by broken lines in FIG. 42. In this case, the phase angle of the output signal compared with the input signal at the frequency corresponding to the highest gain is reduced. This phase change depends on the load and the viscosity of the organic tissue.

Accordingly, the inclination of the curve shown in FIG. 43 represents the viscosity of the organic tissue. Thus, the physical quantity (viscosity) of the organic tissue can be obtained by identifying the relation (inclination of the curve shown in FIG. 43) between the load and the aforesaid phase during the measurement.

The following is a description of the measuring operation. The output of the load measuring device 503 and phase information (phase of gain-maximum frequency) on the vibrator 502 are measured a plurality of times at short time intervals. The measured data are approximated to calculate the inclination by the method of least squares in the arithmetic unit 505, and the viscosity of the organic tissue is computed according to the value of the inclination. The computed value is displayed on the display unit 506.

According to the twenty-eighth embodiment described above, the viscosity of the organic tissue as the object of measurement can be obtained.

Referring now to FIGS. 44A and 44B, a twenty-ninth embodiment of the present invention will be described. FIG. 44A shows a specific arrangement of the amplitude limiting circuit 106 according to the eleventh embodiment, which comprises an amplifier 601a, inverting amplifiers 601b and 601c, and zener diodes 602a and 602b. In FIGS. 44A and 44B, a waveform (i) is obtained by the function of the zener diode 602a when a waveform (h) is inputted. The waveform (h) is inverted by the inverting amplifier 601b, and the resulting inverted waveform (i') is changed into a waveform (j) by the function of the zener diode 602b. The waveform (j) is inverted again by the inverting amplifier 601c, whereupon a limited-amplitude waveform (k) is outputted finally.

Figure 45:
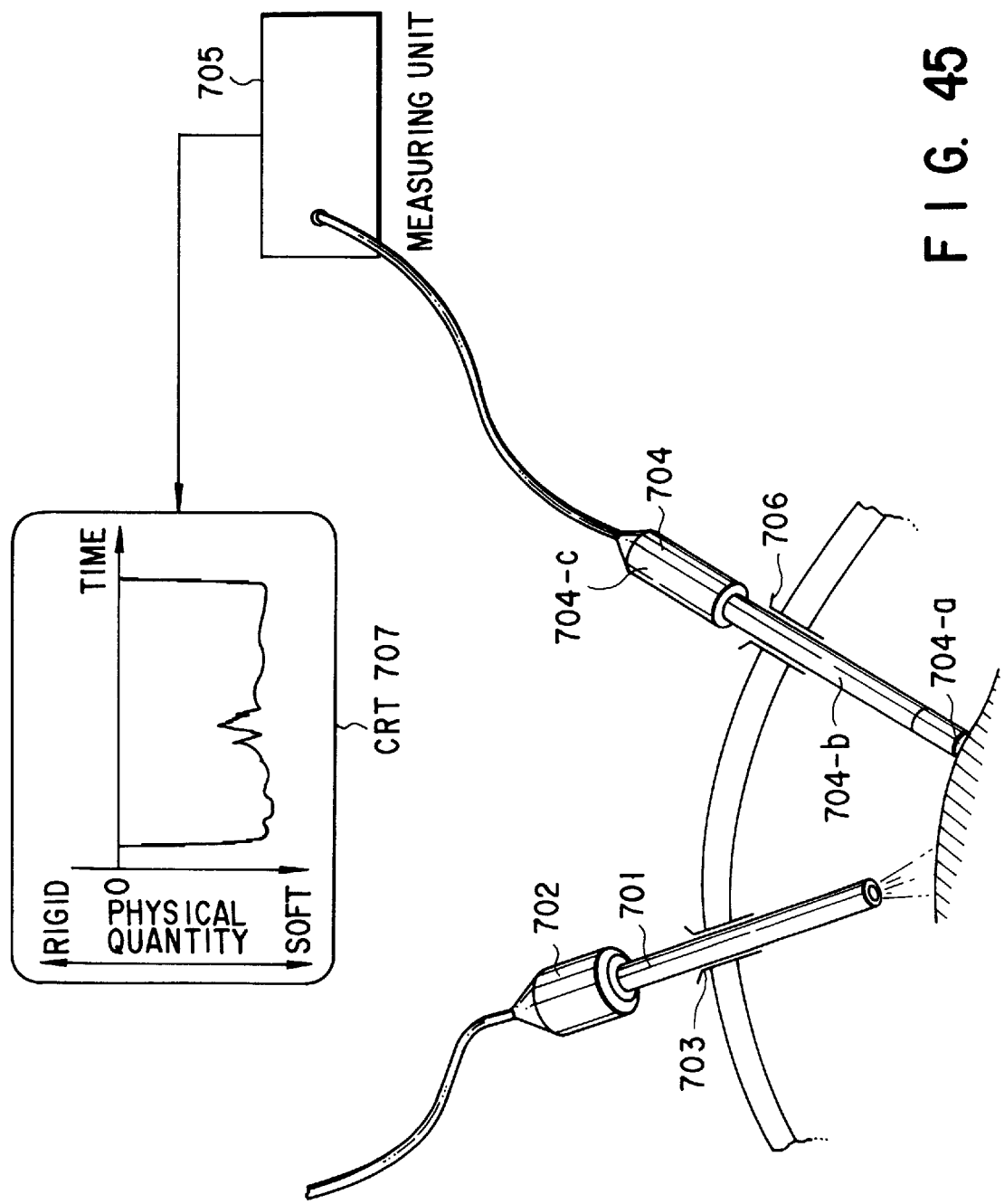
FIG. 45 is a schematic view for illustrating an endoceliac physical quantity measuring apparatus according to the thirtieth embodiment.

Referring now to FIG. 45, a thirtieth embodiment of the present invention will be described. According to the thirtieth embodiment of the present invention, an endoceliac physical quantity measuring apparatus is used in an endoscopic surgical operation.

In FIG. 45, numeral 701 denotes a rigid endoscope; 702, a camera head attached to the endoscope 701; and 703, a first trocar through which the endoscope 701 is passed. The camera head 702 is connected to a video processor (not shown), and the endoscope 701 to a light source unit (not shown). The trocar 703 is transfixed in the surface of a living body. With the rigid endoscope 701 passed through the trocar 703, an image of the interior of the living body cavity can be observed through a view window provided on the distal end of the endoscope 701. Numeral 704 denotes a probe of the endoceliac physical quantity measuring apparatus. According to the present embodiment, the distal end portion of the probe 704 is provided with a distal end piece 704-a, and a high rigidity shaft 704-b to the piece 704-a. Further, the shaft 704-b is fitted with a holding portion 704-c. Numeral 705 denotes a measuring unit of the physical quantity measuring apparatus. An arithmetic unit of the measuring unit 705 is used to compute a physical quantity of an organic tissue on the basis of a sensor output. The computed physical quantity is superimposed on an image obtained by means of the video processor, and is delivered to a CRT 707 only the computed physical quantity is shown in the CRT 707. Numeral 706 denotes a second trocar through which the probe 704 is passed.

The following is a description of the operation of the measuring apparatus.

First, the surface of the living body is stuck with the first trocar 703. The rigid endoscope 701 is passed through the trocar 703 so that the interior of the body cavity can be observed through the endoscope 701. A region of the organic tissue to be measured for the physical quantity is determined. That part of the living body surface through which the measurement region can be approached is stuck with the second trocar 706. The probe 704 of the measuring apparatus is passed through the second trocar 706. Further, the distal end piece 704-a of the probe 704 is pressed against the target region of the organic tissue. The resulting output is computed by means of the measuring unit of the measuring apparatus, and is displayed superimposed on the endoscopic image on the CRT 707. The second trocar 706 may be one that is adapted for use with a forceps or the like in an endoscopic surgical operation.

According to the thirtieth embodiment, physical quantities of an organic tissue in the body cavity can be measured under endoscopic observation.

The endoceliac physical quantity measuring apparatus used in the present embodiment may be any of the apparatuses described herein.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalent.

We claim:

1. An endoceliac physical quantity measuring apparatus comprising:
    a contact adapted to touch an organic tissue;
    a vibrator connected mechanically to the contact;
    a frequency characteristic detecting circuit for detecting parameters associated with frequency characteristics of the vibrator;
    a self-oscillating circuit for subjecting the vibrator to resonance vibration based on a detected vibration state of the vibrator;
    load detecting means for detecting a load acting between the organic tissue and the contact;
    arithmetic means for, when the load detected by the load detecting means reaches a predetermined threshold value, computing physical quantities of the organic tissue based on the parameters associated with the frequency characteristics detected by the frequency characteristic detecting circuit and the load detected by the load detecting means; and
    presentation means for presenting the physical quantities computed by the arithmetic means.

2. An endoceliac physical quantity measuring apparatus according to claim 1, wherein said physical quantities include parameters related to elasticity and density.

3. An endoceliac physical quantity measuring apparatus according to claim 1, wherein said physical quantities include a parameter related to viscosity.

4. An endoceliac physical quantity measuring apparatus according to claim 1, wherein said vibrator includes first and second electrodes, and said oscillating means includes amplifying means for amplifying an output of the first electrode and means for feeding back an output of the amplifying means to the second electrode.

5. An endoceliac physical quantity measuring apparatus according to claim 1, wherein said frequency characteristic detecting circuit includes frequency measuring means for measuring a frequency.

6. An endoceliac physical quantity measuring apparatus according to claim 1, wherein said frequency characteristic detecting circuit includes resonance amplitude measuring means for measuring a resonance amplitude.

7. An endoceliac physical quantity measuring apparatus according to claim 1, wherein said frequency characteristic detecting circuit includes current detecting means for measuring a current flowing through the vibrator.

8. An endoceliac physical quantity measuring apparatus according to claim 1, wherein said self-oscillating circuit includes a band-pass filter in a feedback loop of said oscillating means.

9. An endoceliac physical quantity measuring apparatus according to claim 8, wherein a band-pass frequency of said band-pass filter is different from a resonant frequency of the vibrator in an unloaded state.

10. An endoceliac physical quantity measuring apparatus according to claim 8, wherein a band-pass frequency of said band-pass filter is lower than a resonant frequency of the vibrator in an unloaded state.

11. An endoceliac physical quantity measuring apparatus according to claim 1, wherein said self-oscillating circuit causes the vibrator to vibrate at a fundamental resonant frequency.

12. An endoceliac physical quantity measuring apparatus according to claim 1, wherein said contact, said vibrator, and said load detecting means are connected in succession.

13. An endoceliac physical quantity measuring apparatus according to claim 1, wherein said load detecting means is provided on a fixing member for fixing the vibrator.

14. An endoceliac physical quantity measuring apparatus according to claim 1, wherein said load detecting means is provided integrally with the vibrator.

15. An endoceliac physical quantity measuring apparatus according to claim 1, wherein said load detecting means includes DC voltage detecting means for detecting a DC voltage component generated in the vibrator.

16. An endoceliac physical quantity measuring apparatus according to claim 15, further comprising a third, grounding electrode which is used in common with at least one of the first and second electrodes.

17. An endoceliac physical quantity measuring apparatus according to claim 15, wherein said DC voltage detecting means includes differential voltage detecting means for detecting a difference between an output of the vibrator and an output obtained by passing the vibrator output through a high-pass filter.

18. An endoceliac physical quantity measuring apparatus according to claim 1, wherein said frequency characteristic detecting circuit includes resonance state detecting means for detecting a resonance state, and said arithmetic means computes a physical quantity of the organic tissue based on a feature quantity which is an extreme value of an output of the resonance state detecting means compared with an output of the load detecting means.

19. An endoceliac physical quantity measuring apparatus according to claim 1, wherein said frequency characteristic detecting circuit includes resonance state detecting means for detecting a resonance state, and said arithmetic means computes a physical quantity of the organic tissue based on a feature quantity which is a value of an output of the load detecting means obtained when an output of the resonance state detecting means reaches an extreme value.

20. An endoceliac physical quantity measuring apparatus according to claim 1, wherein said frequency characteristic detecting circuit includes resonance state detecting means for detecting a resonance state, and said arithmetic means computes a physical quantity of the organic tissue based on a feature quantity which is a value of an output of the resonance state detecting means obtained when a value of an output of the load detecting means is constant.

21. An endoceliac physical quantity measuring apparatus according to claim 1, wherein said frequency characteristic detecting circuit includes resonance state detecting means for detecting a resonance state, and said arithmetic means computes a physical quantity of the organic tissue based on a feature quantity which is a value of an output of the load detecting means obtained when a value of an output of the resonance state detecting means is constant.

22. An endoceliac physical quantity measuring apparatus according to claim 1, wherein said frequency characteristic detecting circuit includes resonance state detecting means for detecting a resonance state, and said arithmetic means computes a physical quantity of the organic tissue based on a feature quantity which is a change of an output of the resonance state detecting means compared with a change of an output of the load detecting means.

23. An endoceliac physical quantity measuring apparatus according to claim 1, wherein said frequency characteristic detecting circuit includes resonance state detecting means for detecting a resonance state, and said arithmetic means computes a physical quantity of the organic tissue based on a feature quantity which is a ratio of a change of an output of the resonance state detecting means to a change in an output of the load detecting means immediately after the organic tissue is touched by the contact.

24. An endoceliac physical quantity measuring apparatus according to claim 1, wherein said arithmetic means computes a feature quantity based on a plurality of measuring points on a curve of said load versus said frequency characteristics.

25. An endoceliac physical quantity measuring apparatus according to claim 1, wherein said frequency characteristic detecting circuit includes resonance state detecting means for detecting a resonance state, and said arithmetic means computes a physical quantity of the organic tissue based on a feature quantity which is an extreme value of an output of the resonance state detecting means.

26. An endoceliac physical quantity measuring apparatus according to claim 1, further comprising means for converting a feedback signal from the vibrator into a square form, and for feeding back the converted signal to the vibrator via a band pass filter.

27. An endoceliac physical quantity measuring apparatus according to claim 1, wherein at least a part of said contact is formed of a resin material.

\* \* \* \* \*